(12) United States Patent
Smith et al.

(10) Patent No.: US 9,282,945 B2
(45) Date of Patent: Mar. 15, 2016

(54) CALIBRATION OF ULTRASOUND PROBES

(75) Inventors: David M. Smith, Lodi, CA (US); Sharon L. Adam, San Jose, CA (US); Donald F. Specht, Los Altos, CA (US); Kenneth D. Brewer, Santa Clara, CA (US); John P. Lunsford, San Carlos, CA (US); David J. Specht, San Jose, CA (US)

(73) Assignee: MAUI IMAGING, INC., Sunnyvale, CA (US)

( * ) Notice: Subject to any disclaimer, the term of this patent is extended or adjusted under 35 U.S.C. 154(b) by 763 days.

(21) Appl. No.: 13/279,110

(22) Filed: Oct. 21, 2011

(65) Prior Publication Data
US 2012/0057428 A1  Mar. 8, 2012

Related U.S. Application Data

(63) Continuation-in-part of application No. 12/760,327, filed on Apr. 14, 2010, now Pat. No. 8,473,239.

(60) Provisional application No. 61/169,200, filed on Apr. 14, 2009.

(51) Int. Cl.
*G01F 1/12* (2006.01)
*G10K 11/00* (2006.01)
(Continued)

(52) U.S. Cl.
CPC ............... *A61B 8/00* (2013.01); *A61B 8/4218* (2013.01); *A61B 8/4254* (2013.01);
(Continued)

(58) Field of Classification Search
CPC ........... A61B 2562/046; A61B 8/4483; A61B 2019/5276; A61B 8/406; A61B 8/4254; A61B 8/00; A61B 8/483; A61B 8/08; A61B 8/0883

USPC .................. 702/100, 85, 94, 103, 55, 54, 104
See application file for complete search history.

(56) References Cited

U.S. PATENT DOCUMENTS

| | | |
|---|---|---|
| 3,174,286 A | 3/1965 | Erickson |
| 3,895,381 A | 7/1975 | Kock |

(Continued)

FOREIGN PATENT DOCUMENTS

| | | |
|---|---|---|
| CN | 101190134 A | 6/2008 |
| CN | 102123668 | 7/2011 |

(Continued)

OTHER PUBLICATIONS

Cristianini et al.; An Introduction to Support Vector Machines; Cambridge University Press; pp. 93-111; Mar. 2000.

(Continued)

*Primary Examiner* — Michael Nghiem
*Assistant Examiner* — Eman Alkafawi
(74) *Attorney, Agent, or Firm* — Shay Glenn LLP

(57) ABSTRACT

A method of calibrating an ultrasound probe includes mounting an ultrasound probe onto a calibration system, transmitting an ultrasound test signal from an element of the probe through a test medium of the calibration system, and receiving the test signal on a matrix of hydrophones such that an element's position relative to other elements and other arrays within the same probe can be computed. Further, the system described herein is configured to detect the acoustic performance of elements of a probe and report the results to an end user or service provider.

33 Claims, 43 Drawing Sheets

Assembled test fixture in tank.

(51) Int. Cl.
*A61B 8/00* (2006.01)
*G01S 7/52* (2006.01)
*G01S 15/89* (2006.01)

(52) U.S. Cl.
CPC ............ *A61B 8/4444* (2013.01); *A61B 8/4477* (2013.01); *A61B 8/4483* (2013.01); *A61B 8/587* (2013.01); *G01S 7/5205* (2013.01); *G01S 15/8913* (2013.01); *G01S 15/8915* (2013.01)

(56) References Cited

U.S. PATENT DOCUMENTS

| | | |
|---|---|---|
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,259,733 A | 3/1981 | Taner et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,539,847 A | 9/1985 | Paap |
| 4,566,459 A | 1/1986 | Umemura et al. |
| 4,567,768 A | 2/1986 | Satoh et al. |
| 4,662,222 A | 5/1987 | Johnson |
| 4,669,482 A | 6/1987 | Ophir |
| 4,682,497 A | 7/1987 | Sasaki |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 5,050,588 A | 9/1991 | Grey et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,355,888 A | 10/1994 | Kendall |
| 5,398,216 A | 3/1995 | Hall et al. |
| 5,409,010 A | 4/1995 | Beach et al. |
| 5,442,462 A | 8/1995 | Guissin |
| 5,503,152 A * | 4/1996 | Oakley et al. ................. 600/447 |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 * | 7/2001 | Osadchy et al. .............. 600/424 |
| 6,278,949 B1 | 8/2001 | Alam |
| 6,289,230 B1 | 9/2001 | Chaiken et al. |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |

(56) References Cited

U.S. PATENT DOCUMENTS

| | | | |
|---|---|---|---|
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 * | 8/2011 | Specht ............... A61B 8/42 600/437 |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,279,705 B2 | 10/2012 | Choi et al. |
| 8,412,307 B2 | 4/2013 | Willis et al. |
| 8,419,642 B2 | 4/2013 | Sandrin et al. |
| 8,473,239 B2 * | 6/2013 | Specht et al. ............... 702/100 |
| 8,478,382 B2 | 7/2013 | Burnside et al. |
| 8,532,951 B2 | 9/2013 | Roy et al. |
| 8,582,848 B2 | 11/2013 | Funka-Lea et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0161299 A1 | 10/2002 | Prater et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0235302 A1 * | 10/2006 | Grossman et al. ............ 600/443 |

(56) References Cited

U.S. PATENT DOCUMENTS

| | | |
|---|---|---|
| 2006/0262291 A1 | 11/2006 | Hess et al. |
| 2006/0262961 A1 | 11/2006 | Holsing et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1* | 6/2007 | Dane et al. ............... 219/121.85 |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1* | 10/2007 | Smith et al. ................... 600/424 |
| 2007/0238999 A1* | 10/2007 | Specht ........................... 600/437 |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1* | 7/2008 | Govari et al. ................... 600/437 |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1* | 12/2008 | Kamiyama et al. ............ 600/443 |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0217124 A1 | 8/2010 | Cooley |
| 2010/0240994 A1 | 9/2010 | Zheng |
| 2010/0249570 A1* | 9/2010 | Carson et al. .................. 600/407 |
| 2010/0249596 A1 | 9/2010 | Magee |
| 2010/0256488 A1 | 10/2010 | Kim et al. |
| 2010/0262013 A1* | 10/2010 | Smith ....................... A61B 8/00 600/459 |
| 2010/0266176 A1 | 10/2010 | Masumoto et al. |
| 2010/0268503 A1* | 10/2010 | Specht et al. .................. 702/104 |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178400 A1 | 7/2011 | Specht et al. |
| 2011/0201933 A1* | 8/2011 | Specht ................ G01S 7/52049 600/443 |
| 2011/0270088 A1 | 11/2011 | Shiina |
| 2011/0301470 A1 | 12/2011 | Sato et al. |
| 2011/0306885 A1 | 12/2011 | Specht |
| 2011/0306886 A1 | 12/2011 | Daft et al. |
| 2011/0319764 A1 | 12/2011 | Okada et al. |
| 2012/0035482 A1 | 2/2012 | Kim et al. |
| 2012/0036934 A1 | 2/2012 | Kröning et al. |
| 2012/0085173 A1 | 4/2012 | Papadopoulos et al. |
| 2012/0101378 A1 | 4/2012 | Lee |
| 2012/0114210 A1 | 5/2012 | Kim et al. |
| 2012/0121150 A1 | 5/2012 | Murashita |
| 2012/0137778 A1 | 6/2012 | Kitazawa et al. |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0035595 A1 | 2/2013 | Specht |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0258805 A1 | 10/2013 | Hansen et al. |
| 2013/0261463 A1 | 10/2013 | Chiang et al. |

(56) References Cited

U.S. PATENT DOCUMENTS

| | | | |
|---|---|---|---|
| 2014/0043933 A1 | 2/2014 | Belevich et al. | |
| 2014/0243673 A1 | 8/2014 | Anand et al. | |
| 2015/0045668 A1* | 2/2015 | Smith | A61B 8/00 600/447 |
| 2015/0157294 A1 | 6/2015 | Smith et al. | |

FOREIGN PATENT DOCUMENTS

| | | |
|---|---|---|
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 2356941 A1 | 8/2011 |
| EP | 1979739 | 10/2011 |
| EP | 2385391 A2 | 11/2011 |
| EP | 2294400 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | S49-11189 A | 1/1974 |
| JP | S54-44375 A | 4/1979 |
| JP | S55-103839 A | 8/1980 |
| JP | 57-31848 A | 2/1982 |
| JP | 59-101143 A | 6/1984 |
| JP | S59-174151 A | 10/1984 |
| JP | S60-13109 U | 1/1985 |
| JP | S60-68836 A | 4/1985 |
| JP | 2-501431 A | 5/1990 |
| JP | 4-67856 | 3/1992 |
| JP | 05-042138 A | 2/1993 |
| JP | 6-125908 A | 5/1994 |
| JP | 7-051266 A | 2/1995 |
| JP | 08-252253 | 10/1996 |
| JP | 9-103429 A | 4/1997 |
| JP | 9-201361 A | 8/1997 |
| JP | 10-216128 A | 8/1998 |
| JP | 11-089833 A | 4/1999 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2005-523792 | 8/2005 |
| JP | 2005-526539 | 9/2005 |
| JP | 2006-61203 A | 3/2006 |
| JP | 2006-122657 A | 5/2006 |
| JP | 2008-122209 | 5/2008 |
| JP | 2008-513763 A | 5/2008 |
| JP | 2008-259541 A | 10/2008 |
| JP | 20105375 | 1/2010 |
| KR | 1020090103408 A | 10/2009 |
| WO | WO 92/18054 A1 | 10/1992 |
| WO | WO 98/00719 A2 | 1/1998 |
| WO | WO02/084594 A2 | 10/2002 |
| WO | WO2005/009245 A1 | 2/2005 |
| WO | WO 2006/114735 A1 | 11/2006 |
| WO | WO 2007/127147 A2 | 11/2007 |
| WO | WO2009/060182 A2 | 5/2009 |
| WO | WO 2010/017445 A2 | 2/2010 |
| WO | WO 2010/095094 A1 | 8/2010 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/059358 A2 | 4/2013 |

OTHER PUBLICATIONS

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 428, 484; Feb. 1994.

Haykin, Simon; Neural Networks: A Comprehensive Foundation (2nd Ed.); Prentice Hall; pp. 156-187;Jul. 16, 1998.

Ledesma-Carbayo et al.; Spatio-temporal nonrigid registration for ultrasound cardiac motion estimation; IEEE Trans. on Medical Imaging; vol. 24; No. 9; Sep. 2005.

Leotta et al.; Quantitative three-dimensional echocardiography by rapid imaging . . . ; J American Society of Echocardiography; vol. 10; No. 8; ppl 830-839; Oct. 1997.

Morrison et al.; A probabilistic neural network based image segmentation network for magnetic resonance images; Proc. Conf. Neural Networks; Baltimore, MD; vol. 3; pp. 60-65; Jun. 1992.

Nadkarni et al.; Cardiac motion synchronization for 3D cardiac ultrasound imaging; Ph.D. Dissertation, University of Western Ontario; Jun. 2002.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Sakas et al.; Preprocessing and volume rendering of 3D ultrasonic data; IEEE Computer Graphics and Applications; pp. 47-54, Jul. 1995.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. on Neural Networks; vol. 2.; No. 6; Nov. 1991.

Specht, D.F.; Blind deconvolution of motion blur using LMS inverse filtering; Lockheed Independent Research (unpublished); Jun. 23, 1975.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

(56) References Cited

OTHER PUBLICATIONS

Specht, Donald F.; U.S. Appl. No. 13/333,611 entitled "Method and Apparatus to Visualize the Coronary Arteries Using Ultrasound," filed Dec. 21, 2011.
Adam et al.; U.S. Appl. No. 13/272,098 entitled "Multiple aperture probe internal apparatus and cable assemblies," filed Oct. 12, 2011.
Smith et al.; U.S. Appl. No. 13/272,105 entitled "Concave Ultrasound Transducers and 3D Arrays," filed Oct. 12, 2011.
Brewer et al.; U.S. Appl. No. 13/730,346 entitled "M-Mode Ultrasound Imaging of Arbitrary Paths," filed Dec. 28, 2012.
Specht et al.; U.S. Appl. No. 13/773,340 entitled "Determining Material Stiffness Using Multiple Aperture Ultrasound," filed Feb. 21, 2013.
Call et al.; U.S. Appl. No. 13/850,823 entitled "Systems and methods for improving ultrasound image quality by applying weighting factors," filed Mar. 26, 2013.
Kramb et al,.; Considerations for using phased array ultrasonics in a fully automated inspection system. Review of Quantitative Nondestructive Evaluation, vol. 23, ed. D. O. Thompson and D. E. Chimenti, pp. 817-825, (month unavailable) 2004.
Sapia et al.; Deconvolution of ultrasonic waveforms using an adaptive wiener filter; Review of Progress in Quantitative Nondestructive Evaluation: vol. 13A; Plenum Press; pp. 855-862; (year of publication is sufficiently earlier than the effective U.S. filing date and any foreign priority date) 1994.
Call et al.; U.S. Appl. No. 13/971,689 entitled "Ultrasound Imaging System Memory Architecture," filed Aug. 20, 2013.
Specht et al.; U.S. Appl. No. 14/078,311 entitled "Imaging with Multiple Aperture Medical Ultrasound and Synchronization of Add-On Systems," filed Nov. 12, 2013.
Specht, D. F.; U.S. Appl. No. 14/157,257 entitled "Method and Apparatus to Produce Ultrasonic Images Using Multiple Apertures," filed Jan. 16, 2014.
Specht et al.; U.S. Appl. No. 13/894,192 entitled "Multiple Aperture Ultrasound Array Alignment Fixture," filed May 14, 2013.
Specht et al.; U.S. Appl. No. 14/279,052 entitled "Ultrasound imaging using apparent point-source transmit transducer," filed May 15, 2014.
Smith et al.; U.S. Appl. No. 14/526,186 entitled "Universal multiple aperture medical ultrasound probe," filed Oct. 28, 2014.
Hendee et al.; Medical Imaging Physics; Wiley-Liss, Inc. 4th Edition; Chap. 19-22; pp. 303-353; © 2002 (year of pub. sufficiently earlier than effective US filing date and any foreign priority date).
Wikipedia; Point cloud; 2 pages; Nov. 24, 2014; retrieved from the internet (https://en.wikipedia.org/w/index.php?title=Point_cloud&oldid=472583138).
Wikipedia; Speed of sound; 17 pages; retrieved from the internet (http:en.wikipedia.org/wiki/Speed_of_sound) Feb. 15, 2011.
Li et al.; An efficient speckle tracking algorithm for ultrasonic imaging; 24; pp. 215-228; Oct. 1, 2002.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Wikipedia; Curve fitting; 5 pages; retrieved from the internet (http:en.wikipedia.org/wiki/Curve_fitting) Dec. 19, 2010.
Smith et al.; U.S. Appl. No. 14/210,015 entitled "Alignment of ultrasound transducer arrays and multiple aperture probe assembly," filed Mar. 13, 2014.

Abeysekera et al.; Alignment and calibration of dual ultrasound transducers using a wedge phantom; Ultrasound in Medicine and Biology; 37(2); pp. 271-279; Feb. 2011.
Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb. 28, 2008.
Chen et al.; Maximum-likelihood source localization and unknown sensor location estimation for wideband signals in the near-field; IEEE Transactions on Signal Processing; 50(8); pp. 1843-1854; Aug. 2002.
Chen et al.; Source localization and tracking of a wideband source using a randomly distributed beamforming sensor array; International Journal of High Performance Computing Applications; 16(3); pp. 259-272; Fall 2002.
Fernandez et al.; High resolution ultrasound beamforming using synthetic and adaptive Imaging techniques; Proceedings IEEE International Symposium on Biomedical Imaging; Washington, D.C.; pp. 433-436; Jul. 7-10, 2002.
Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.
Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.
Hsu et al.; Real-time freehand 3D ultrasound calibration; CUED/F-INFENG/TR 565; Department of Engineering, University of Cambridge, United Kingdom; 14 pages; Sep. 2006.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Urban et al; Implementation of vibro-acoustography on a clinical ultrasound system; IEEE Transactions on Ultrasonics, Ferroelectrics, and Frequency Control; 58(6); pp. 1169-1181; Jun. 2011 (Author Manuscript).
Urban et al; Implementation of vibro-acoustography on a clinical ultrasound system; IEEE Ultrasonics Symposium (IUS); pp. 326-329; Oct. 14, 2010.
Wang et al.; Photoacoustic tomography of biological tissues with high cross-section resolution: reconstruction and experiment; Medical Physics; 29(12); pp. 2799-2805; Dec. 2002.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.

* cited by examiner

Phantom End View

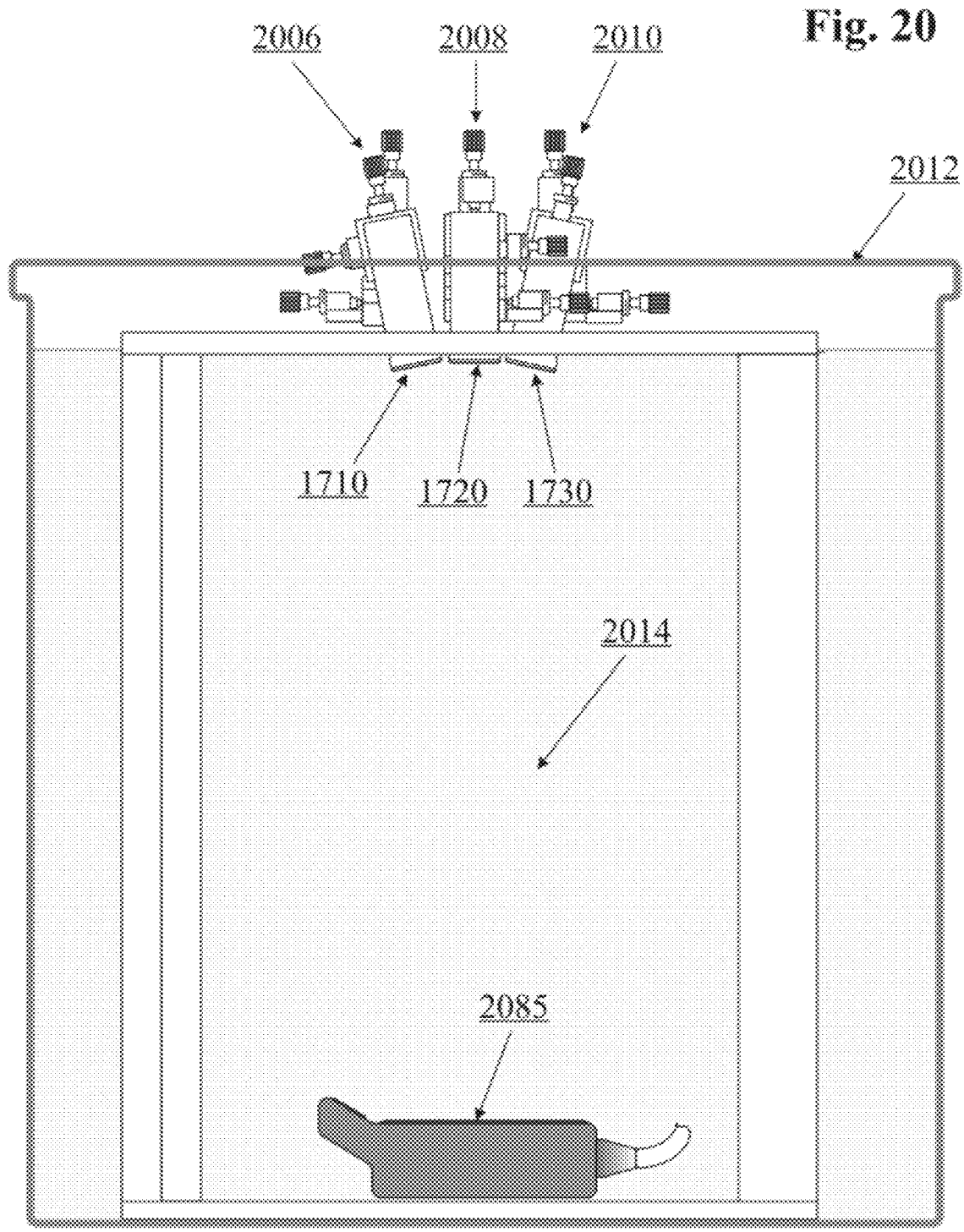
Assembled test fixture in tank.

Fig. 23B
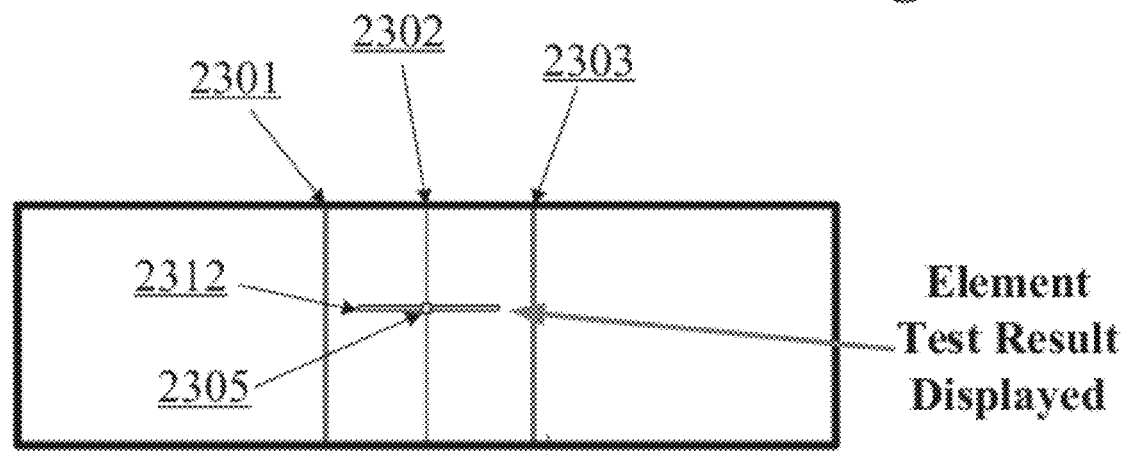
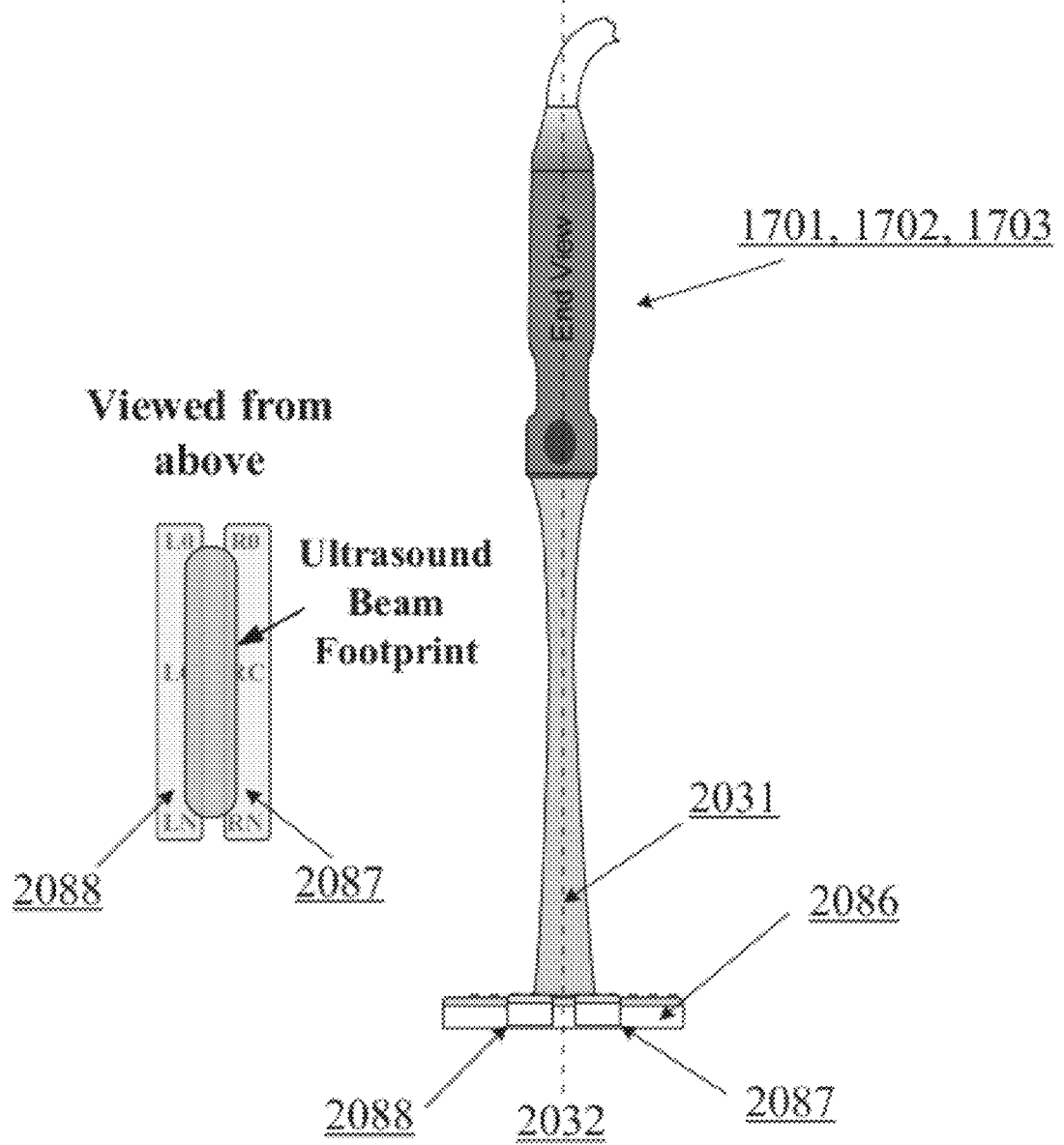

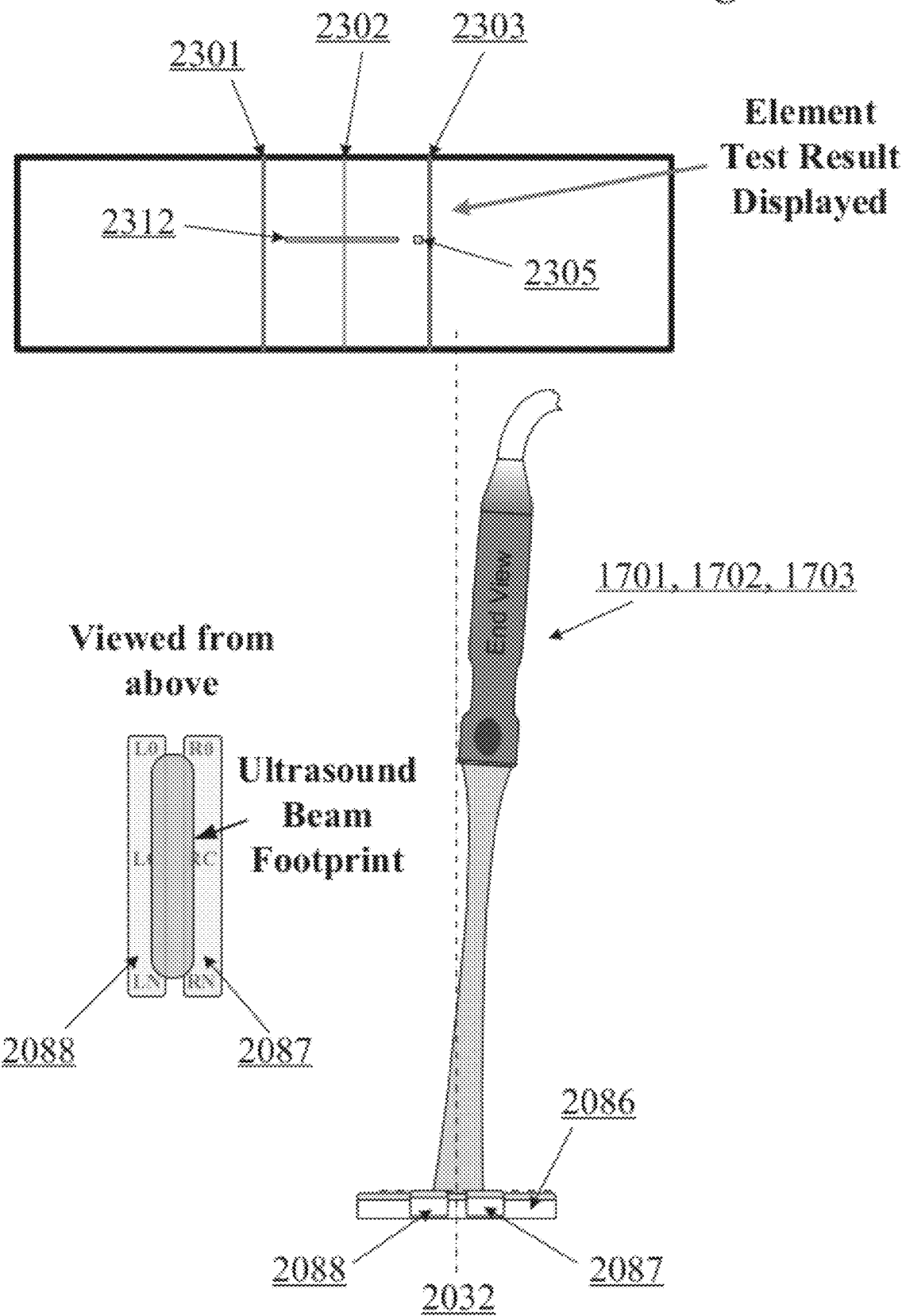

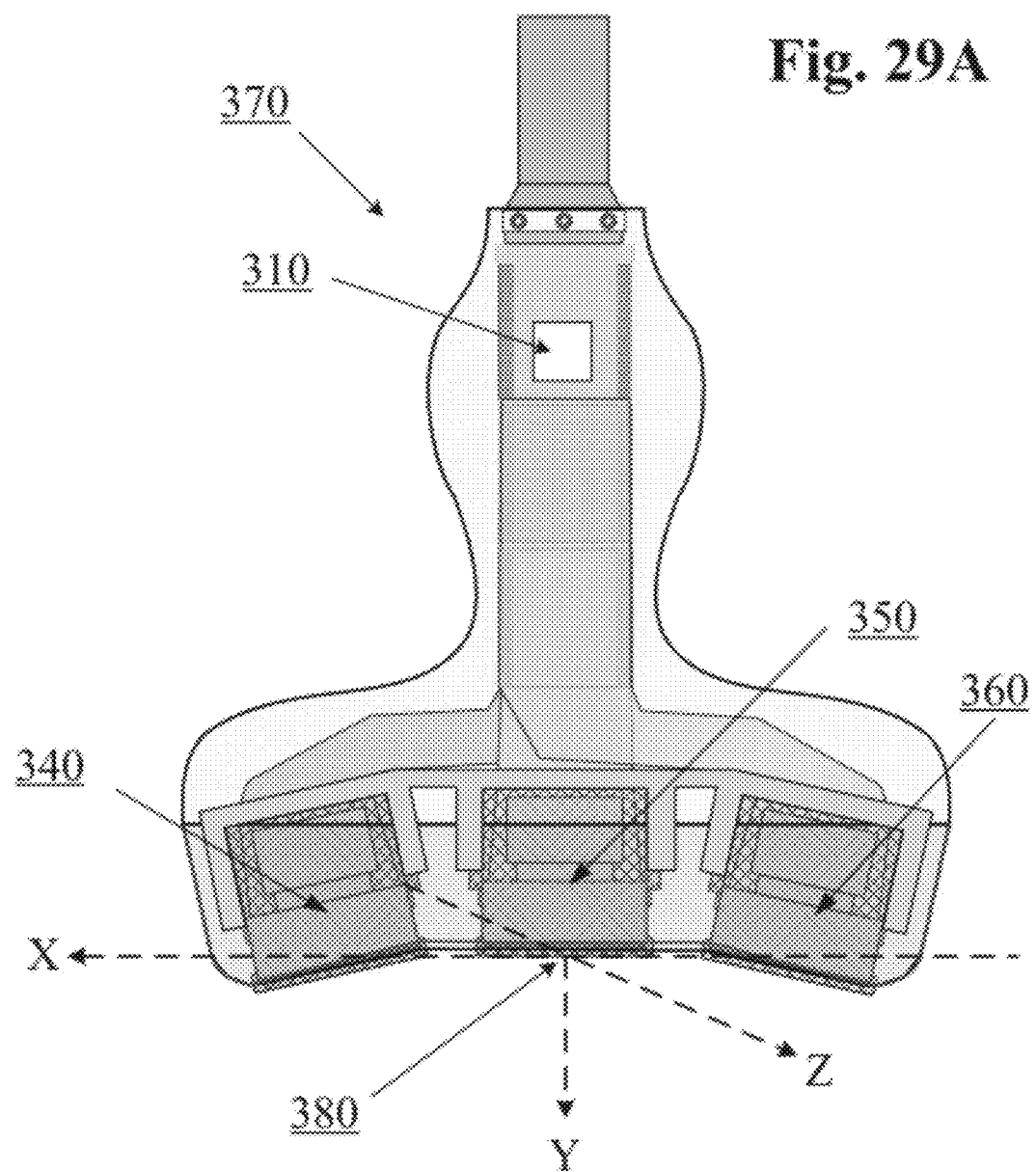

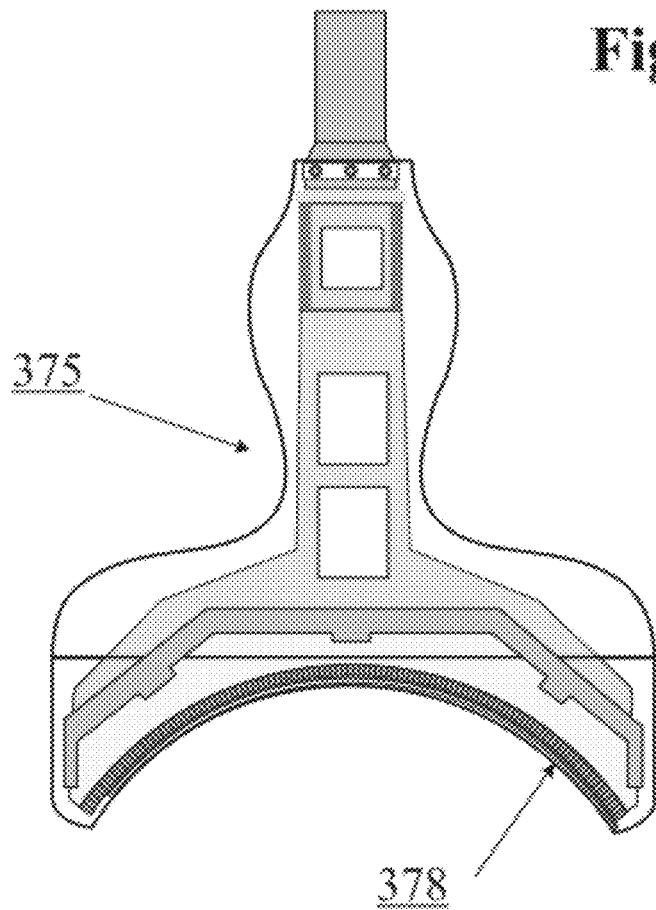

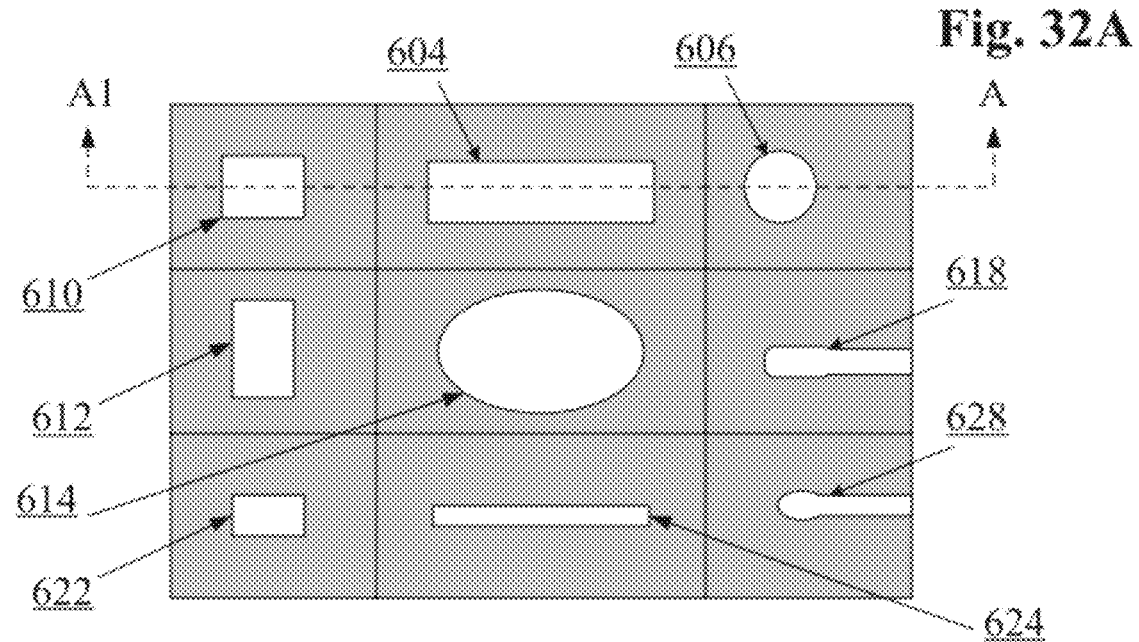
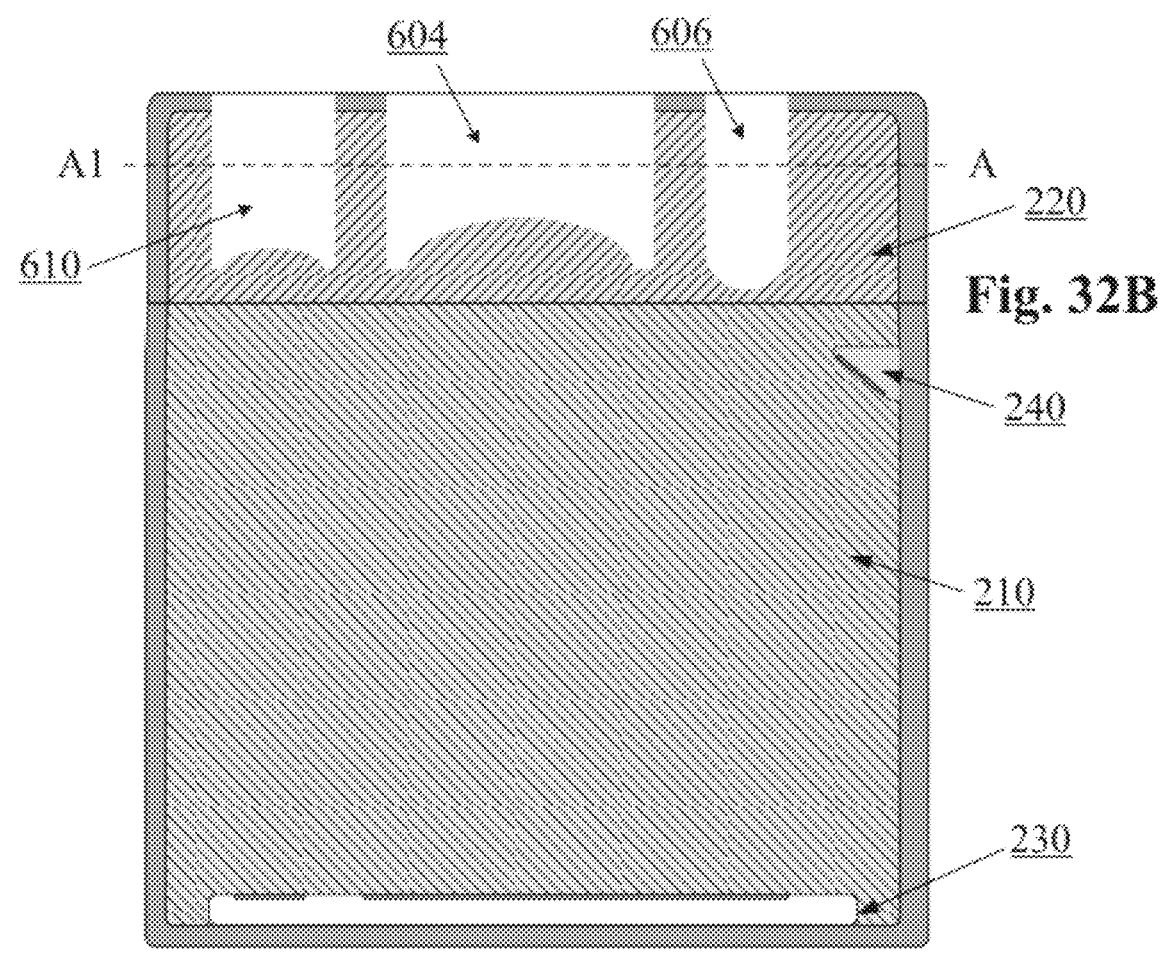

CALIBRATION OF ULTRASOUND PROBES

CROSS REFERENCES TO RELATED APPLICATIONS

This is a Continuation-in-Part of U.S. patent application Ser. No. 12/760,327, filed Apr. 14, 2010, now U.S. Pat. No. 8,473,239, titled "Multiple Aperture Ultrasound Array Alignment Fixture", which was published on Oct. 21, 2010 as U.S. Patent Application Publication No. 2010-0268503, which claims the benefit of U.S. Provisional Patent Application Ser. No. 61/169,200, filed Apr. 14, 2009, titled "Alignment and Fixturing of the Universal Multiple Aperture Medical Ultrasound Transducer". All of the above referenced patents and applications are incorporated herein by reference in their entireties.

This application is relevant to Applicant's co-owned and co-pending patent applications including U.S. patent application Ser. No. 12/760,375, filed Apr. 14, 2010, titled "Universal Multiple Aperture Medical Ultrasound Probe", which was published on Oct. 14, 2010 as U.S Patent Application Publication No. 2010-0262013, and U.S. Provisional Patent Application Ser. No. 61/392,896, filed Oct. 13, 2010, titled "Multiple Aperture Medical Ultrasound Transducers." All of the above referenced patents and applications are incorporated herein by reference in their entireties.

INCORPORATION BY REFERENCE

Unless otherwise specified herein, all patents, publications and patent applications mentioned in this specification are herein incorporated by reference to the same extent as if each individual publication or patent application was specifically and individually indicated to be incorporated by reference.

FIELD

The present invention relates generally to imaging techniques, and more particularly to ultrasound imaging, and still more particularly to systems and methods for calibration and quality assurance measurement of ultrasound probes, particularly probes having multiple apertures.

BACKGROUND

In conventional ultrasonic imaging, a focused beam of ultrasound energy is transmitted into body tissues to be examined and the returned echoes are detected and plotted to form an image. While ultrasound has been used extensively for diagnostic purposes, conventional ultrasound has been greatly limited by depth of scanning, speckle noise, poor lateral resolution, obscured tissues and other such problems.

Significant improvements have been made in the field of ultrasound imaging with the creation of multiple aperture imaging, examples of which are shown and described in Applicant's U.S. Pat. No. 8,007,439 issued Aug. 30, 2011 and titled Method and Apparatus to Produce Ultrasonic images Using Multiple Apertures, U.S. patent application Ser. No. 13/029,907, filed Feb. 18, 2010, titled "Point Source Transmission and Speed-Of-Sound Correction Using Multiple-Aperture Ultrasound. Imaging, and U.S. patent application Ser. No. 12/760,375, filed Apr. 4, 2010, titled "Universal Multiple Aperture Medical Ultrasound Probe," all three of which are incorporated herein by reference. Multiple aperture imaging methods and systems allow for ultrasound signals to be both transmitted and received from separate apertures.

One problem with multiple aperture imaging is that it can be difficult to know the exact position of the elements of a large apparatus with multiple and separate physical points of contact ("footprints") on the patient. It is desirable for each element position to be known to within 1/10 wavelength (for example, 0.03 mm at 3 MHz). In contrast, with conventional ultrasound probes, regardless of array vertical displacement or integration (e.g. 1.5D or 2D), there has never been a need to solve alignment and position issues between multiple arrays or multiple individual elements. The calibration methods and apparatuses described herein teach how to solve these problems for Universal Multiple Aperture ultrasound probes.

SUMMARY

In general, in one aspect, a method of calibrating an ultrasound probe includes mounting an ultrasound probe onto a calibration system, transmitting an ultrasound test signal from an element of the probe through a test medium of the calibration system, receiving the test signal at a first hydrophone of the calibration system at a first time; receiving the test signal at a second hydrophone of the calibration system at a second time, receiving the test signal at a third hydrophone of the calibration system at a third time, and determining an acoustic position of the element based upon differences in the first time, the second time, and the third time.

This and other embodiments may include one or more of the following features.

The elements can be part of an array having a plurality of elements, and the method can further include repeating the transmitting, receiving, and determining steps for at least one additional element in the array. The transmitting, receiving, and determining steps can be performed for every element in the array. The transmitting, receiving, and determining steps can be performed for less than all of the elements in the array, and the method can further include interpolating acoustic positions of all remaining elements. The probe can include a plurality of distinct arrays, and the transmitting, receiving, and determining steps can be performed for at least two elements in each array. The plurality of arrays can be separated by physical space. At least one array can be non-planar with respect to another array.

The first, second, and third hydrophones can be part of a first line of hydrophones and fourth, fifth, and sixth hydrophones can be part of a second line that is parallel to the first line, and the method can further include receiving the test signal on all six hydrophones and determining an x, y, and z position of the element based on differences of arrival times at each hydrophone. Further, there can be a third line of two or more hydrophones that is transverse to the first and second lines, and the method can further include computing the angle of transmission of the element based upon the position of maximum levels of energy received on any of the hydrophones.

The method can further include storing the determine position of the element in a memory chip on the probe. The method can further include overwriting position data stored in a memory chip with the determined position.

The method can further include establishing a tank coordinate system relative to the first, second, or third hydrophone. The method can further include determining a position of every element of the probe relative to the tank coordinate system. The method can further include establishing a probe coordinate system relative to an element of the probe. The method can further include rotating or translating all of the determined positions to the probe coordinate system. The position can be determined relative to a Cartesian coordinate system.

The method can further include storing the determined position in memory and retrieving the stored position during imaging or image processing.

The method can further include transmitting an ultrasound test signal from a fourth hydrophone to the first, second, or third hydrophone to verify the operation of the first, second, or third hydrophone.

In general, in one aspect, a method of determining functionality of an ultrasound probe can include mounting an ultrasound probe onto a calibration system, transmitting an ultrasound signal between a hydrophone of the calibration system and an element of the probe, the transmitting occurring through test medium of the calibration system; and determining an acoustic performance of the element.

This and other embodiments can include one or more of the following features.

The test signal can be transmitted from the hydrophone and received by the element. The test signal can be transmitted from the element and received by the hydrophone.

The element can be part of an array having a plurality of elements, and the method can further include repeating the transmitting, receiving, and determining steps for at least one additional element in the array. The probe can include a plurality of distinct arrays, and the transmitting, receiving, and determining steps can be performed for at least one element of each array.

The test signal can be transmitted by the first, second, or third hydrophone and received by a fourth hydrophone to verify signal performance.

The determined acoustic performance can be stored and transmitted electronically to report probe performance to service providers and end users.

In general, in one aspect, a system for calibrating an ultrasound probe includes a tank substantially filled with a test medium, a dock attached to the tank, and a plurality of hydrophones. The dock is configured to hold an ultrasound probe. The plurality of hydrophones are arranged in a matrix along a wall of the tank opposite the dock.

This and other embodiments can include one or more of the following features.

The system can further include a controller configured to send an ultrasound signal from an element of the probe through the test medium to first, second, and third hydrophones of the plurality of hydrophones, and the controller can be further configured to determine an acoustic position of the element based upon differences in times that the signal is received at the first, second, and third hydrophones.

The system can further include the probe, and the probe can include at least two arrays separated by a physical space, and the dock can be configured so as to hold at least one of the arrays at a non-orthogonal angle with respect to the hydrophone matrix. The probe can include a calibration memory chip configured to store data obtained by the calibration system.

The dock can be configured to conform to the ultrasound probe shape. The dock can be configured such that, when the probe is positioned in the dock, the probe is directly adjacent to the test medium. The material of the dock can have substantially the same speed of sound as the test medium.

The matrix can include a first row of hydrophones, a second row of hydrophones parallel to the first row of hydrophones, and a third row of hydrophones transverse to the first and second rows.

The system can further include a calibrator hydrophone located on a wall of the tank separate from the wall along which the plurality of hydrophone receivers are arranged.

BRIEF DESCRIPTION OF THE FIGURES

FIG. 20 is a representation of probes attached to the precision stage assemblies on top of a fluid filled tank, and well above the hydrophone assembly.

FIG. 23B depicts an array of elements under test with the ultrasound beam in the center of the transverse hydrophone, centered between the left and right hydrophones with the results displayed on the graphical user interface.

FIG. 23C is a representation of an array under test where its beam is on center hut with the array to the right of center with the results displayed on the graphical user interface.

FIG. 29A illustrates a multiple aperture probe containing three separate arrays This figure includes a transducer specific calibration chip mounted within the probe handle.

FIG. 29B illustrates an embodiment of a curvilinear multiple aperture ultrasound imaging probe.

FIG. 32A shows the top view of an embodiment of a calibration system containing a removable docking site which contains multiple docking forms for various shapes and types of probes.

FIG. 32B shows a side view illustrating an embodiment of a calibration system containing a removable docking site having three different docking forms for receiving ultrasound probes.

DETAILED DESCRIPTION

The following disclosure provides embodiments of calibration systems and related operation methods for calibrating ultrasound imaging probes, and particularly multiple aperture ultrasound imaging (MAUI) probes. Embodiments herein also provide systems and methods for operating such a calibration system for various purposes relating to quality assurance of the probes.

In some embodiments, a calibrating system may be configured to identify the location of each and every individual element in an ultrasound probe to a high degree of accuracy and precision. In probes having multiple arrays of transducer elements, a calibration system may be configured to identify the location and/or orientation of individual arrays. In other embodiments, a calibration system may be configured to identify the location of only selected elements of one or more arrays. In some embodiments, the location of elements and/or arrays may be determined in a three dimensional space such as a given X, Y, and Z coordinate system. In other embodiments, the location of elements and/or arrays may be determined in only two dimensions, such as an X, Y coordinate system which may correspond to an imaging plane of the probe.

As used herein, references to the "exact" or "precise" position of transducer elements (and similar terms) may imply a relatively tight tolerance. For example, in some embodiments ultrasound probe calibration systems and methods may provide information describing the acoustic position of each transducer element in an array to within a distance of a fraction of a wavelength of ultrasound being used. In some embodiments, the acoustic position of transducer elements may be determined to within 1/10 of a wavelength. In other embodiments, the acoustic position of transducer elements may be determined to within a tolerance of less than 1/10 of a wavelength. In some embodiments, such as for calibrating a standard (i.e., single aperture) ultrasound probe, much looser tolerances may also be used, provided that such tolerances meet the needs of a particular system.

Figure 1:
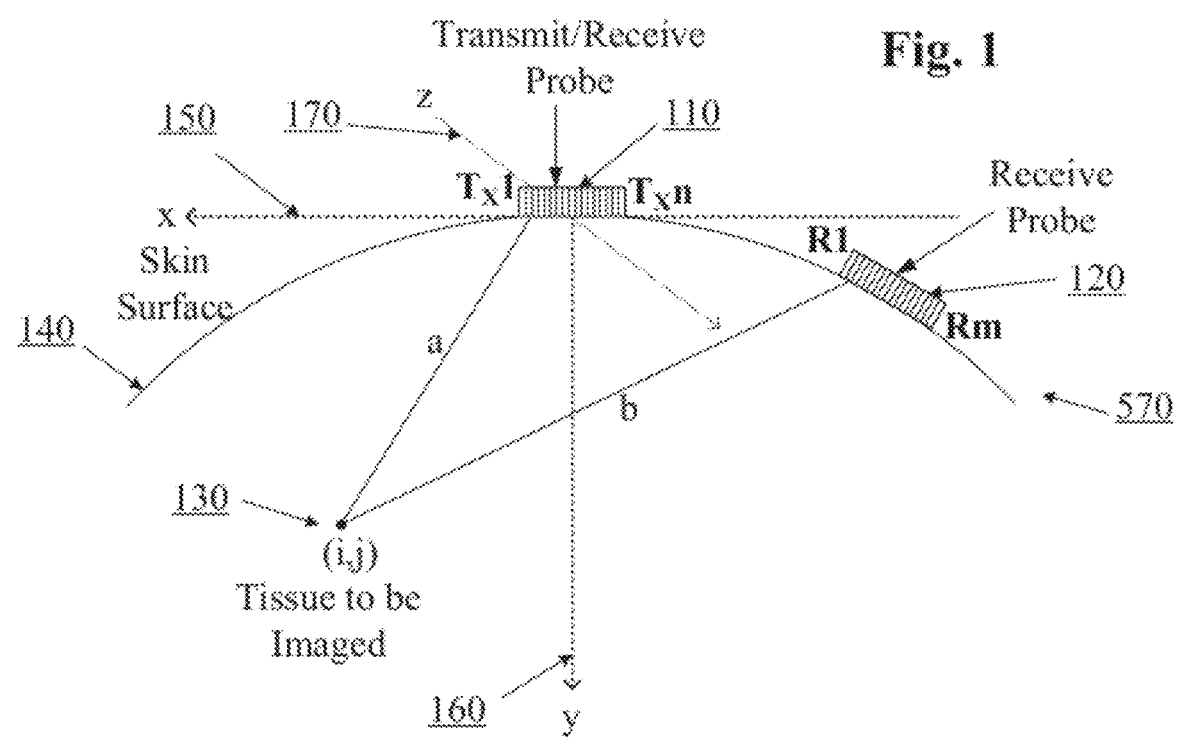
FIG. 1 illustrates a two-aperture system.

The simplest multi-aperture system consists of two apertures, as shown in FIG. 1. One aperture could be used entirely for transmit elements 110 and the other for receive elements 120. Transmit elements can be interspersed with receive elements, or some elements could be used both for transmit and receive. In this example, the probes have two different lines of sight to the tissue to be imaged 130. That is, they maintain two separate physical apertures on the surface of the skin 140. Multiple Aperture Ultrasonic Transducers are not limited to use from the surface of the skin, they can be used anywhere in or on the body to include intracavity and intravenous probes. In transmit/receive probe 110, the positions of the individual elements $T_x1$ through $T_xn$ can be measure in three different axes. This illustration shows the probe perpendicular to the x axis 150, so each element would have a different position x and the same position y on the y axis 160. However, the y axis positions of elements in probe 120 would be different since it is angled down. The z axis 170 comes in or out of the page and is very significant in determine whether an element is in or out of the scan plane.

Referring to FIG. 1, suppose that a Transmit Probe containing ultrasound transmitting elements T1, T2, . . . Tn 110 and a Receive Probe 120 containing ultrasound receive elements R1, R2, . . . Rm are placed on the surface of a body to be examined (such as a human or animal). Both probes can be sensitive to the same plane of scan, and the mechanical position of each element of each probe is known precisely relative to a common reference such as one of the probes. In one embodiment, an ultrasound image can be produced by insonifying the entire region to be imaged (e.g., a plane through the heart, organ, tumor, or other portion of the body) with a transmitting element (e.g., transmit element $T_x1$), and then "walking" down the elements on the Transmit probe (e.g., $T_x2$, $T_xn$) and insonifying the region to be imaged with each of the transmit elements. Individually, the images taken from each transmit element may not be sufficient to provide a high resolution image, but the combination of all the images can provide a high resolution image of the region to be imaged. Then, for a scanning point represented by coordinates (i,j), it is a simple matter to calculate the total distance "a" from a particular transmit element $T_xn$ to an element of tissue 130 plus the distance "b" from the tissue 130 to a particular receive element. With this information, one could begin rendering a map of scatter positions and amplitudes by tracing the echo amplitude to all of the points for the given locus.

Figure 2:
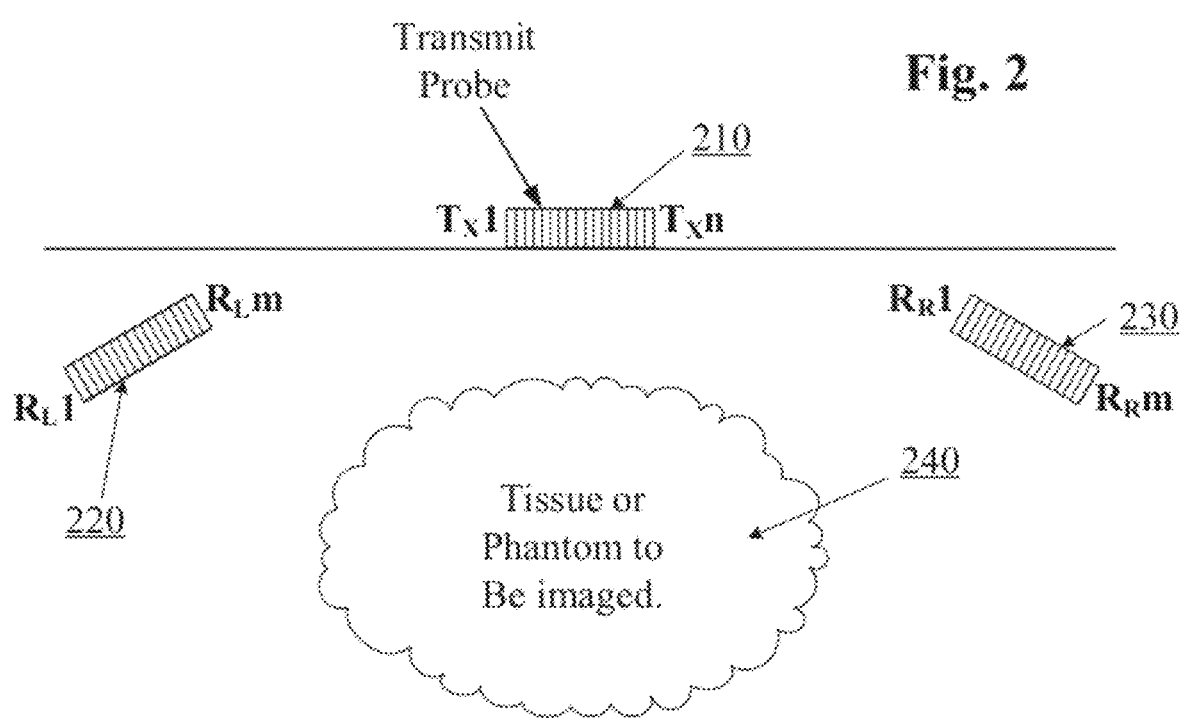
FIG. 2 illustrates a three-aperture system.

Another multi-aperture system is shown FIG. 2 and consists of transducer elements in three apertures. In one concept, elements in the center aperture 210 can be used for transmitting and then elements in the left 220 and right 230 apertures can be used for receiving. Another possibility is that elements in all three apertures can be used for both transmitting and receiving, although the compensation for speed of sound variation would be more complicated under these conditions. Positioning elements or arrays around the tissue 240 to be imaged provides much more data than simply having a single probe 210 over the top of the tissue.

Figure 3:
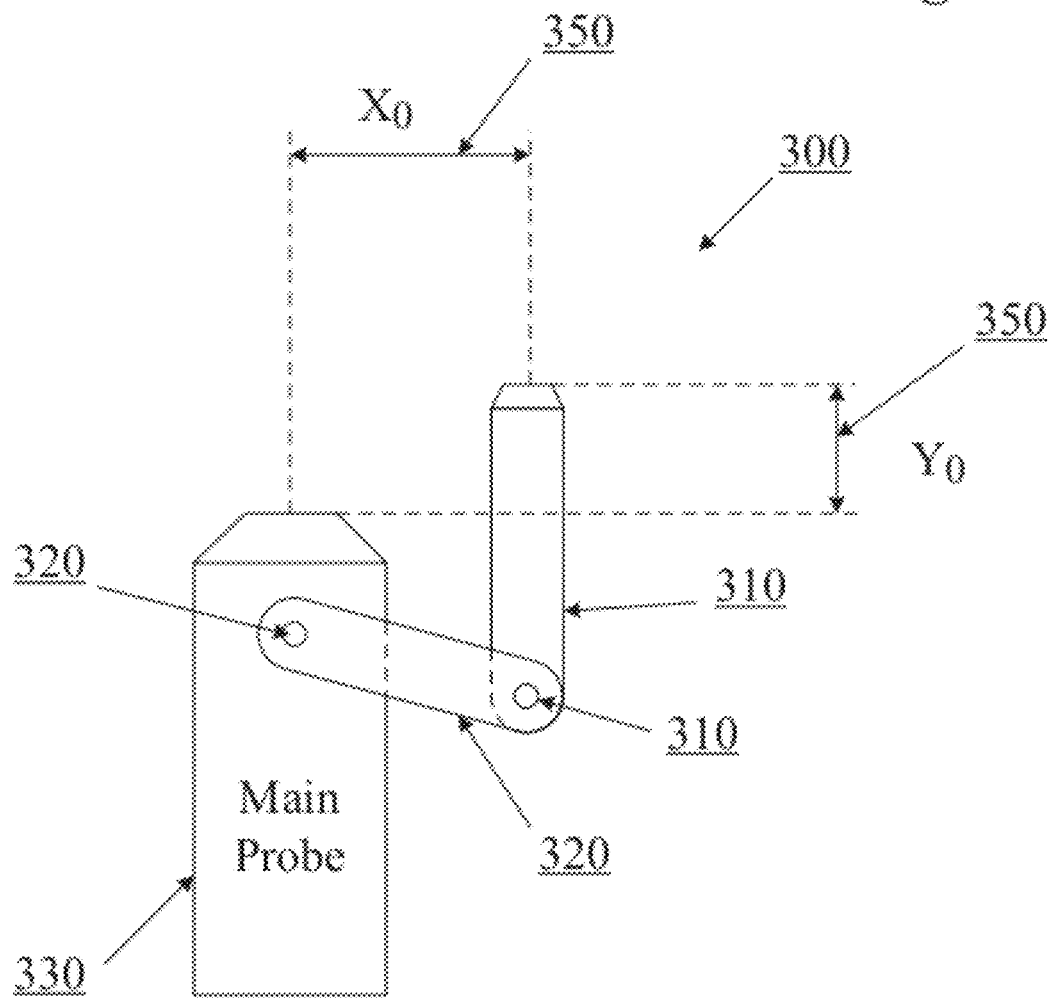
FIG. 3 is a schematic diagram showing a possible fixture for positioning an omni-directional probe relative to the main probe.
Figure 4:
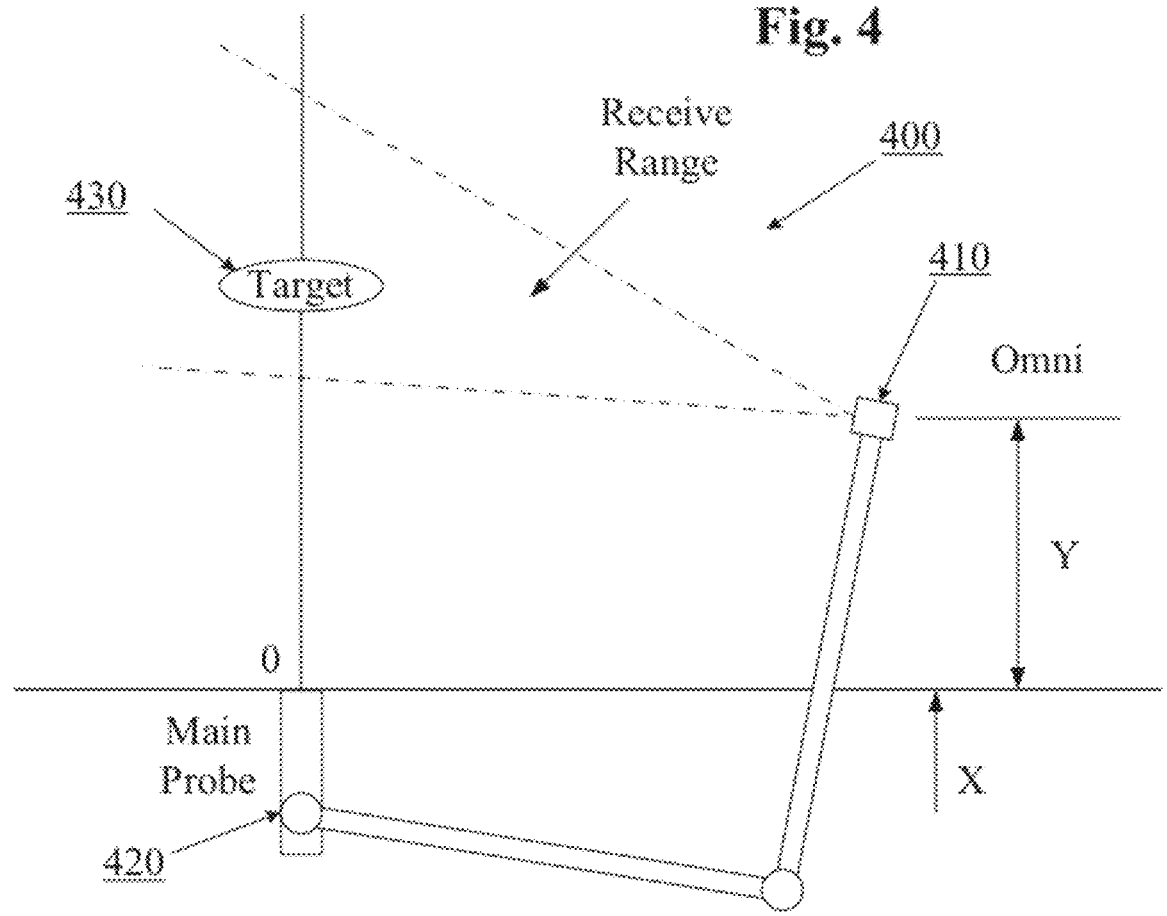
FIG. 4 is a schematic diagram showing a non-instrumented linkage for two probes.

The Multiple Aperture Ultrasonic Imaging methods described herein are dependent on a probe apparatus that allows the position of every element to be known and reports those positions to any new apparatus the probe becomes attached. FIGS. 3 and 4 demonstrate how a single omni-probe 310 or 410 can be attached to a main transducer (phased array or otherwise) so as to collect data, or conversely, to act as a transmitter where the main probe then becomes a receiver. In both of these embodiments the omni-probe is already aligned within the scan plan. Therefore, only the x and y positions 350 need be calculated and transmitted to the processor. It is also possible to construct a probe with the omni-probe out of the scan plane for better transverse focus.

An aspect of the omni-probe apparatus includes returning echoes from a separate relatively non-directional receive transducer 310 and 410 located away from the insonifying probe transmit transducer 320 and 420, and the non-directional receive transducer can be placed in a different acoustic window from the insonifying probe. The omni-directional probe can be designed to be sensitive to a wide field of view for this purpose.

The echoes detected at the omni-probe may be digitized and stored separately. If the echoes detected at the omni-probe (310 in FIGS. 3 and 410 in FIG. 4) are stored separately for every pulse from the insonifying transducer, it is surprising to note that the entire two-dimensional image can be formed from the information received by the one omni. Additional copies of the image can be formed by additional omnidirectional probes collecting data from the same set of insonifying pulses.

Figure 5:
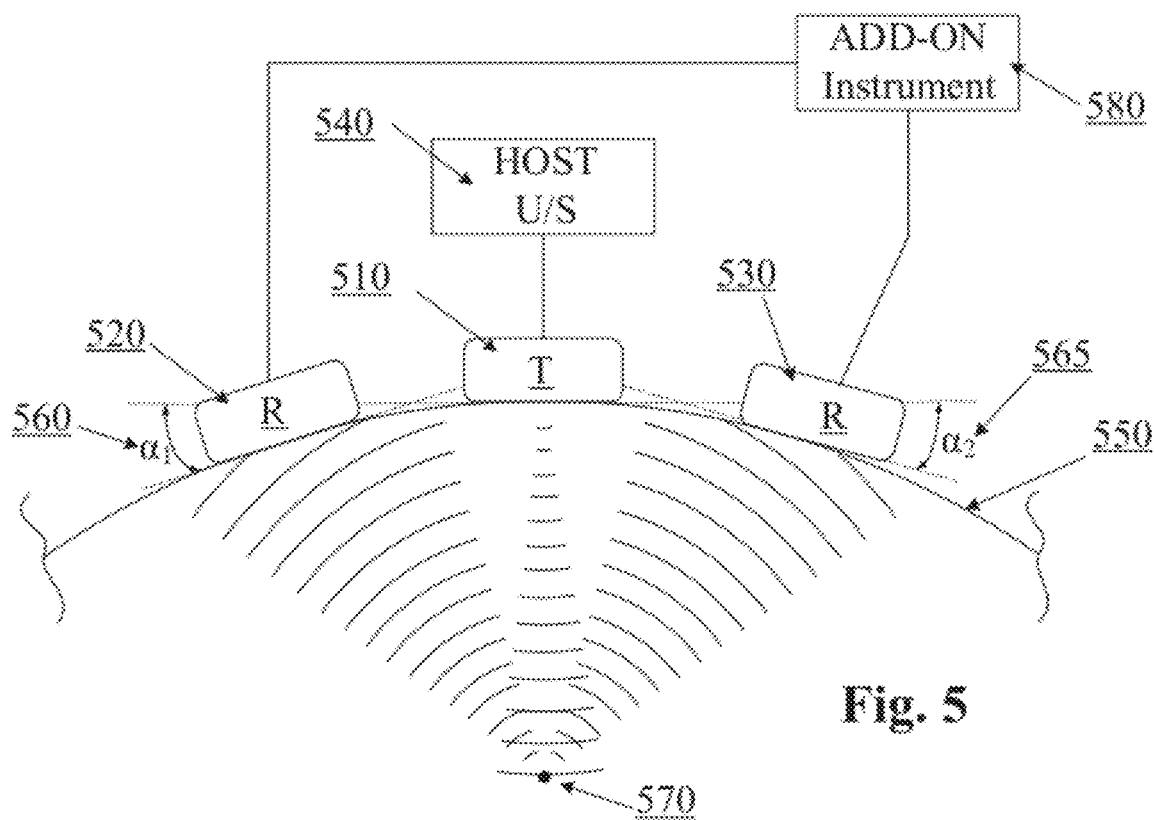
FIG. 5 is a block diagram of the transmit and receive functions where a three array Multiple Aperture Ultrasound Transducer and the associated MAUI electronics are used in conjunction with a host ultrasound machine. In this embodiment, the center probe is used for transmit only and mimics the normal operation of the host transmit probe.
Figure 5A:
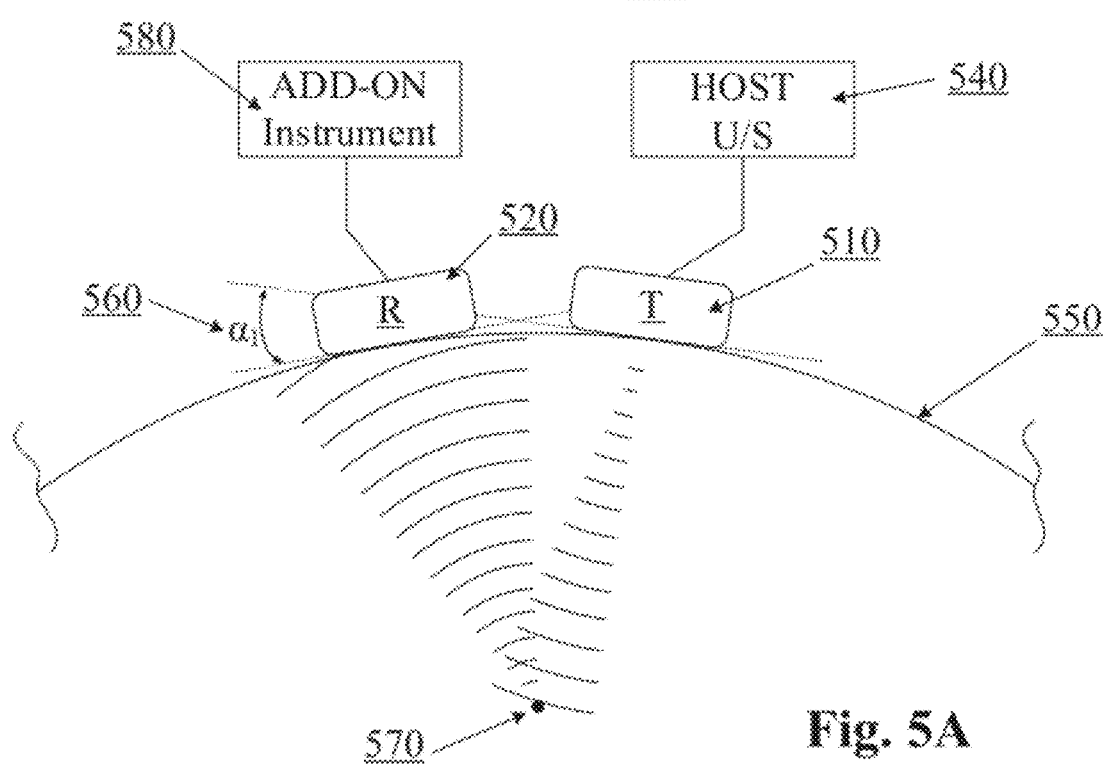
FIG. 5A is a block diagram of the transmit and receive functions where a two array Multiple Aperture Ultrasound Transducer and the associated MAUI electronics are used as an add-on to a host ultrasound machine, primarily for cardiac applications, with an add-on instrument. In this case, one probe is used for transmit only and mimics the normal operation of the host transmit probe, while the other probe operates only as a receiver.

In FIG. 5, the entire probe, when assembled together, is used as an add-on device. It is connected to both an add-on instrument or MAUI Electronics 580 and to any host ultrasound system 540. The center array 510 can be used for transmit only. The outrigger arrays 520 and 530 can be used for receive only and are illustrated here on top of the skin line 550. Reflected energy off of scatterer 570 can therefore only be received by the outrigger arrays 520 and 530. The angulation of the outboard arrays 520 and 530 are illustrated as angles $\alpha_1$ 560 or $\alpha_2$ 565. These angles can be varied to achieve optimum beamforming for different depths or fields of view. $\alpha_1$ and $\alpha_2$ are often the same for outboard arrays, however, there is no requirement to do so. The MAUI Electronics can analyze the angles and accommodate unsymmetrical configurations. FIG. 5A demonstrates the right transducer 510 being used to transmit, and the other transducer 520 is being used to receive.

Figure 6:
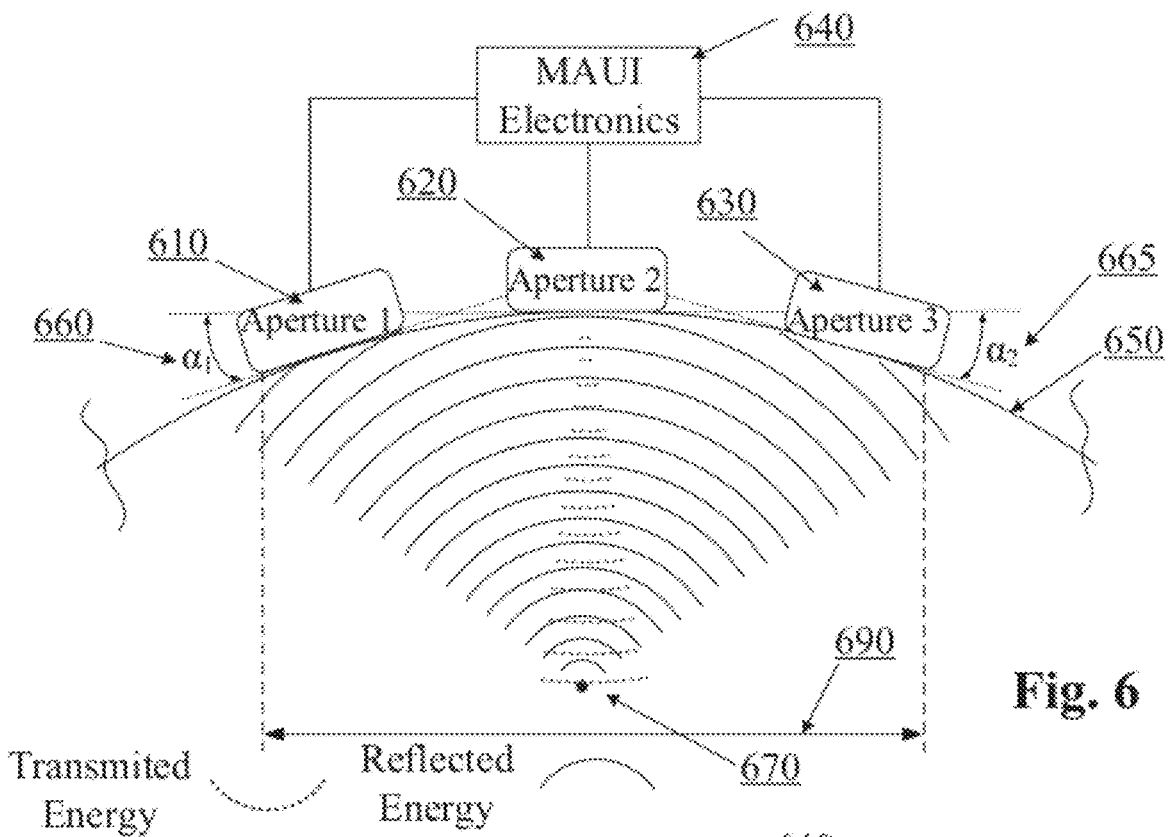
FIG. 6 is a block diagram of the transmit and receive functions where a Multiple Aperture Ultrasound Transducer is used in conjunction with only a Multiple Aperture Ultrasonic Imaging (MAUI) device. The stand-alone MAUI electronics control all elements on all apertures. Any element may be used as a transmitter or omni-receiver, or grouped into transmit and receive full apertures or even sub-arrays. In this figure the insonification emanates from the central aperture, aperture 2 of 3 apertures.

FIG. 6 is much like HG. 5, except the Multiple Aperture Ultrasound Imaging System (MAUI Electronics) 640 used with the probe is a stand-alone system with its own on-board transmitter (i.e., no host ultrasound system is used). This system may use any element on any transducer 610, 620, or 630 for transmit or receive. The angulation of the outboard arrays 610 and 630 is illustrated as angle $\alpha$ 660. This angle can be varied to achieve optimum beamforming for different depths or fields of view. The angle is often the same for outboard arrays; however, there is no requirement to do so. The MAUI Electronics will analyze the angle and accommodate unsymmetrical configurations.

Figure 6A:
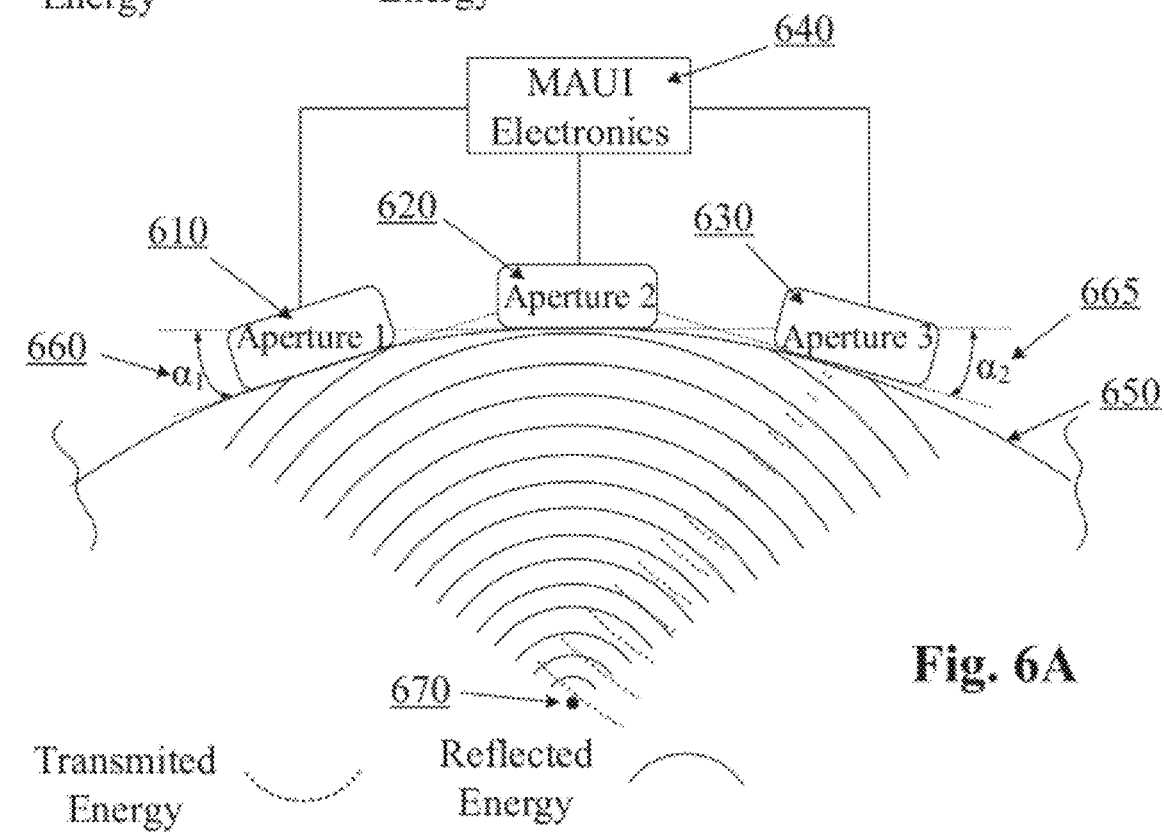
FIG. 6A depicts the insonification emanating from other than center aperture, in this figure Aperture 3 of 3.
Figure 6B:
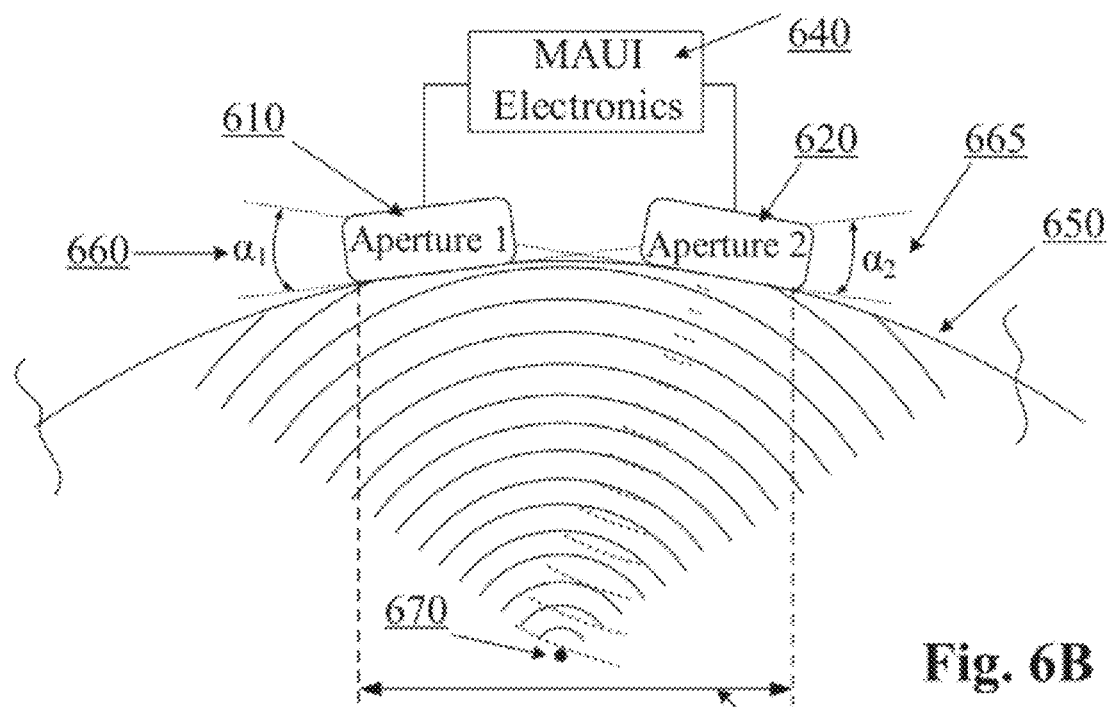
FIG. 6B is an illustration of two apertures being used a Multiple Aperture Ultrasound Transducer is used in conjunction with only a Multiple Aperture Ultrasonic Imaging (MAUI) device. In this figure the insonification emanates from aperture 2 of 2.

In this illustration, transmitted energy is coming from an element or small group of elements in Aperture 2 620 and reflected off of scatterer 670 to ail other elements in all the apertures. Therefore, the total width 690 of the received energy is extends from the outermost element of Aperture 1 610 to the outmost element of Aperture 2 630. FIG. 6A shows the right array 610 transmitting, and all three arrays 610, 620 and 630 receiving. FIG. 6B shows elements on the left array 610 transmitting, and elements on the right array 620 receiving. Using one transducer for transmit only has advantages with regard to a lack of distortion due to variation in fat layer. In a standalone system, transmit and/or receive elements can be mixed in both or all three apertures.

Figure 6C:
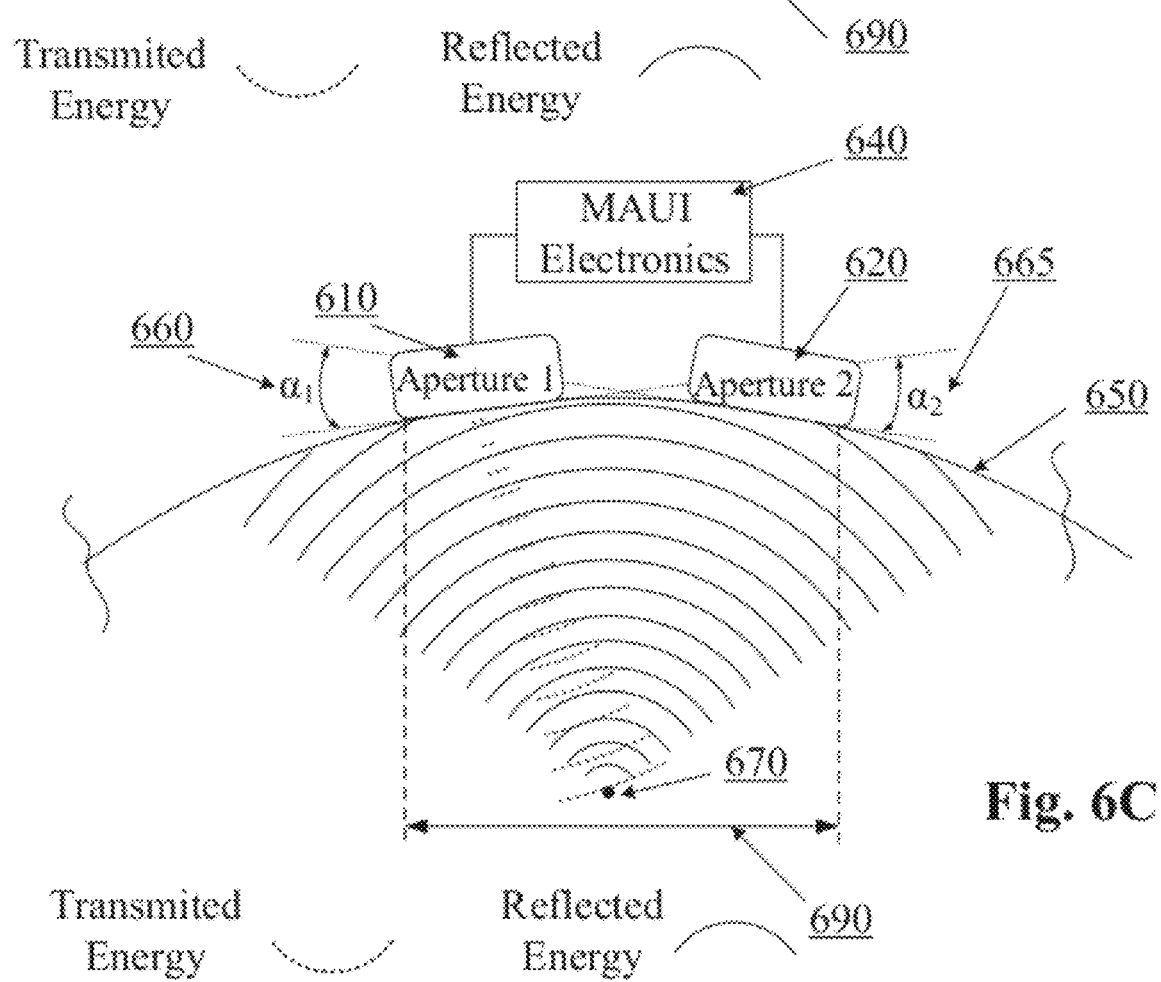
FIG. 6C is an illustration of two apertures being used a Multiple Aperture Ultrasound Transducer is used in conjunction with only a Multiple Aperture Ultrasonic Imaging (MAUI) device. In this figure the insonification emanates from aperture 1 of 2.

FIG. 6b is much like FIG. 5A, except the Multiple Aperture Ultrasound imaging System (MAUI Electronics) 640 used with the probe is a stand-alone system with its own on-board transmitter. This system may use any element on any array 610 or 620 for transmit or receive as is shown in FIG. 6C. As shown in either FIG. 6B or FIG. 6C, a transmitting array provides angle off from the target that adds to the collective aperture width 690 the same way two receive only transducers would contribute.

Figure 7A:
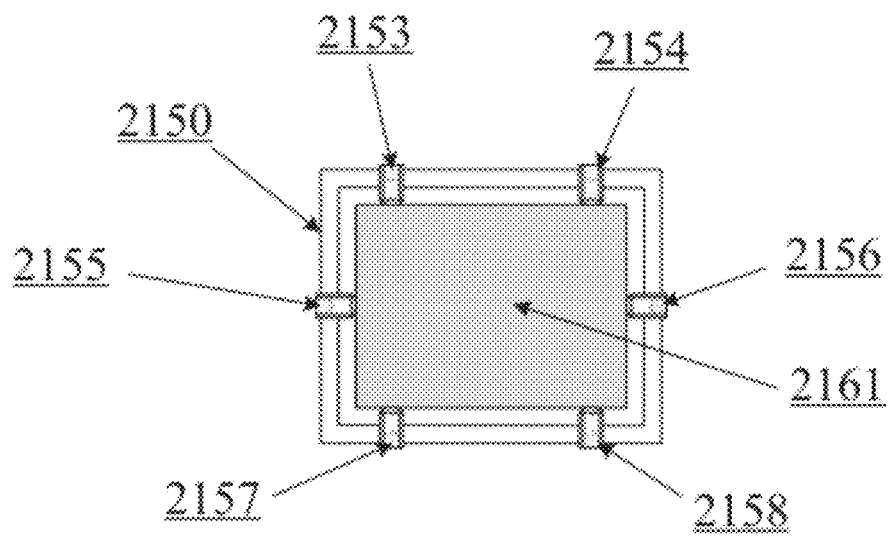
FIG. 7A is a top view of the precision array carrier with six adjustment screws and an array installed.
Figure 7B:
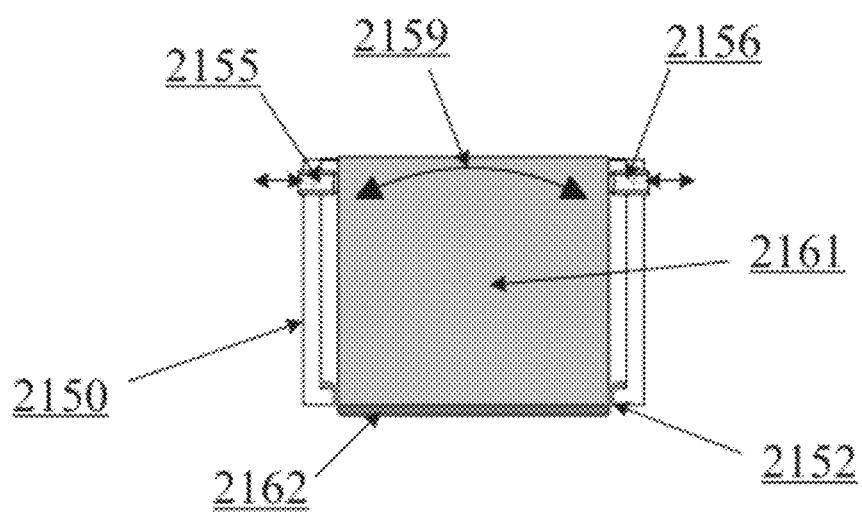
FIG. 7B is a side view showing the longitudinal axis adjustment of an array in the precision array carrier being supported by the array-centering gasket.
Figure 7C:
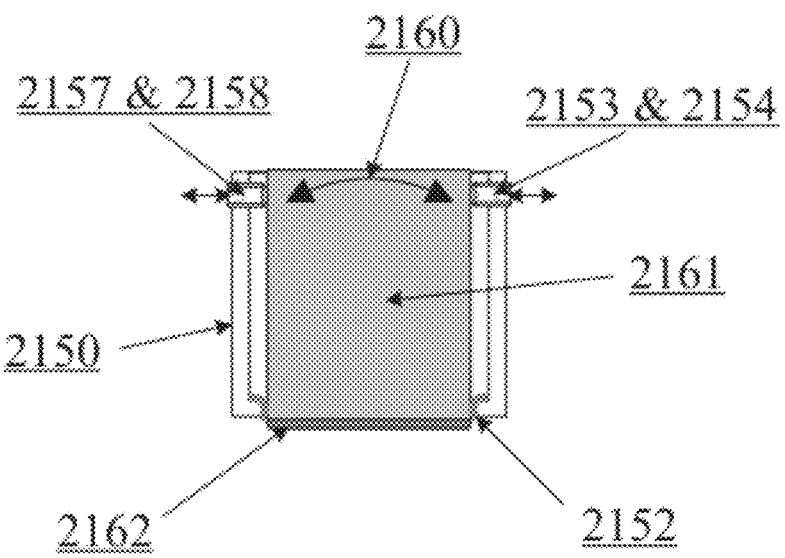
FIG. 7C is an end view showing the transverse axis adjustment of the array in the precision array carrier being supported by the array-centering gasket.

Some embodiments described herein include a precision carrier for the proper alignment of a universal multiple aperture ultrasound transducer. Referring to FIGS. 7A-7C, transducer array 2161 can be already "potted" in its own fixture 2161 with lens 2162 intact. Potting procedures are conventional methods to secure the transducer array to its lens and to the case. Flex circuitry, cabling, and attachment to the larger multiple aperture ultrasound transducer fixture can take place after the potting procedure is complete. A benefit of such embodiments is that they do not use the same transducers during the alignment. Different transducers with different "pots" can be utilized in any location of the alignment fixture thanks to the flexibility of the alignment carrier.

Figure 8A:
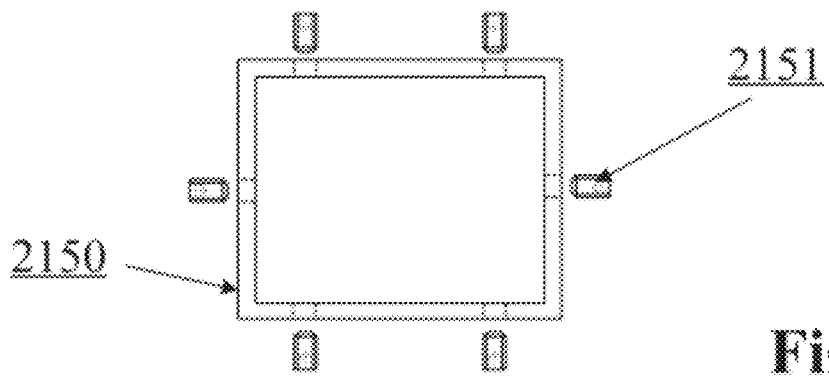
FIG. 8A is a top view of the precision array carrier.
Figure 8B:
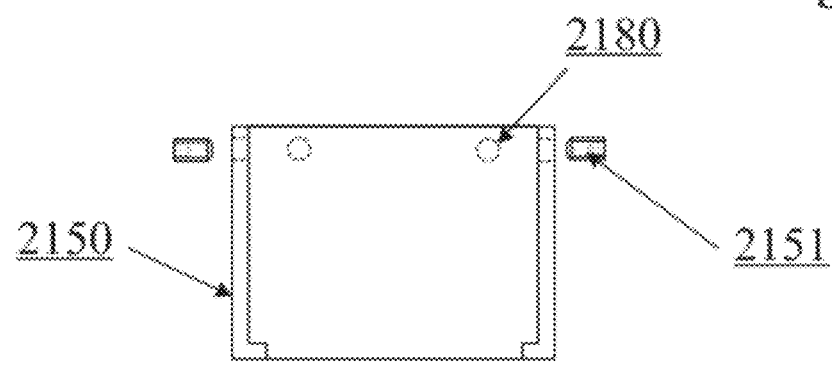
FIG. 8B is a side (longitudinal) view of the precision array carrier.
Figure 8C:
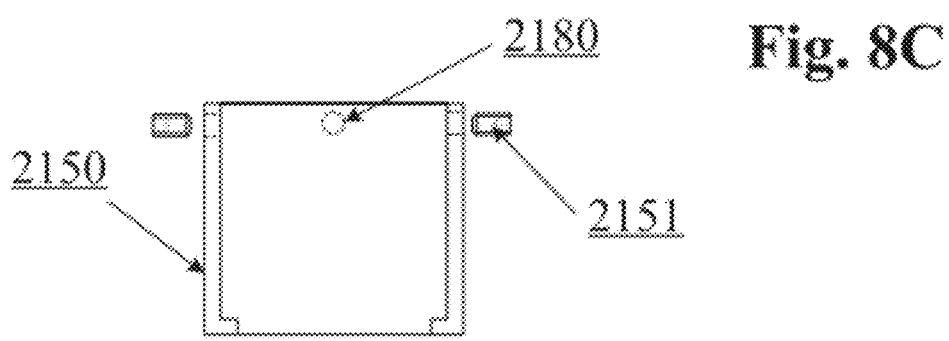
FIG. 8C is an end (lateral) view of the precision array carrier.

FIGS. 8A-8C provide views of the basic structure and features of embodiments of a precision carrier 2150 for a multiple aperture ultrasound transducer array. FIG. 8A shows a top view of a precision array carrier 2150 with six positioning screws 2151. FIG. 8B shows a side view of a precision array carrier 2150 having two threaded screw holes 2180 on each side. When positioning screws 2151 are inserted into threaded screw holes (e.g., screw holes 2155 and 2156 in FIG. 7B), adjustments may be made to employ longitudinal corrections 2159 to the "seated" array. FIG. 8C shows a side view of a precision carrier 2150 with threaded screw holes 2180 located on each end. When positioning screws are inserted into these threaded screw holes, adjustments may be made to employ lateral corrections 2160 to the "seated" array (as illustrated in FIG. 7C).

Figure 9A:
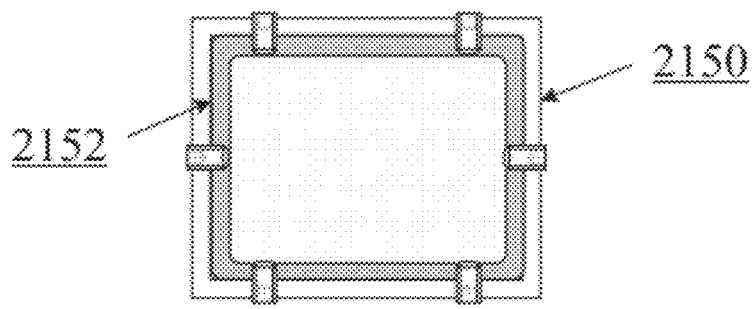
FIG. 9A is a top view of the precision array carrier with a centering gasket in place.
Figure 9B:
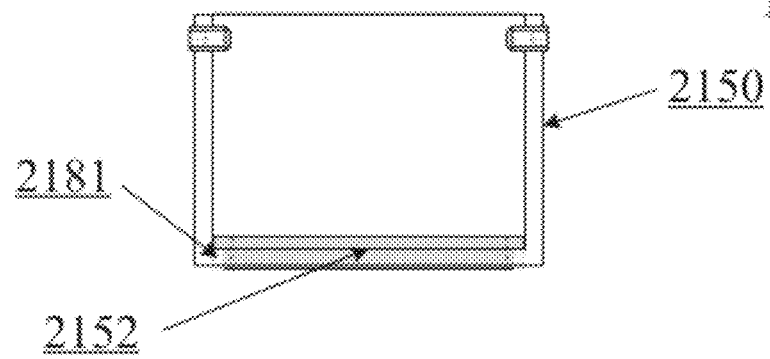
FIG. 9B is a side view (longitudinal) of the precision array carrier with a centering gasket in place.
Figure 9C:
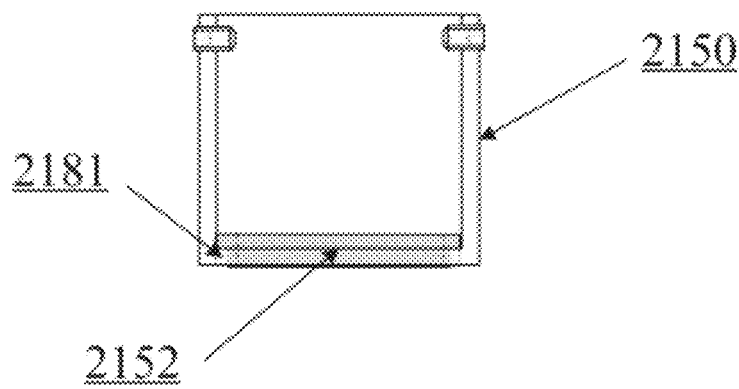
FIG. 9C is an end view (lateral) the precision array carrier with a centering gasket in place.
Figure 9D:
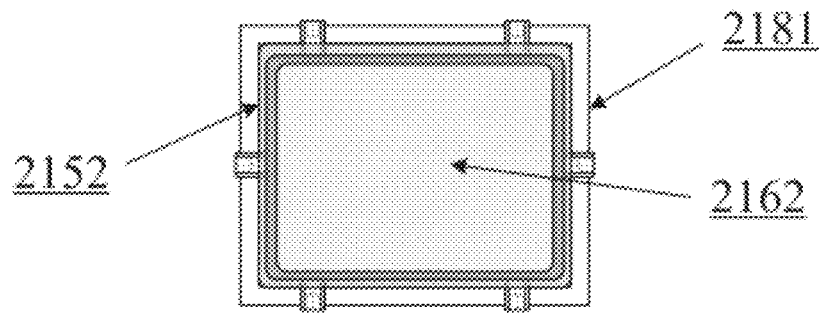
FIG. 9D is a bottom view of the precision array carrier with a centering gasket in place.

FIGS. 9A-9D show a precision array carrier 2150 with an array-centering gasket 2152 installed. FIG. 9A is a top view of the precision carrier 2150, with an array-centering gasket 2152 placed at the bottom of the carrier where the lens 2162 located in the center. FIGS. 9B-9D show side, end, and bottom views of the carrier, respectively. The array centering gasket 2152 can be located on the carrier's L shaped shoulder 2181, as illustrated in FIG. 9B. Further, as shown in FIG. 99, the gasket 2152 can extend the entire length of the carrier over the shaped shoulder 2181. The gasket 2152 can extend around the corners of the L shaped shoulder 2181 to cover the ends of the carrier as it illustrated in FIG. 9C. The gasket provides the array translational centering and a pivot point for positioning adjustments during operation without interfering with the integrity of the lens 2162. FIG. 9D provides a view of the lens 2162, the bottom of the precision carrier array centering gasket 2152, and finally the L shaped shoulder 2181.

Referring back to FIGS. 7A-7C, which show top, end, and side views, respectively of a precision array carrier 2150 with an array 2161 inserted therein. The array 2161 is supported end-to-end by positioning screws 2155 and 2156. The array can be supported from each side by positioning screws 2153, 2154, 2157, 2158 and from the bottom by the array centering gasket 2152. FIG. 7B shows the array 2161 in the precision array carrier 2150 being supported by array centering gasket 2152 and ready the longitudinal adjustment. Alternately tightening and loosening positioning screws 2155 and 2156 allows the array 2161 to be adjusted through arc 2159 to correct longitudinal axis errors. FIG. 7C shows the array 2161 in the precision array carrier 2150 supported by the array centering gasket 2152 ready for transverse alignment. Alternately adjusting positioning screw pairs 2157, 2158 and 2153, 2154 allow the array 2161 to be corrected for transverse axis errors.

Figure 10A:
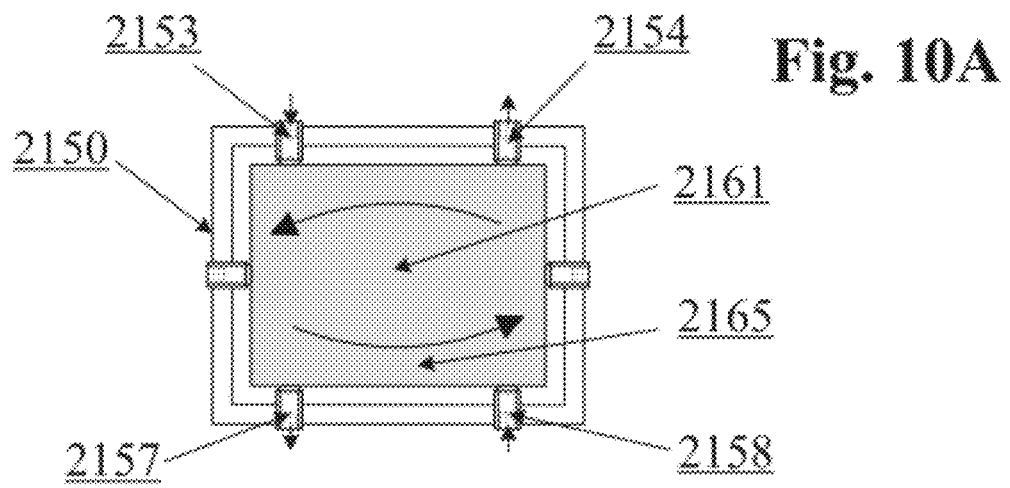
FIG. 10A is a top view of the array in the precision array carrier during a counter-clockwise rotational axis adjustment.
Figure 10B:
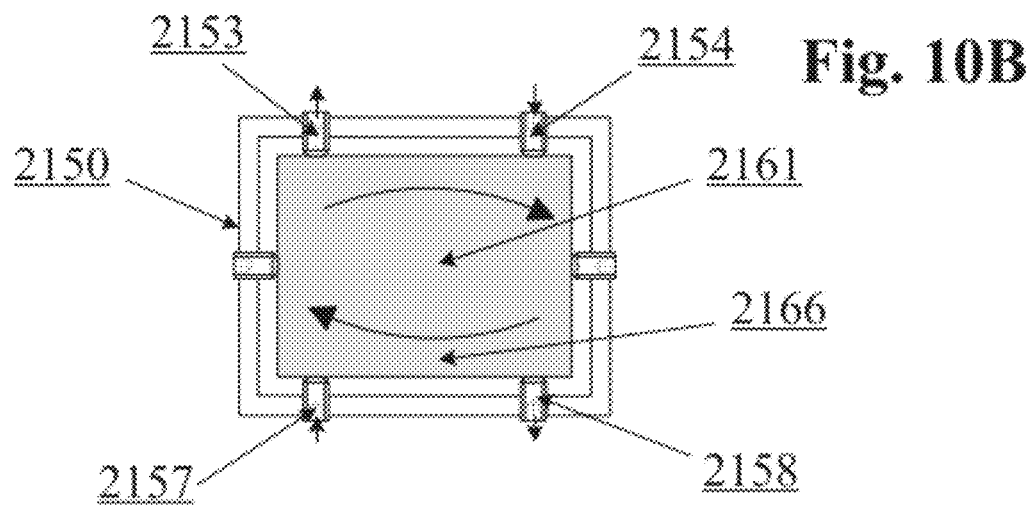
FIG. 10B is a top view of the array in the precision array carrier during a clockwise rotational axis adjustment.

FIGS. 10A and 10B show a top views of a precision array carrier 2150 with the array 2161 inserted. Arrows depict, respectively, counter-clockwise and clockwise rotational adjusting by way of selective screw adjustments. FIG. 10A shows a tightening of position screws 2153 and 2158 while loosening position screws 2154 and 2157 shifting the array 2161 in a counter-clockwise arc 2165 to correct rotational axis errors. FIG. 10B shows a tightening position of screws 2154 and 2157 while loosening position screws 2153 and 2158 to shift the array 2161 in a clockwise arc 2166 to correct rotational axis errors.

Figure 11:
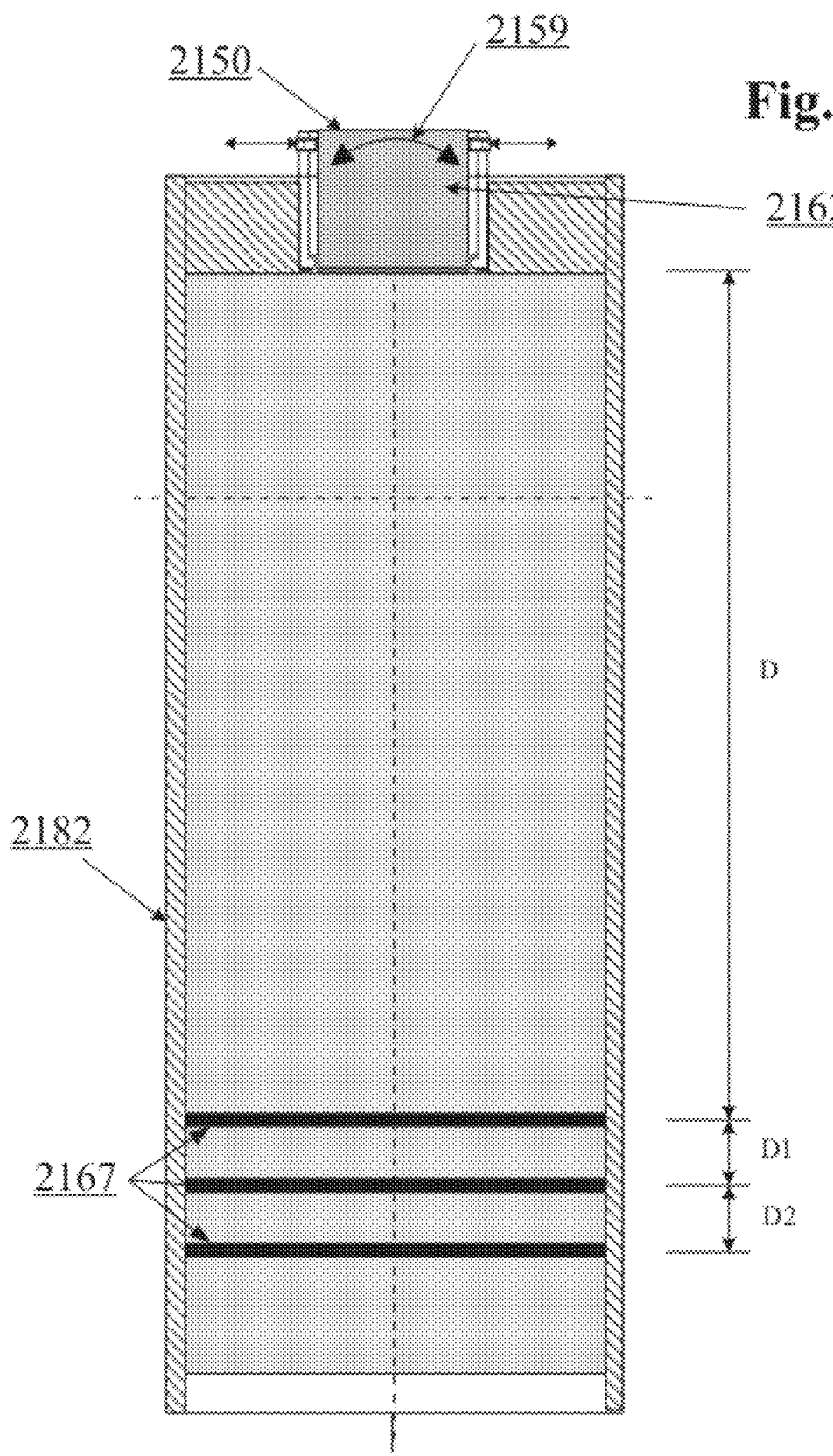
FIG. 11 shows an end view of a precision array carrier 2150 installed on a tissue equivalent phantom 2182 and ready to transmit and receive during alignment.

FIG. 11 shows an end view of a precision array carrier 2150 installed on a tissue equivalent phantom or test block 2182 and ready to transmit and receive during alignment. A 'phantom' is a structure filled with tissue equivalent material that has a speed of sound characteristics similar to that of human tissue with known voids and reflectors placed at known locations within the phantom. This end view of the phantom shows one embodiment including three targets 2167 in profile view. These targets can be echogenic, very reflective, or anechoic, void of reflection. The top target can be at a predetermined depth D from the surface of the phantom and the face of array carrier 2150. The other targets can be spaced at distances D 1 and D 2 from the top target. In some embodiments, the pre-determined depth D can be 100 mm from the top target to the face of the array. The other targets can have D 1 and D 2 distances of 10 mm, for example. However, any range of depths for the targets 2167 can be used, depending on the desired application of the transducer arrays. The perpendicular targets 2167 serve to assist during the longitudinal adjustment of the array positioning. When correctly positioned, the three targets would be displayed as exactly perpendicular to the front of the array, and further, each target 2167 would be displayed equidistantly one a top the other.

Figure 12:
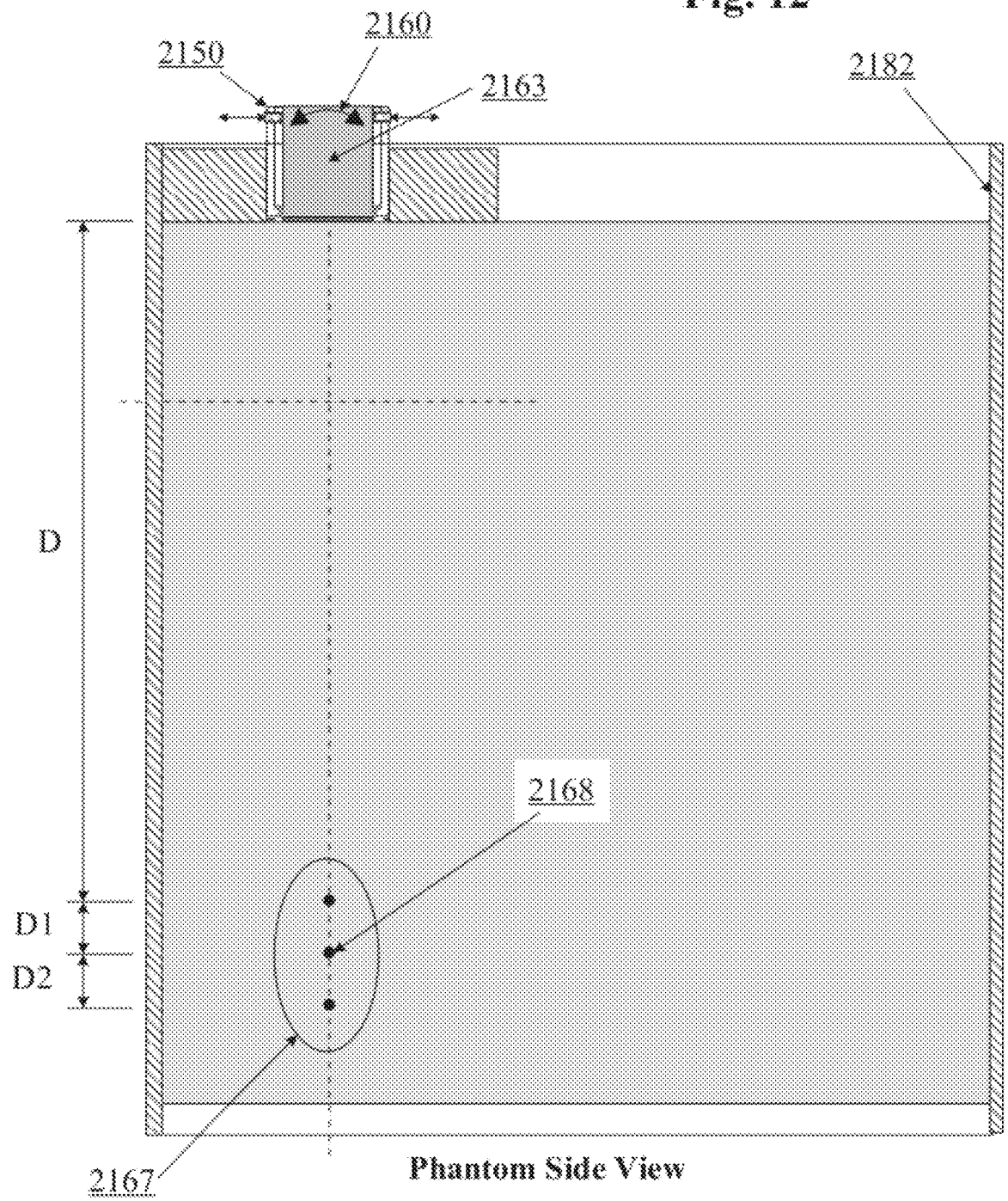
FIG. 12 shows a side view of the phantom 2182 with the ends of the targets 2167 visible.

FIG. 12 shows a side view of the phantom 2182 with the ends of the targets 2167 visible. Once transmitting and receiving, a lateral adjustment could be made to the array 2163 in the carrier 2150. The correct alignment is for achieved when all targets are visible above and below the center target 2168.

Figure 13A:
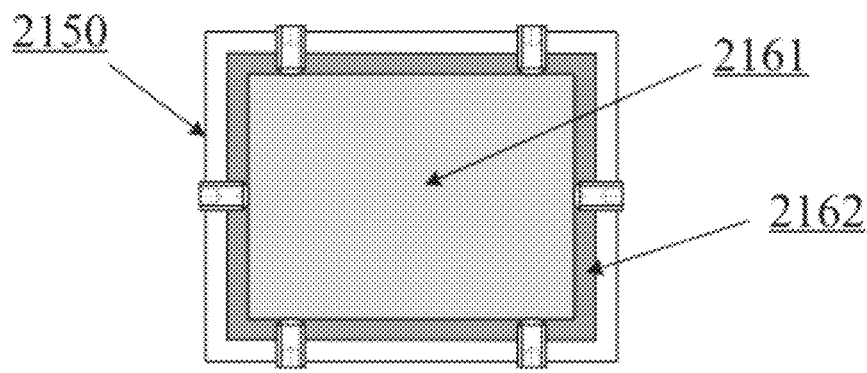
FIG. 13A is a top view of a carrier assembly with arrays installed (to become a precision carrier array assembly) and aligned within a precision transducer receptacle and stabilized with an acoustic damping material.
Figure 13B:
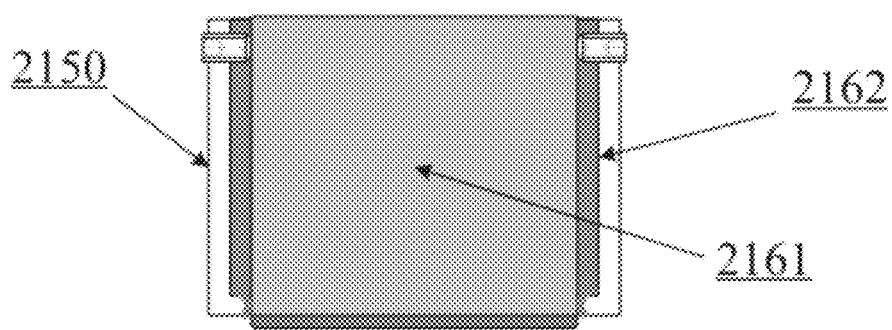
FIG. 13B is a side view of a precision array carrier with arrays installed (to become a precision carrier array assembly) and aligned within a precision transducer receptacle and stabilized with an acoustic damping material.
Figure 13C:
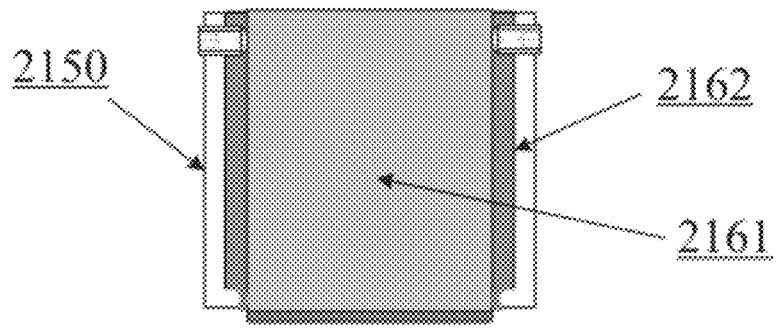
FIG. 13C is an end view of a precision carrier array with arrays installed (to become a precision carrier array assembly) and aligned within a precision transducer receptacle and stabilized with an acoustic damping material.

FIGS. 13A-13C show a precision array carrier 2150 with an array 2161 inserted and aligned, in top, side, and end views, respectively. At this stage an acoustic damping material 2162 can be poured into the gap between the array and the carrier to stabilize the position of arrays 2161. FIG. 13B is a side view of the precision array carrier 2150 showing the gap between the array 2161 and the precision array carrier 2150 filled with acoustic damping material 2162. FIG. 13C shows the gap between the array 2161 and the precision array carrier 2150 filled with acoustic damping material 2162.

Figure 14A:
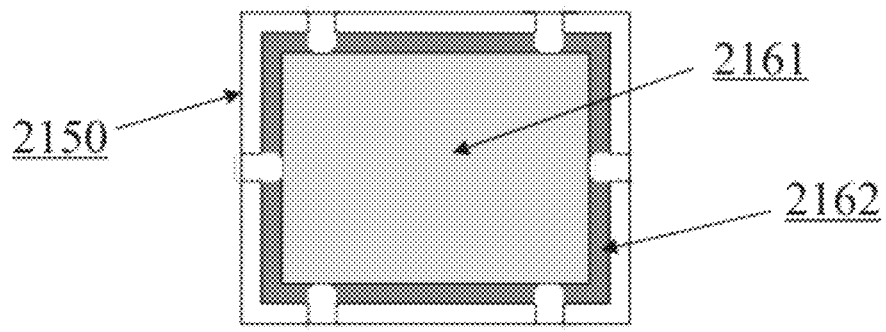
FIG. 14A is top view of a precision carrier array with arrays installed and aligned within a precision transducer head receptacle, the acoustic damping material has set and alignment screws have been removed.
Figure 14B:
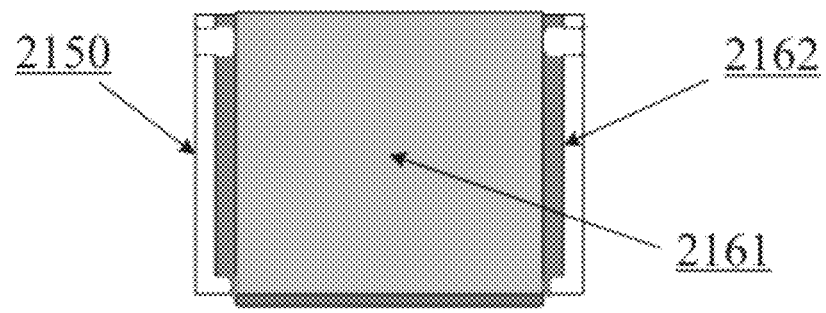
FIG. 14B is a side view of a precision carrier array assembly with arrays installed and aligned within a precision transducer head receptacle, the acoustic damping material has set and alignment screws have been removed.
Figure 14C:
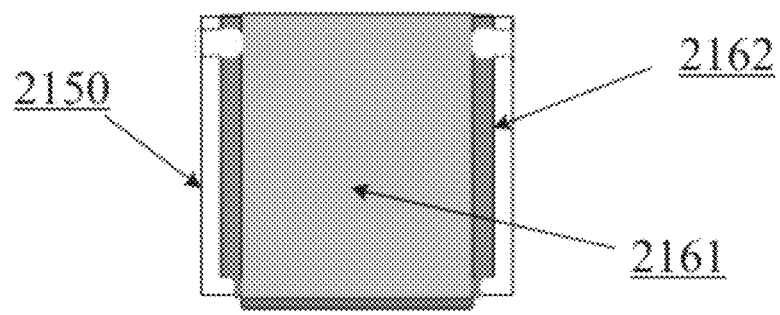
FIG. 14C is an end view of a precision carrier array with arrays installed and aligned within a precision transducer head receptacle, the acoustic damping material has set and alignment screws have been removed.

FIGS. 14A-14C show the precision array carrier 2150 with the array 2161 inserted and aligned in top, side, and end views, respectively. The acoustic damping material 2162 has cured and the six alignment screws have been removed. FIG. 14B is a side view of the precision array carrier 2150 with the array 2161 inserted, aligned, the acoustic damping material 2162 cured and the position alignment screws removed: At this point, the precision array carrier 2150 with its captured array becomes a precision carrier array assembly 2163.

Figure 15:
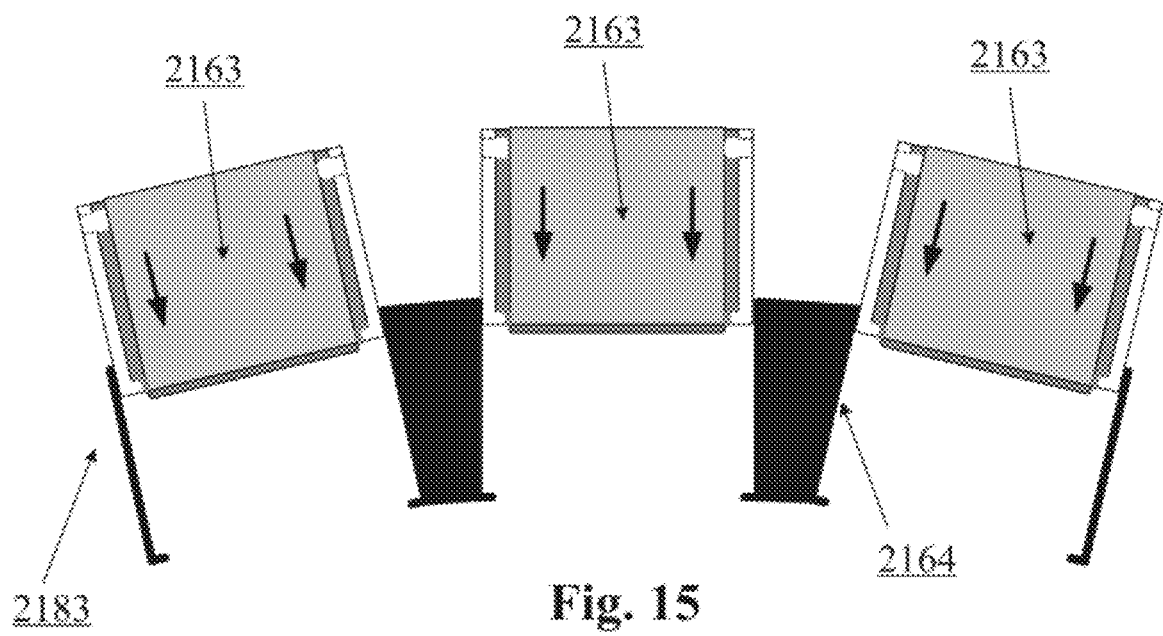
FIG. 15 shows a precision transducer receptacle or nose piece and three precision carrier array assemblies seated atop the transducer guides.

FIG. 15 shows a multi-aperture ultrasound probe assembly 2183 constructed with precision transducer receptacles surrounded by structural supports 2164. The structural supports 2164 can be constructed out of many hard materials (e.g. metals or plastics) and usually are built into a larger structure such as the probe 2200 in FIG. 22. In FIG. 15, the three precision carrier array assemblies 2163 are inserted into the precision transducer receptacles 2166.

Figure 16:
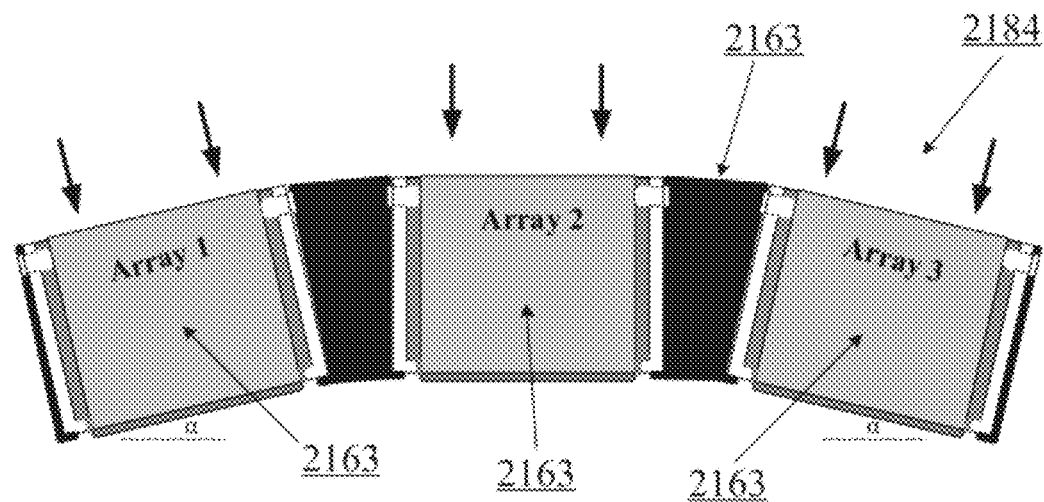
FIG. 16 shows the precision transducer receptacle or nose piece and three precision carrier array assemblies as in FIG. 22, and an ultrasound transducer array seated in each transducer guide of the nose piece.

FIG. 16 shows the multi-aperture probe assembly 2183 having precision transducer receptacles 2166 with the precision array assemblies 2163 each locked into the receptacles, thus completing the construction of the mufti-aperture ultrasound probe 2184 having three transducer arrays.

Figure 22:
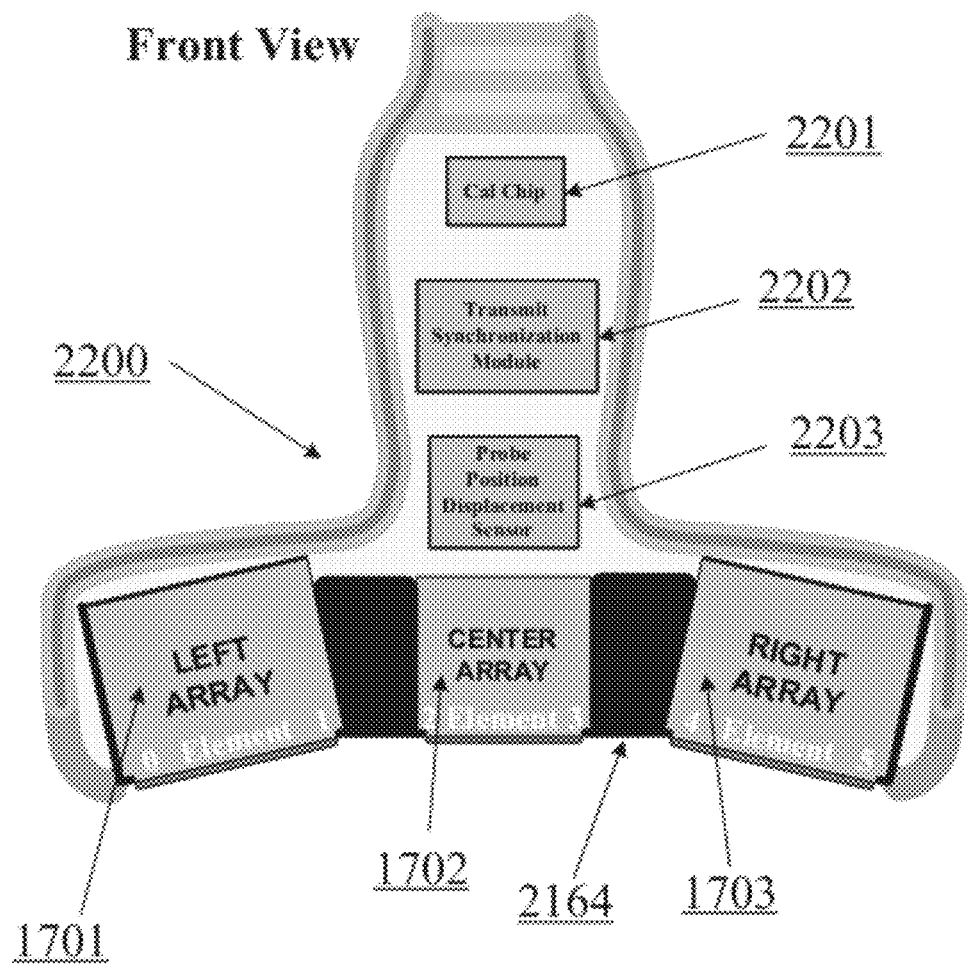
FIG. 22 illustrates a nose piece containing three separate arrays after it is installed into a Multiple Aperture Transducer. This figure includes the transducer specific calibration chip, the transmit synchronization module and probe position displacement sensor.

FIG. 22 shows a completed probe 2200 with arrays 1701, 1702, and 1703 fitted in array receptacles and ready for submission to the calibration cycle.

Alternative apparatus and methods for constructing and aligning multi-aperture ultrasound probes will now be discussed. Variations in the ultrasound beam displacement or rotation of both the insonifying and receiving probes about the x, y and z axes are preferably detected and corrected to achieve the best image quality. A MAUI alignment fixture for aligning a multi-aperture probe uses one or more precision angular alignment controls, precision stage assemblies that provide for the adjustment, in 6 degrees of freedom of the each array under test.

One factor in making multi-aperture imaging systems is the importance of precisely aligning the elements of the multiple arrays. It is well recognized that by increasing the effective aperture of a probe system by including more than one probe head and using the elements of all of the probes to render an image, the lateral resolution of the image can be greatly improved. In order to render an image, the relative positions of all of the elements are preferably known precisely. In some embodiments, if the probe system has position and rotation adjustments, a display is provided to position all of the elements to be in the same plane of scan and to transmit or receive in the same plane of scan.

Figure 17:
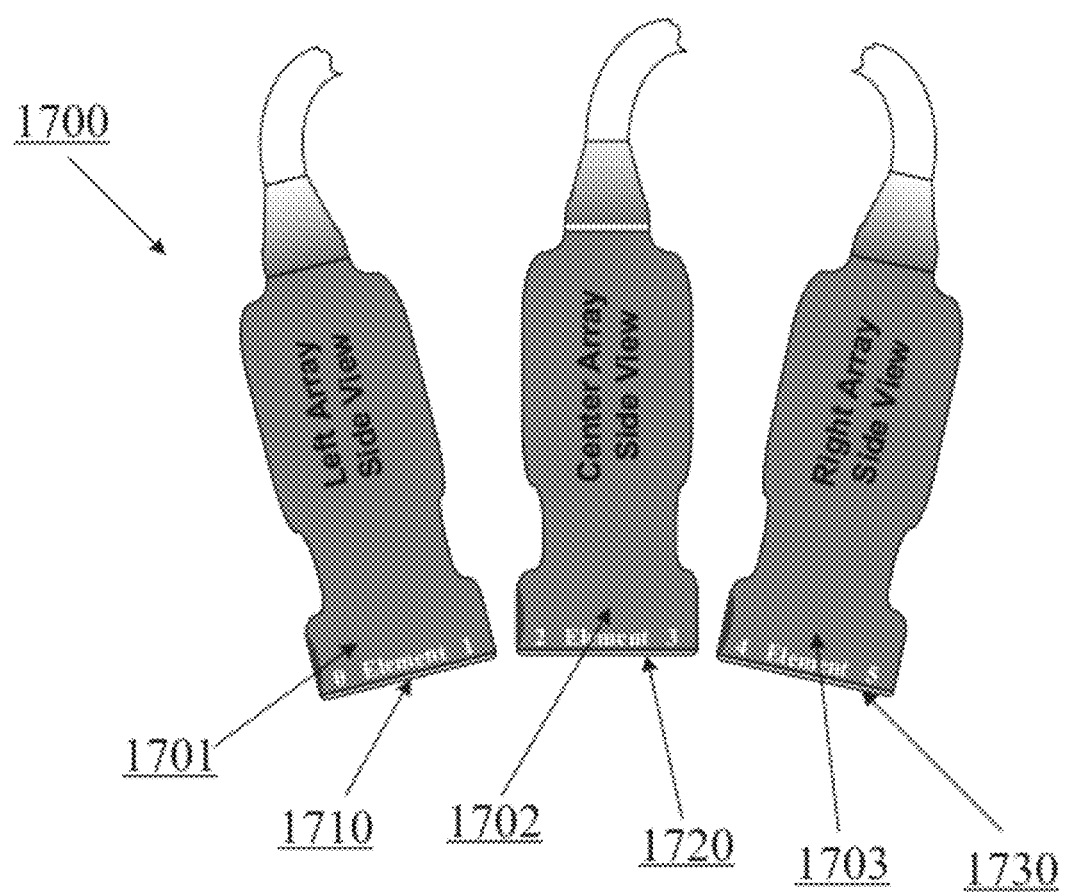
FIG. 17 is a drawing using three independent probes and their installed arrays or transducers. This illustration represents the positional nomenclature and array element numbering conventions.

FIG. 17 shows a probe system 1700 comprising three probes 1701, 1702, and 1703 working together as a multi-aperture transducer though not assembled in a single shell. This is not a standard embodiment of a multiple aperture transducer, but serves here to aid in describing arrays alignment. A multi-aperture transducer can comprise of any number of arrays 11710, 1720, 1730 (two or more), or even individual elements. For practical reasons, arrays in probes can easily be manufactured with a large number of elements and element spacing within a head can be well controlled. If one can precisely position the end elements of each probe, it is possible to imply the positions of the other elements. Therefore, a fixture will be described which finds the positions of the elements. This apparatus could determine the exact location of independent elements either inside or outside of an array; however, because arrays are typically constructed in a linear format, the embodiment discussed here only identifies the end elements.

In FIG. 17 these end elements are designated as element numbers 0 through 5, where 0 and 1 are the end elements of array 17110, 2 and 3 are the end elements of arrays 1720 and 4 and 5 are the end elements of array 1730. Any of the intermediate elements could be located in the same way as will be described.

Figure 18A:
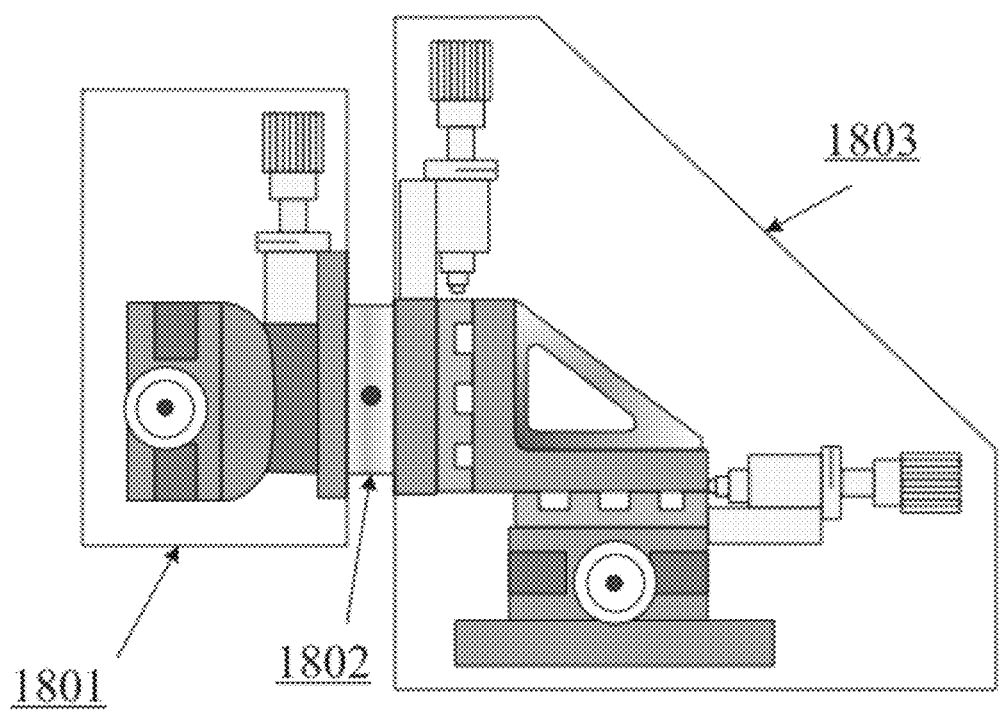
FIG. 18A shows the Precision Stage Assembly and sections that control movement in three different axes.
Figure 18B:
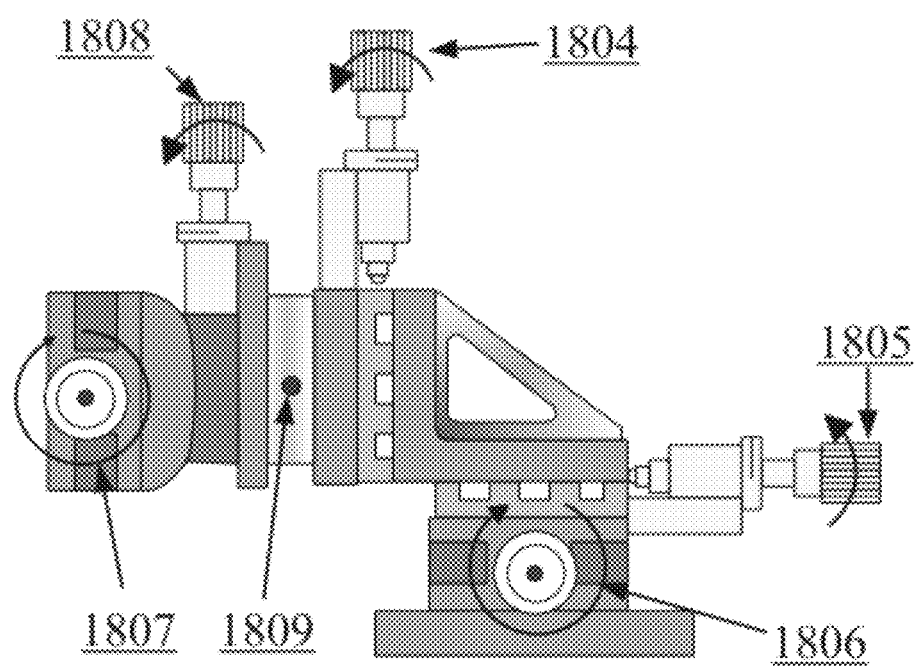
FIG. 18B shows the controls for the Precision Stage Assembly.

A precision alignment stage assembly is shown in FIG. 18A. The far left area of the assembly 1801 allows for the mechanical connection of a single probe, such as 1701 from FIG. 17. The precision alignment stage assembly has three separate mechanisms 1801, 1802 and 1803 that control the position of the attached array in x, y and z axes. Several alignment stage assemblies can be used in concert on that multiple probe arrays can be manipulated independently. FIG. 18B allows the operator to manipulate an array in any axis by using controls 1805, 1806, 1807, 1808, and bearing 1809. Precision screws 1804, 1805, 1806, 1807, and 1808 can be adjusted, and bearing 1809 can be rotated to affect one or more axes for the array during the alignment process.

Figure 25:
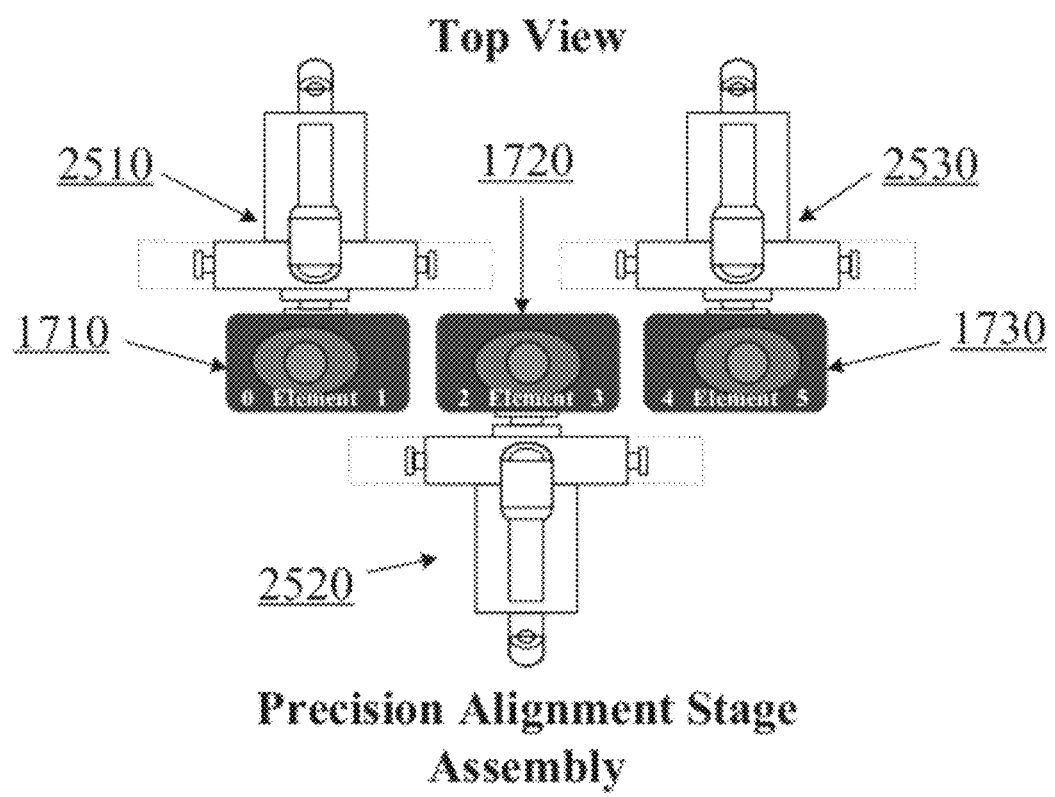
FIG. 25 is a representation using three arrays and three precision alignment stage assemblies showing their physical placement during testing.

FIG. 25 shows the arrays 1710, 1720 and 1730 attached in line to precision alignment stages 2510, 2520 and 2530. With the arrays set in place, they can now transmit to common points of interest and compare their points of impact with the other arrays.

As used herein, calibration of an ultrasound probe may involve determining the acoustic position of each individual ultrasound element in a probe with a desired degree of precision relative to some known coordinate system. The basic technique for aligning and calibrating a multiple aperture probe can be seen with reference to FIGS. 19A, 19 and 20.

FIG. 20 illustrates probes 1701, 1702 and 1703 from FIG. 17 now attached to alignment stage assemblies above a tank or test block 2012. The tank can be filled with any liquid, fluid, gel, solid, or other medium 2014 that is desirable for manufacture and safety considerations, as long as the speed of sound for the fluid is known. The tank can include a mounting location for the alignment stage assemblies. In some embodiments, as shown in FIG. 20, multiple alignment stage assemblies holding transducer elements can be mounted on the test block. From this position, it is possible to transmit ultrasonic pulses from the elements of any of the arrays to be received by ultrasonic sensor or hydrophones 2085 at the other end of the tank 2012.

As used herein, the term "hydrophone" is used in a generic sense and refers to any instrument capable of accurately receiving and transducing ultrasound waves into electronic signals. In some embodiments, hydrophones may also be used to transmit ultrasound signals. Thus, in some embodiments, hydrophones may comprise piezoelectric transducer arrays, or any other suitable technology. The term "hydrophone" is generally used herein to refer to ultrasound receiving and/or transmitting instruments attached to a calibration system, as distinct from the transducer elements and arrays of ultrasound imaging probes to be calibrated.

Figure 19A:
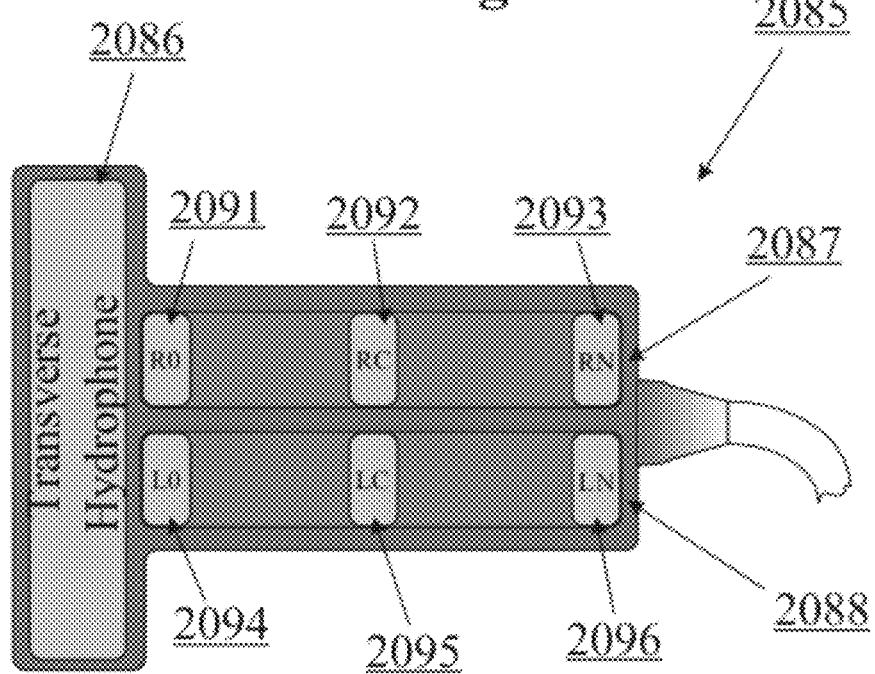
FIG. 19A depicts is an enclosure containing Right and Left Axial Hydrophones and a Transverse Hydrophone.
Figure 19B:
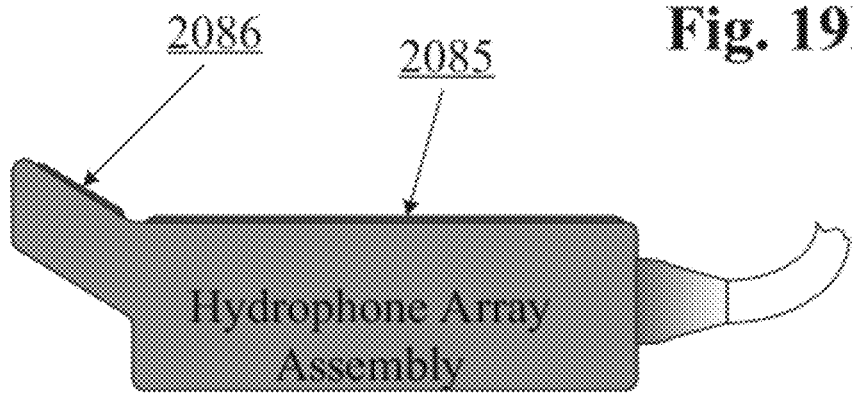
FIG. 19B depicts the dual Axial Hydrophones from the side and illustrates the angular orientation of the Transverse Hydrophone.

As shown in FIGS. 19A-19B, the hydrophone 2085 can be a multi-axis ultrasonic hydrophone 2085 configured to detect the X, Y and Z positions of each element of a single array or multiple arrays under test. The multi-axis hydrophone 2085 can include a transverse hydrophone 2086, and right and left hydrophones 2087 and 2088. The common targets for the probes 1701, 1702 and 1703 to shoot at are elements 2091, 2092 and 2093 on the right hydrophone 2087. On the left hydrophone 2088, elements 2094, 2095, and 2096 are the targets.

In use, the probe can be attached to a signal generator configured to excite any of the transducer elements to transmit ultrasonic pulses. An ultrasonic signal is transmitted which exhibits good autocorrelation properties (e.g., a tong frequency sweep, or 'chirp' waveform, a short (wideband) pulse, a spread spectrum waveform, etc) from at least one element in arrays 1710, 1720 and 1730. The transmitted ultrasound signal can travel through the test block and be received by the receiving hydrophone transducer elements 2091, 2092, 2093, 2094, 2095, 2096 and the transverse hydrophone 2086. It is important to note that detection of the ultrasonic signal or pulse as received by the hydrophone arrays cannot be detected accurately enough by cross correlation with the signal impressed on the probe element because the probe element itself distorts the signal.

Two innovative techniques are used to obtain the needed accuracy in finding the relative time delays and hence the relative distances. The first technique is to use cross correlation between the signal received at one element of the hydrophone (for example 2091) and the signal received at another element of the same hydrophone (for example 2093). The correlation peak will yield the time difference and thus the distance difference.

The second technique is to interpolate between samples of the received waveforms to obtain better time resolution than simply the sampling interval. Perhaps the best way to accomplish both of these tasks is to take the Fourier transform of both signals, fill in zeros for the high frequency components of a much larger transform. Call these larger transforms FFT 1 and FFT 2. Then find the peak of the inverse transform of (FFT 1*(conjugate of FFT 2)).

Figure 21A:
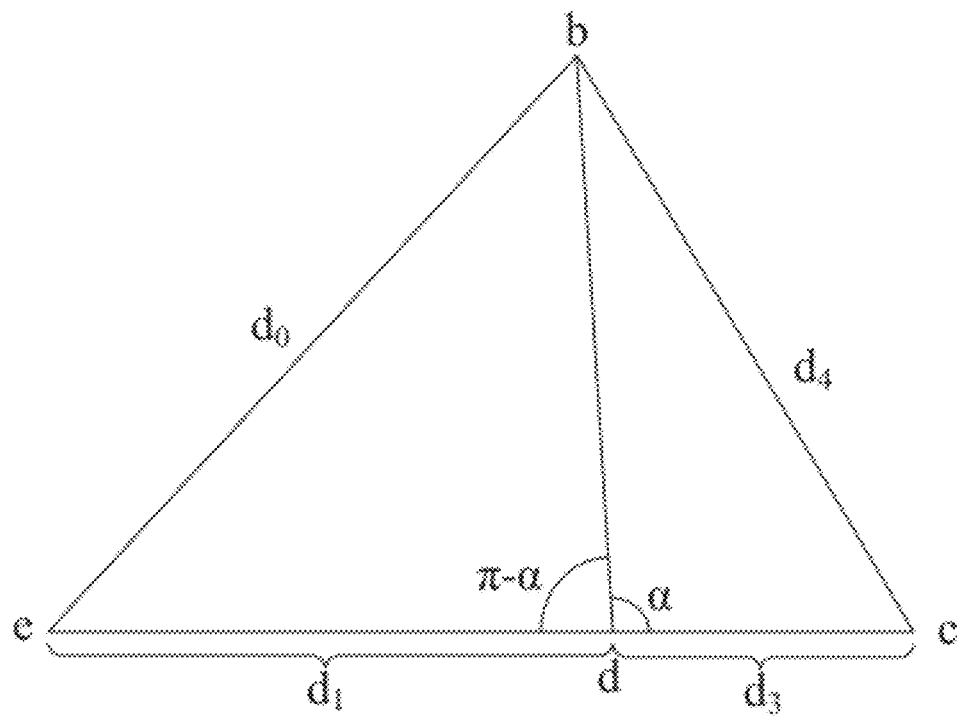
FIG. 21A is a graphic of basic geometry used to begin the conversion of distance difference into total distance.

A third technique may be used to convert differential distances to total distance. Consider the triangle bee in FIG. 21A where the point b represents one of the elements for which we need to compute a position, and c and e are known reference points in the bottom of the water tank. The distance $d_4$ represents a total distance between the test element at point b and the hydrophone element at point c (840 or 870). Similarly, the distance $d_0$ represents a total distance between the test element at point b and the hydrophone element at point e (820 or 850). It is desired to measure the lengths $d_4$ and $d_0$ by triangulation, but just knowing the difference between $d_0$ and $d_4$ is not enough. By adding a transverse hydrophone (see 2086 In FIG. 19A) in the bottom of the tank we have two triangles from which we can compute $d_0$ and $d_4$. Let e, d, and c be the locations of the hydrophones 2094, 2095 and 2096 or 2091, 2092 and 2093 of FIG. 19A.

For the following analysis, the hydrophones 2094, 2095 and 2096 are preferably on the same line and on a parallel line to that formed by 2091, 2092 and 2093. The distance between 2094 and 2095 is designated $d_1$, and the distance between 2095 and 2096 is designated $d_3$. $d_1$ and $d_3$ are preferably known precisely as this becomes the reference "yardstick" for the other measurements, 2095 should be roughly centered between 2094 and 2096 LN, but $d_1$ does not need to equal $d_3$. The same is true for R0, RC, and RN.

Let d 2 be the reference distance and define measured distances as:

$$d_2m = d_2 - d_2 = 0$$

$$d_0m = d_0 - d_2$$

$$d_4m = d_4 - d_2$$

From the law of cosines we have $$d_4^2 = d_2^2 + d_3^2 - 2d_3d_2 \cos \alpha$$

$$d_0^2 = d_2^2 + d_1^2 - 2d_1d_2 \cos(\pi - \alpha) = d_2^2 + d_1^2 + 2d_1d_2 \cos \alpha$$

$$\cos \alpha = (d_4^2 - d_2^2 - d_3^2)/(-2d_3d_2) = (d_0^2 - d_2^2 - d_1^2)/(2d_1d_2)$$

$$d_4^2 - d_2^2 - d_3^2 = -(d_0^2 - d_2^2 - d_1^2)d_3/d_1$$

$$(d_4m + d_2)^2 - d_2^2 - d_3^2 + (d_0m + d_2)^2 d_3/d_1 - d_2^2 d_3/d_1 - d_1 d_3 = 0$$

Combining and canceling terms this becomes $$d_2 = (-d_4m^2 + d_3^2 - d_{0m}^2 d_3/d_1 + d_1 d_3)/(2d_4m + 2d_0m d_3/d_1)$$

Then $d_0 = d_{0m} + d_2$ and $d_4 = d_{4m} + d_2$.

Thus we have the full measurements from received differential times.

Two parallel "yardsticks" or right and left hydrophones are provided in the bottom of the tank in order to measure position along the z axis (i.e. the axis perpendicular to the scan plane), as illustrated in FIG. 23B. It will be the goal to position all of the probe elements from all three arrays 1701, 1702 and 1703 in a line midway between the two yardsticks using the various controls illustrated in FIG. 18B.

Figure 21B:
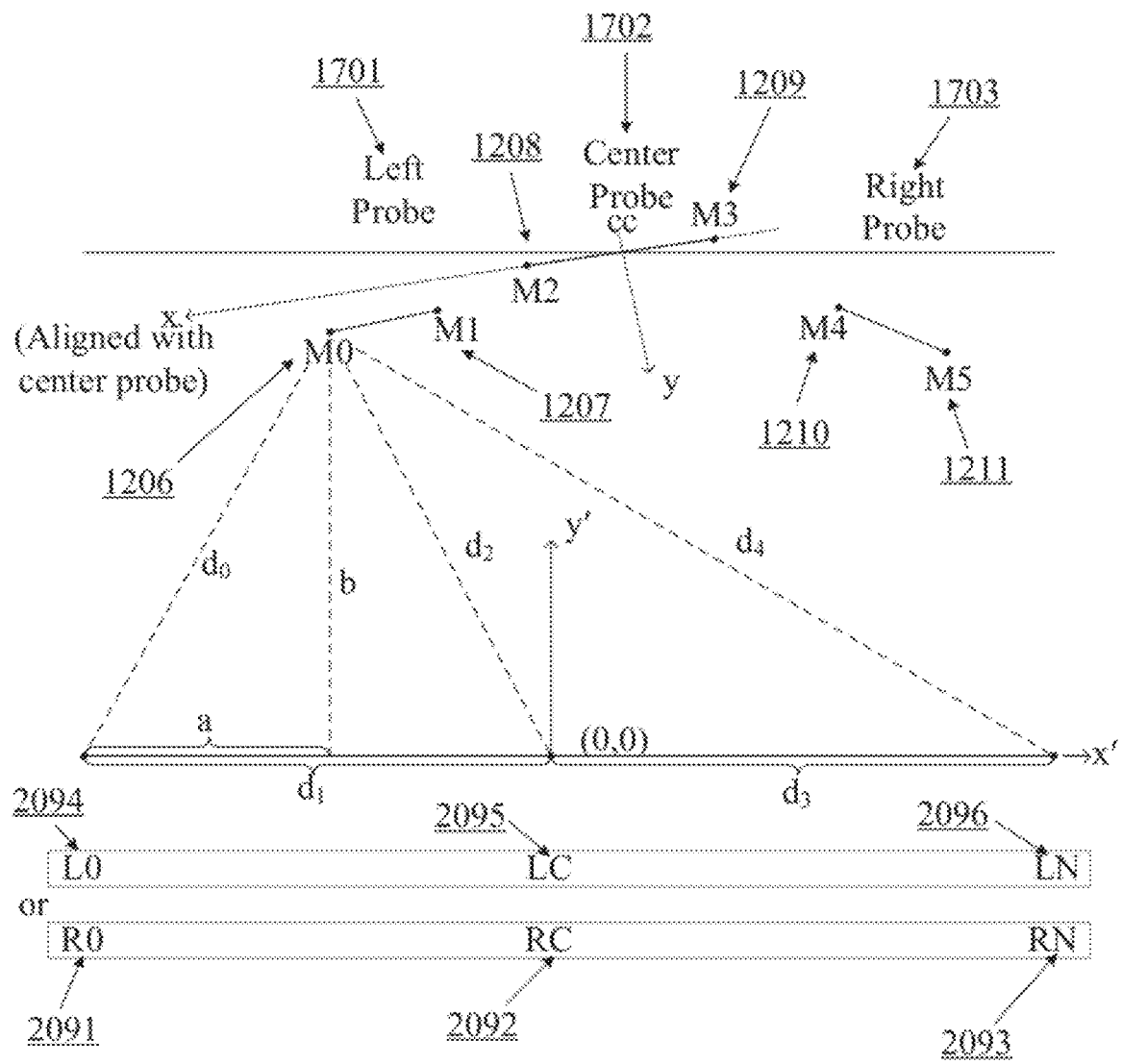
FIG. 21B is a graphic of the detailed geometry used to begin the conversion of distance difference into total distance allowing for the precision location of array element using three hydrophones.

Referring now to FIG. 21B, consider the measurement of the position of any probe element such as M0 1206. First, consider using the right yardstick R 0-RC-RN 2091, 2092, 2093. By transmitting a chirp signal from element M 0 1206 and receiving it on hydrophones at R0, RC, and RN 2091, 2092 and 2093, one can calculate the differential times for transmission along the paths $d_0$, $d_2$, and $d_4$. Times can be converted to distances if the speed of ultrasound of the test block medium is known. If the test block medium is water, the speed of sound is approximately
sos=1.40238742+5.03821344*TE/1000.−5.80539349*TE^2/100000.+3.32000870*TE^3/10000000.−1.445.37900*TE^4/1000000000.+2.99402365*TE^5/1000000000000 in mm per microsecond where TE is the temperature in degrees Celsius. Differential distances can be converted to total distances according to the derivation above.

Now from trigonometry, distance $a=(d_0^2-d_4^2+(d_1+d_3)^2)/(2(d_1+d_3))$

The position along the x' axis is $d_1-a$.

Assuming that the element is midway between the two yardsticks, then the position along the y' axis is sqrt $((d_0^2-a^2-(zr/2)^2))$.

Initially considerable error may occur as a result of this assumption, but the measurement of z allow for adjustment of the element or the entire probe assembly until this assumption is satisfied.

Again referring to FIG. 21B, the same computations for x' and y' can be made using the left hydrophone array 2094, 2095 and 2095. In some embodiments, the results of the measurements made with the right hydrophone array may be averaged with results of measurements made with the left hydrophone array.

Advantageously, by having two hydrophone arrays or "yardsticks," the z axis can be measured, i.e., the position of the elements in or out of the scan plane. Then the array alignment apparatus can display it (see FIG. 22A, 2300), and thus allow either manual (FIG. 18B) or automatic (FIG. 24) correction and alignment. The z variable is related to the time of arrival difference of the pulse as received at RC 2092 and LC 2095. The probe position should be adjusted until the time difference is close to zero. When this is done, all of the x and y measurements will be accurate and the relative positions of all of the elements will be known.

In some embodiments, the right and left hydrophone arrays may be used to measure an acoustic position of a test element along the z axis; i.e., the test element's position in or out of the scan plane. In some embodiments, following such a measurement the calibration system may display and/or automatically correct an alignment of the probe within the docking area of the calibration system. In other embodiments, the calibration system may direct an operator to manually adjust an alignment of the probe.

Figure 34A:
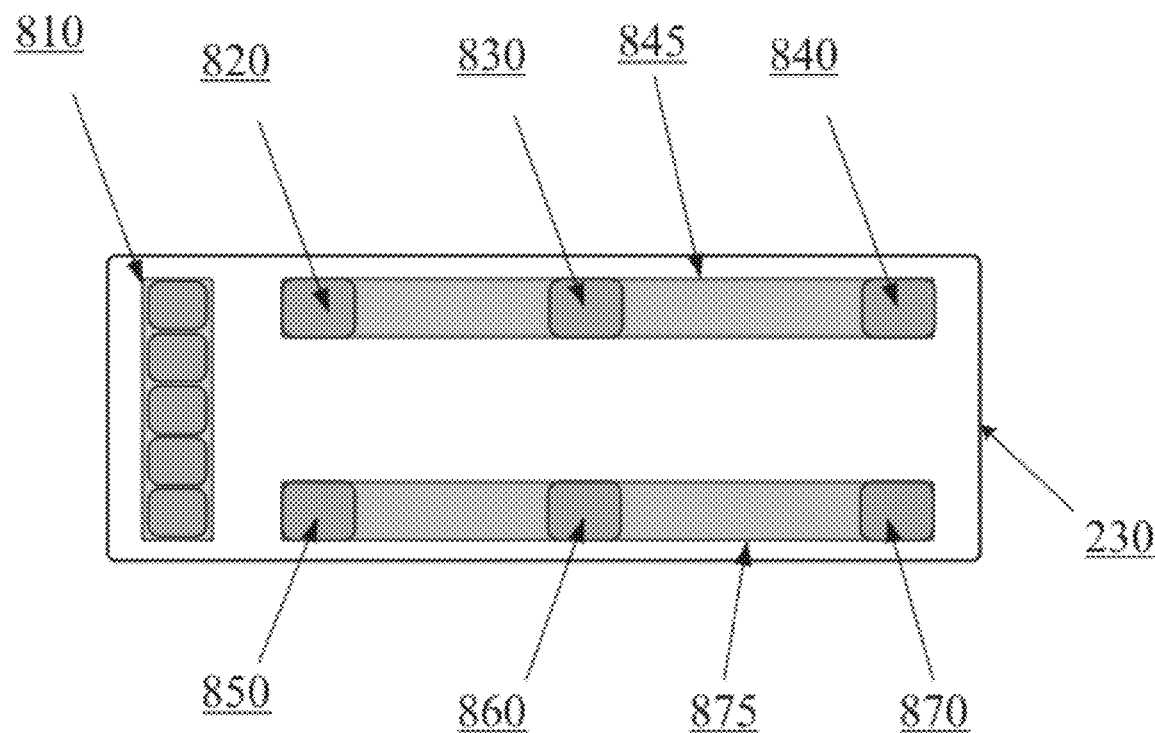
FIG. 34A is a plan view illustration of one embodiment of a hydrophone matrix which may be located at a bottom of a calibration system.

The z variable may be proportional to the distance d2 as computed from the hydrophones on track 845 minus the distance d2 as computed from the hydrophones on track 875 in FIG. 34A. In some embodiments, the probe position may be adjusted until this difference is close to zero.

In other embodiments in which the probe element cannot be mechanically centered between the two tracks, the z position can be computed. This is particularly true for 1.5D probes and 2D probes where it is not possible to position all elements simultaneously to a central position. In these cases, the acoustic position of elements along the z axis may be stored in the calibration table along with x and y coordinates as discussed above.

Figure 21C:
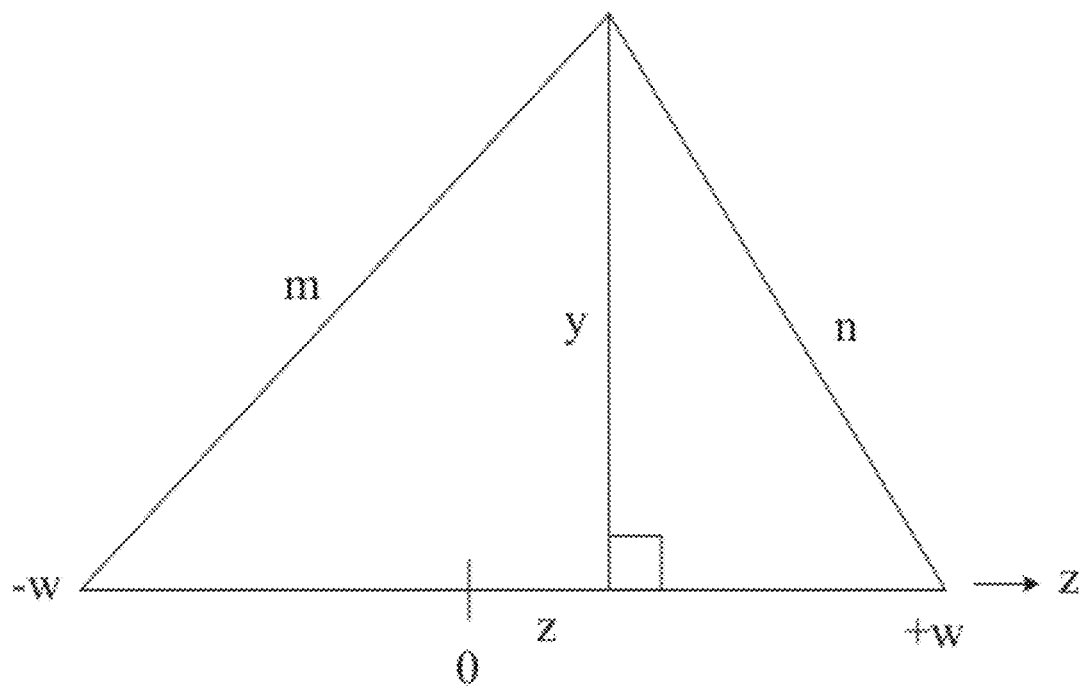
FIG. 21C is a graphic of geometry used to compute the z position of an element.

The value of z can be computed through a straightforward trigonometric calculation as illustrated in FIG. 21C.

Let m=the distance d2 as computed from the hydrophones on track 845 and let n=the distance d2 as computed from the hydrophones on track 875.

Let w indicate half the known distance between the two tracks.

$n2=(w-z)2+y2$ $m2=(w+z)2+y2$ then $n2=(w-z)2+m2-(w+z)2$ and $z=(m2-n2)/4w.$

In some embodiments, the transverse hydrophone array may be used to determine an angular displacement of a probe test element. In some embodiments, such information may be used to direct automatic or manual re-positioning of the probe. In alternative embodiments, such information may be incorporated into stored calibration data.

In some embodiments, a controller, such as a computer, can scan and find the maximum signal strength on the transverse hydrophone 2086 and record the angular displacement for the probe element.

To use the multiple aperture array alignment apparatus as a daily calibrator, multiple aperture ultrasound transducers may already be fully assembled, such as the embodiment illustrated in FIG. 22. Therefore, all of these measurements will preferably be referenced to axes on the probe assembly. In the multi-aperture transducer probe assembly 2200 shown in FIG. 22, it would be reasonable to rotate and translate measurements to a new coordinate system (x,y) centered on the center array. The appropriate coordinate system would be dependent on the ultrasound imaging system for which the probe assembly would be used. The multi-aperture probe can have a resident calibration memory or cal chip 2201 that can be programmed with calibration data received from the automated precision stage assembly, described below.

The transmit synchronization module 2202 is not related to calibration, but may be used to identify the start of pulse when the probe is used as an add-on device with a host machine transmitting. The probe displacement sensor 2203 can be an accelerometer or gyroscope that senses the three dimensional movement of the probe. During calibration, the probe should be securely attached to the array alignment apparatus so that the probe is still. The calibration system may then compare information from the position sensor of the probe with information from the position sensor of the calibration tank 122 to determine whether the probe is properly aligned.

Figure 23A:
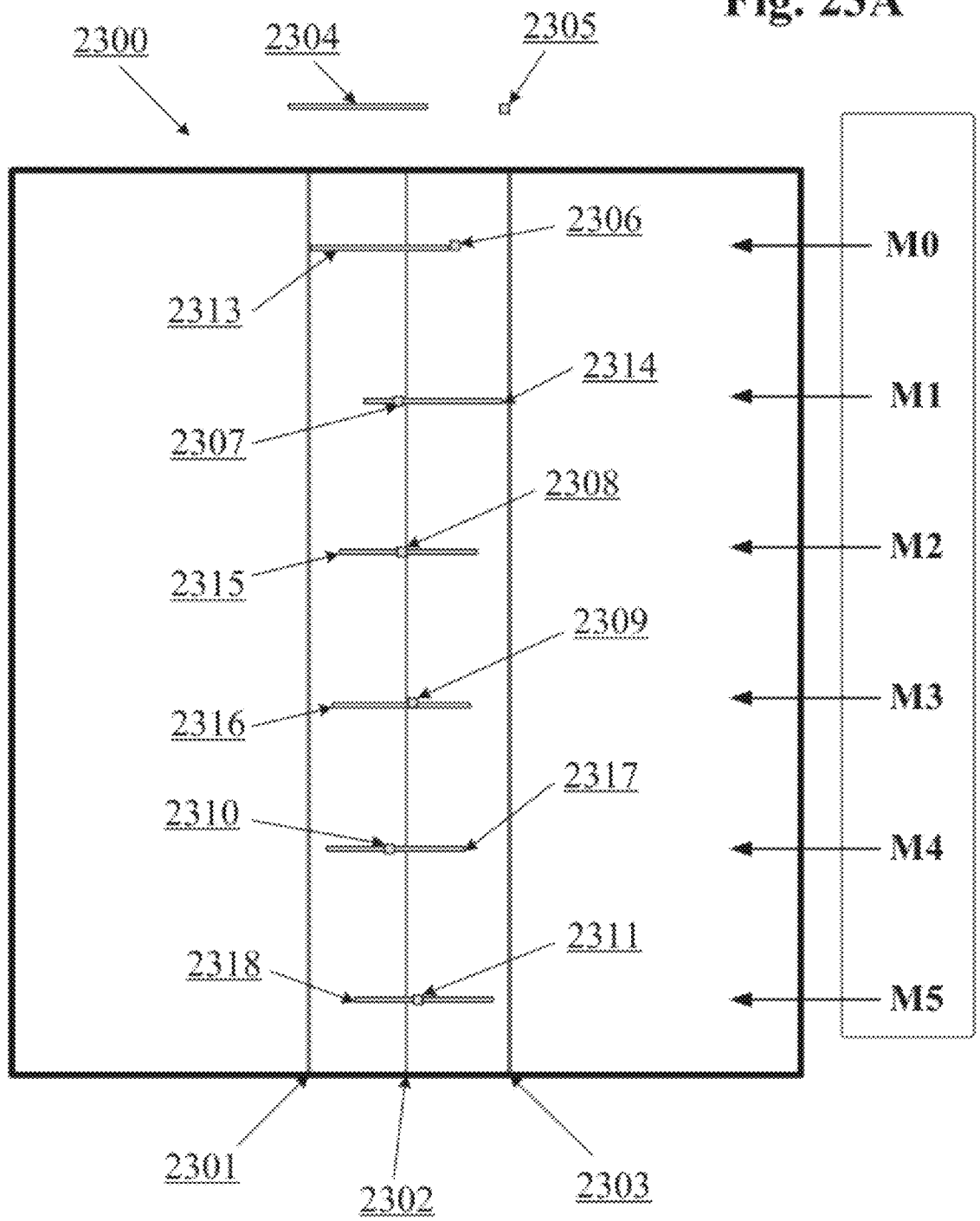
FIG. 23A is a representation of the graphical user interface or GUI developed to allow for the precise location of elements of multiple arrays under test.

Referring now to FIG. 23A, a proprietary graphical user interface or GUI 2300, allows the elemental array data to be visualized in real-time allowing for correction of the x, y and z variation errors. The two wide vertical lines 2001 and 2003 represent the z positions of the yardsticks R 0-RC-RN (2091, 2092, and 2093 from FIG. 19A) and L 0-LC-LN (2094, 2095, and 2096 from FIG. 19A). The thinner vertical line 2302 is the z=0 line and the desired position of each of the elements of a probe system. The vertical position is the x coordinate.

Each small square, such as 2305, 2306, 2307, 2308, 2309, 2310 and 2011, is the position of a probe element in the x-z plane. In this example there are six small squares indicating the positions of the end elements of three probe heads. However, the positions of more or fewer elements could be displayed in this way. The thin horizontal lines 2312, 2313, 2314, 2315, 2316, 2317 and 2018 represent the directivity and angular spread of each element as detected on the multi-axis hydrophone. A useful angular spread measure is the number of hydrophone elements on the transverse hydrophone array which record signal strength greater or equal to half of the maximum strength.

FIG. 23B depicts a probe element positioned correctly with the z position 2305 at or near z=0 and its directivity positioned over the centerline. In contrast, FIG. 23C depicts a probe element with its z position 2305 offset toward the right hydrophone. The resulting display shows the small square, 2305, to the right of centerline, 2302. Note that in this case, the element position is in error, but the element directivity remains over the centerline as indicated on the display by the horizontal line 2312 remaining centered over centerline, 2302.

Figure 23D:
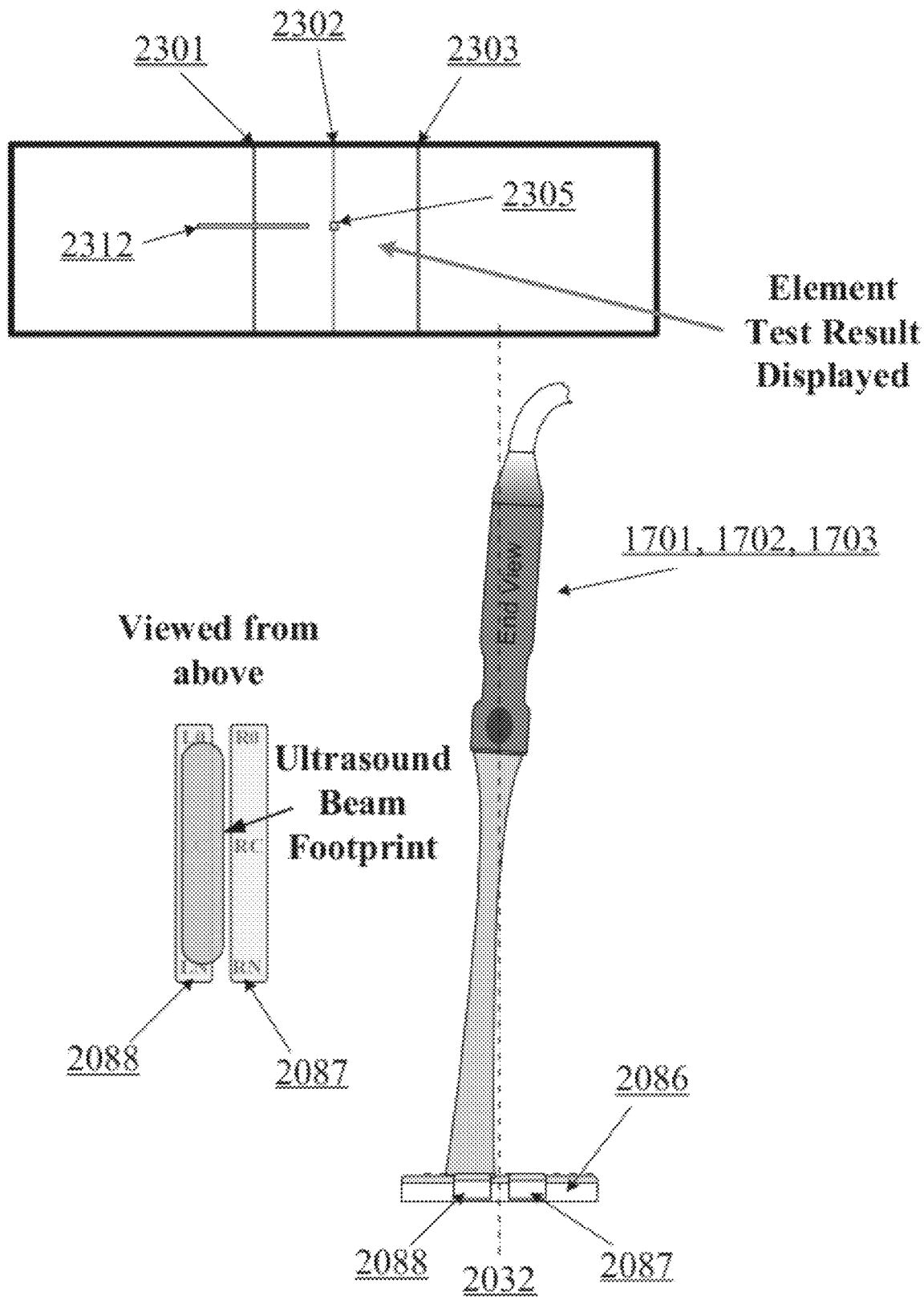
FIG. 23D is a representation of an array under test that is physically on the center axis, but has its beam is to the left of center with the results displayed on the graphical user interface.

Finally, FIG. 23D depicts a probe element correctly positioned with its z 2305 position at or near z=0, 2302. The directivity 2312, however, is misaligned in this case with an offset toward the left hydrophone as indicated by the horizontal line shifted to the left of centerline, 2302. In this case, the directivity needs to be corrected by adjusting the angulation to bring the directivity back over center. This could be accomplished, for example, by using controls 1805 and 1807 in FIG. 18B. Thus with this display, element position and directivity can be monitored simultaneously and both brought into alignment.

Adjustments of the probe position and angulation with the precision alignment stage assembly or assemblies should continue until all of the small squares and all of the horizontal lines are aligned on the center vertical line as closely as practicable, ensuring in alignment in the z axis. As this is done, the x and y positions will be computed accurately and no separate iteration will be required for these.

Figure 24:
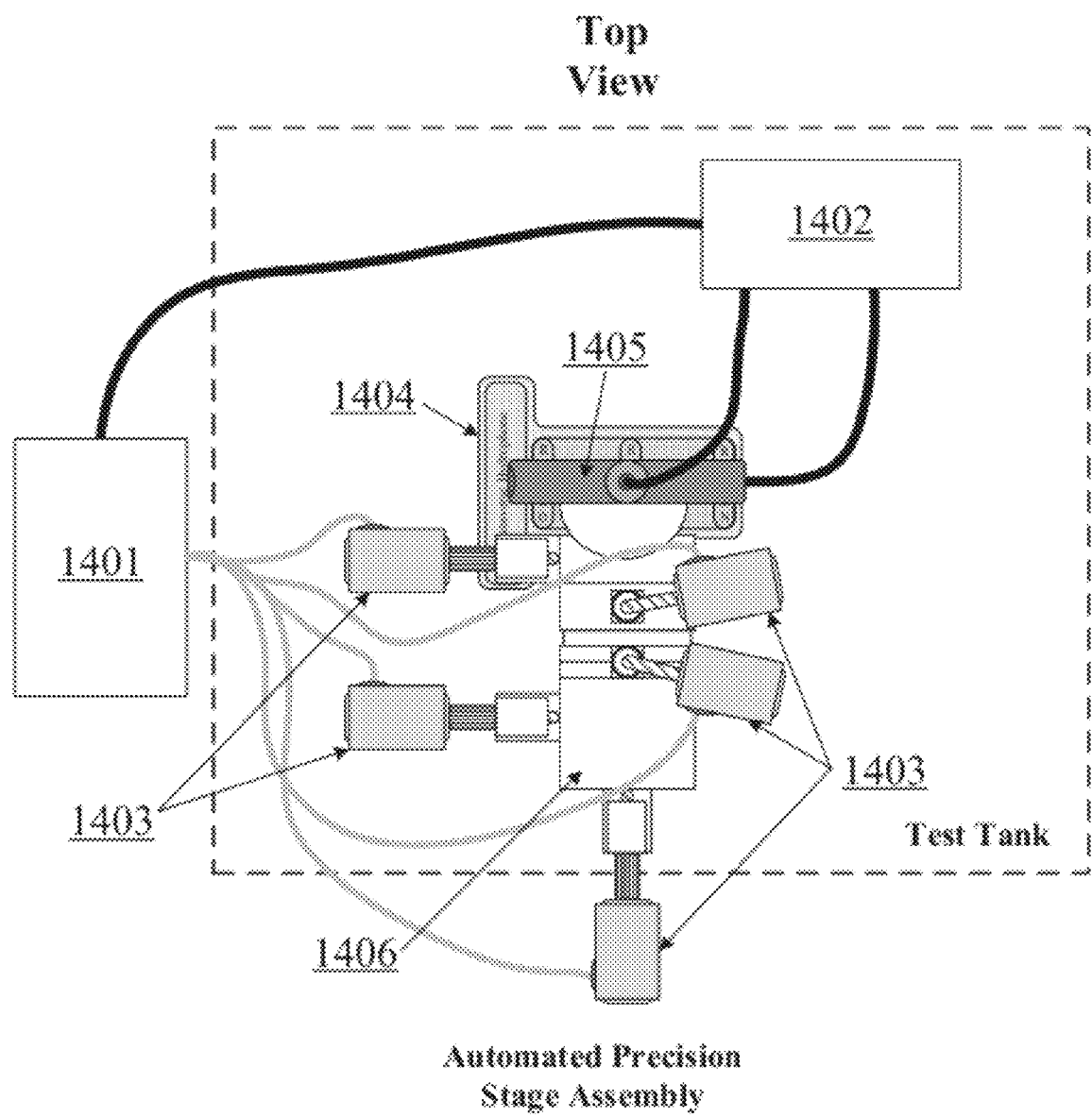
FIG. 24 is a representation of the automatic precision stage assembly and its major components.

In some manufacturing formats, arrays 2406 could be loaded into an automated precision stage assembly like the one in FIG. 24. Here, arrays while still within their nose pieces can still be manipulated. In FIG. 24, we see an automated precision stage assembly, 2406, fitted with precision stepper motors, 2403. Stepper motor controller, 2401, drives the transducer, 2405, under test in response to instructions from controller, 2402. The controller, 2401, evaluates data from the hydrophone assembly, 2404, and calculates transducer corrections. Test programs residing in the controller, 2402, provide transducer specific calibration data back to the transducer, 2405, under test incorporation in it's on board calibration chip, 2201. This automatically acquired element and array position data would be MAUI probe specific and would be used to optimize probe and system performance.

Figure 26A:
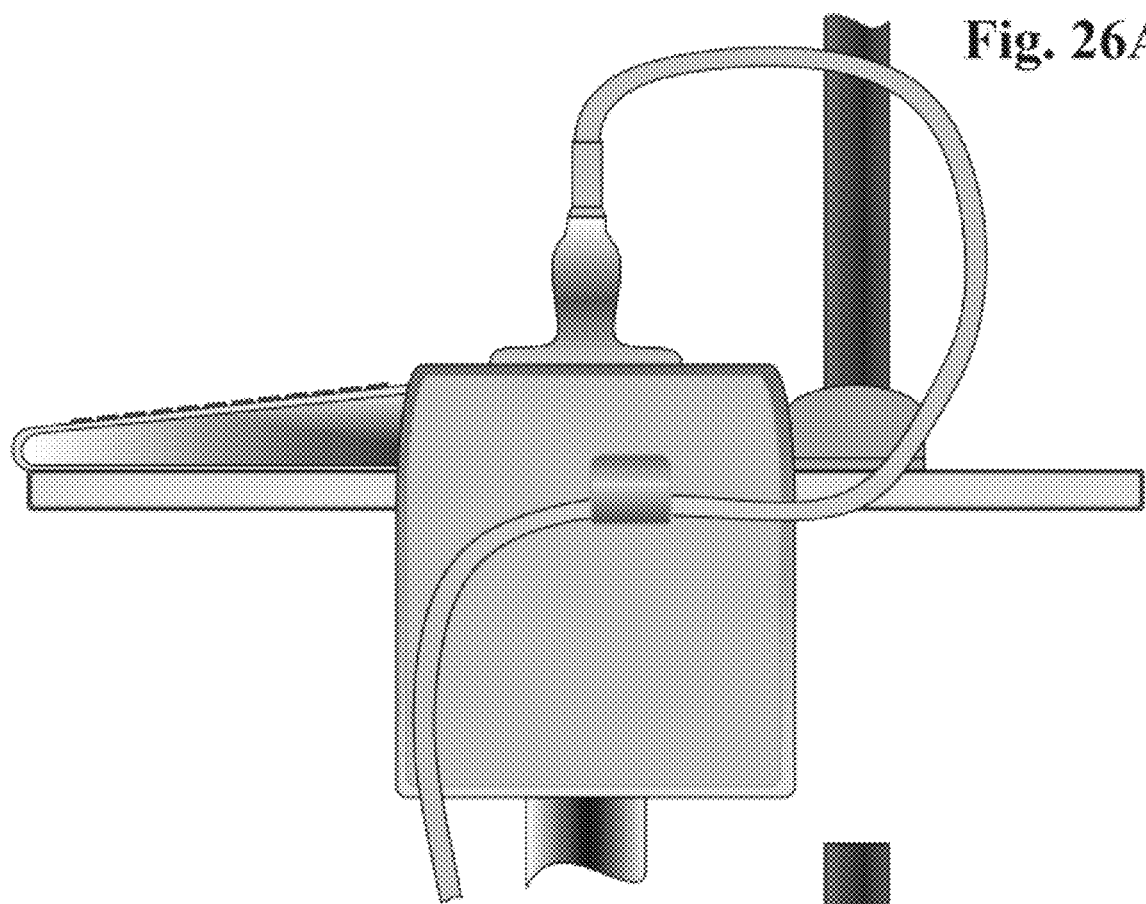
FIG. 26A is an illustration of an Onboard Calibration and Quality Assurance fixture mounted to the side of the MAUI standalone system. This illustration depicts a MAUI Radiology probe being evaluated.
Figure 26B:
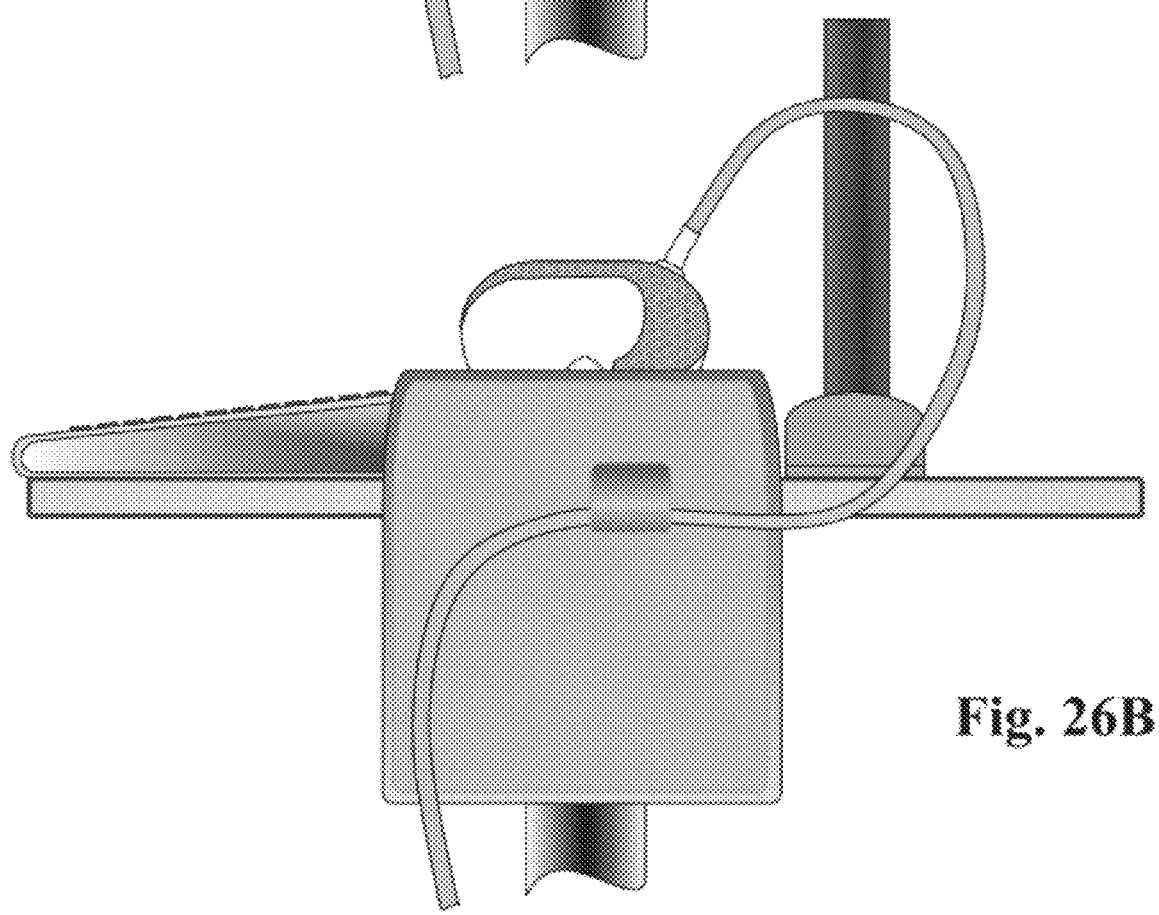
FIG. 26B illustrates the Onboard Calibration and Quality Assurance fixture evaluating a MAUI Cardiac probe.

Using the precision stage assemblies with the array alignment system is only part of the value of the system. FIGS. 20A and 20B illustrate array alignment systems 2610 attached to the control unit 2620 of an ultrasound machine 2600. A cut away shows hydrophone assembly 2085 is located at the bottom of the fluid filled system 2610. In FIG. 26A a MAUI general radiology probe 2630 is affixed to the system for testing. 111 FIG. 26B, a MAUI cardiac probe 2640 is affixed to the system for calibration. The portability of this system, therefore allows for calibration of probes in the field multiple times per day. Additionally the MAUI system would alert the operator if service or maintenance was required.

To calibrate a probe, MAUI electronic apparatus can send a test pattern to the arrays in the probe to transmit to the hydrophone assembly 2085. When the positions of the probes and their directivities are reported as a result of the sequence, the positions of all of the elements can be downloaded to a file specific to that probe. Each file may be stored in the probe calibration chip 2201. The calibration chip may report element positions in x, y and z axes to every MAUI electronic apparatus it connects to, and therefore can perform multiple aperture imaging without recalibrating before use with a different MAUI apparatus. The calibration chip memory can also be used to analyze probe performance and reliability.

In the special case in which all of the transmit and receive elements are aligned in the same plane or are manufactured so that there is no adjustment in z position, a simplified alignment fixture can be used. Instead of two parallel "yardsticks" of hydrophones, a single yardstick can be used. In this case the probe would be centered over the single yardstick using a plumb bob or a clamping device. The x and y measurements would then be made assuming z=0 and zr=0. This is possible since accuracy in the value of z is much less critical in beamforming than is accuracy in the values of x and y. Thus adjusting z by the relatively crude methods of sighting with a plumb bob or clamping to a machined edge of the probe can be acceptable in spite of the high accuracy demands for measurement of x and y. Obviously, the cost of this simplified fixture would be much reduced resulting in a fixture which could be used in the field rather just in the probe assembly factory.

Embodiments below provide further systems and methods for calibrating ultrasound imaging probes as well as systems and methods for testing quality assurance characteristics of ultrasound imaging probes. Although the following embodiments are shown and described with reference to multiple aperture ultrasound imaging (MAUI) probes, the skilled artisan will recognize that many features of the systems and methods described may also be applied to ultrasound probes of any configuration where it is desirable to determine the acoustic position or the health of one or more ultrasound transducer elements in an ultrasound probe.

Figure 34B:
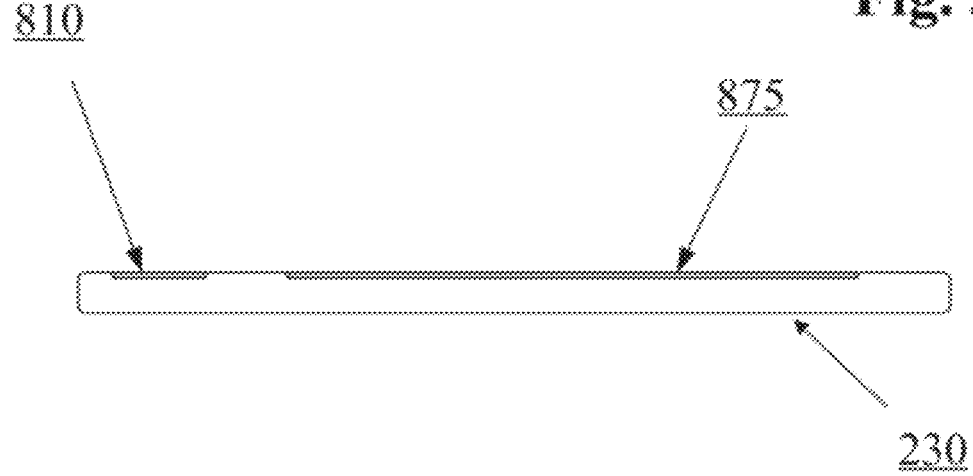
FIG. 34B a side view of the hydrophone matrix of FIG. 34A.

As discussed above and with further reference to FIGS. 28, 34A, and 34B, some embodiments of a calibration process may comprise three stages: First, a single test-element of the probe may transmit an ultrasound test signal into the calibration tank 122 through the filler material 210. Second, the hydrophones 230 may receive the ultrasound test signal, and associated electronics and/or software may geometrically triangulate the origin of the test signal in order to determine an acoustic position of the test element to within a desired degree of accuracy. Third, the acoustic position of the test element may be transformed into a coordinate system with a known origin relative to the probe. Coordinates for the test element may be stored in a table of coordinates associated with the probe. These steps may then be repeated for each transducer element in each transducer array within a probe until the acoustic position of each element is determined and recorded in a table of coordinates.

Embodiments of the systems and methods herein may quantify both transmitted and received ultrasonic pulses and use the information Obtained to identify the acoustic position of single transducer elements and/or full arrays of transducer elements. Further, embodiments of the systems and methods herein may also quantify the "health" of probe elements. The "health" of a probe element may refer to a number of factors including transmitting and receiving efficiency of probe elements, element sensitivity, and electronic functionality.

Probes with multiple aperture arrays may be properly aligned during production as discussed above. However, regularly recalibrating an ultrasound probe throughout the life of the probe as opposed to only during manufacturing can allow for high quality imaging over a long period of time without requiring the probe to be returned to a manufacturer or repair facility. To address these needs, a calibration system may be provided to accompany probes into the field. In some embodiments, a calibration system may be attached to or integrally formed with an ultrasound control panel. In some embodiments, a calibration system may include a tank in the shape of an open-topped box with a mounting portion in a top section of the box for holding a probe in a calibration orientation and a plurality of receivers at a bottom of the box for receiving ultrasound signals transmitted from the probe.

By providing a calibration system as an attachment to an ultrasound imaging system the calibration system becomes easily accessible to operators. In some embodiments, the calibration system may serve as a probe storage location for holding probes not in use. In some embodiments, a plurality of imaging probes of different configurations may be stored in the calibration system. Probes may then be selectively calibrated according to a calibration process, thus making a wide range of probe designs readily available for imaging. Moreover, adjustable multiple aperture probes may be re-configured into a different shape and then recalibrated for each patient.

Figure 27A:
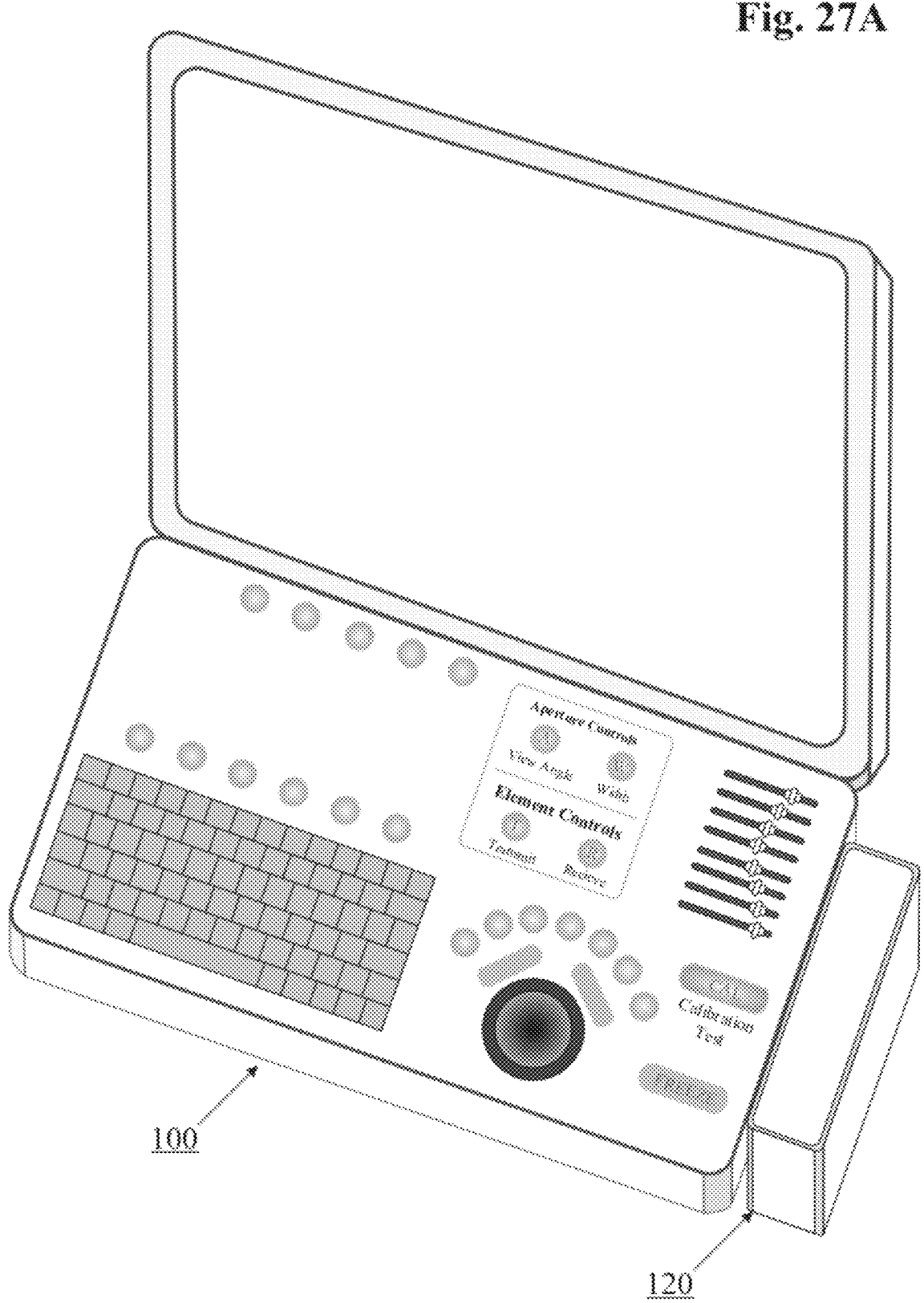
FIG. 27A is a perspective view illustrating an embodiment of a calibration system attached to a multiple aperture ultrasound imaging (MAUI) control panel.
Figure 27B:
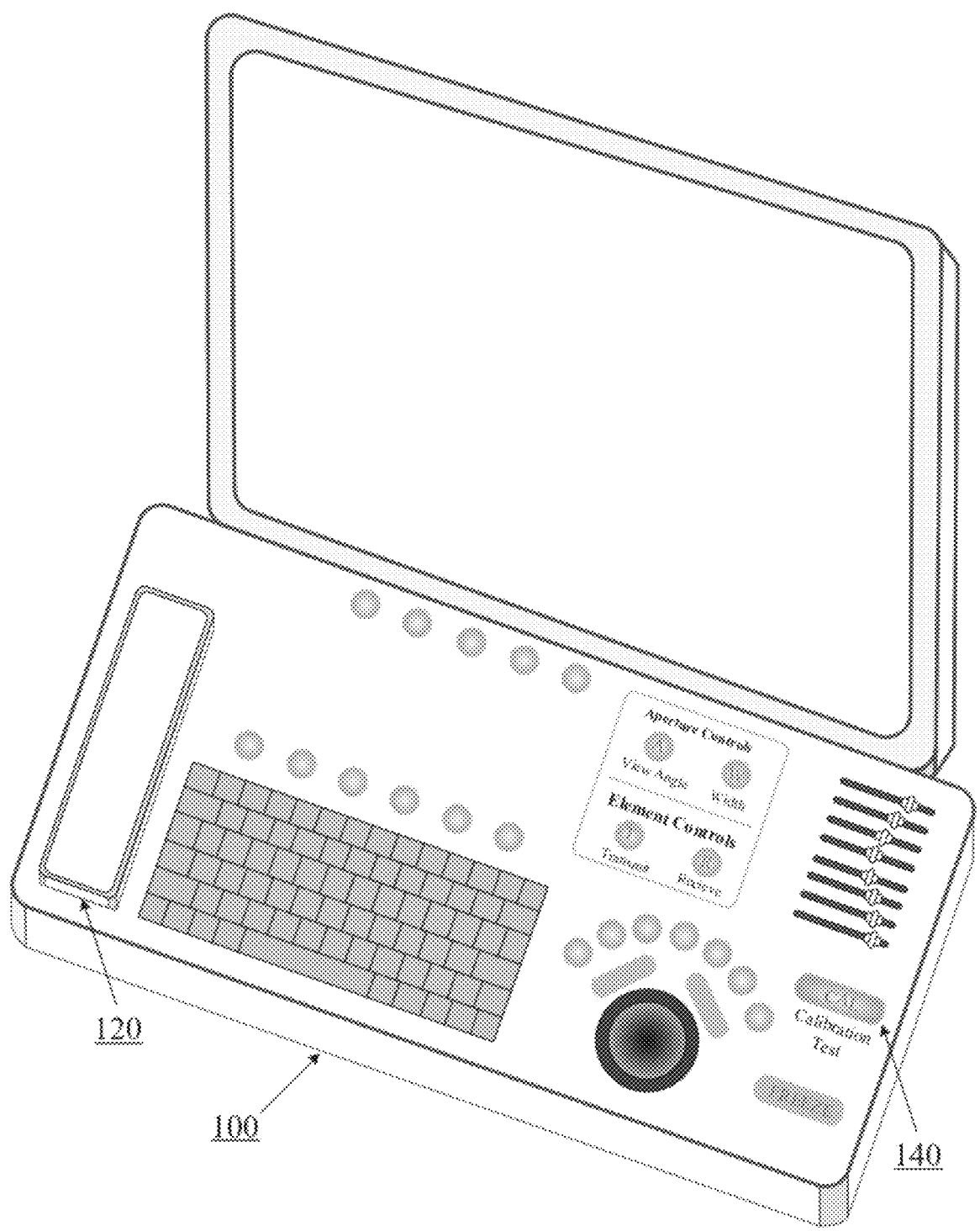
FIG. 27B illustrates an embodiment of a calibration system built o a MAUI electronics control panel.

Referring to FIG. 27A, a calibration system 120 may work in conjunction with a control panel 100. The control panel 100 can contain and control electronic hardware and software configured to transmit, receive and process ultrasound signals using a multiple aperture ultrasound imaging (MAUI) probe. Such hardware and software is generically referred to herein as MAUI electronics. As shown in FIG. 27A, the calibration system 120 may be externally mounted to a control panel 100. In such embodiments, the system 120 may be electronically connected to the MAUI electronics by a wired system which may include any desired wiring arrangement, such as wiring harnesses or removable plugs. Alternatively, referring to FIG. 27B, a calibration system 120 may be embedded into the control panel 100. In further embodiments, a calibration system 120 may be provided as an entirely separate device, which may be electronically connected to the MAUI electronics by any suitable wired or wireless arrangement. In further embodiments, the electronics controlling a calibration system, including electronics controlling a probe during calibration may be entirely independent (physically and/or electronically) of the electronics used for controlling an ultrasound imaging process.

Figure 28:
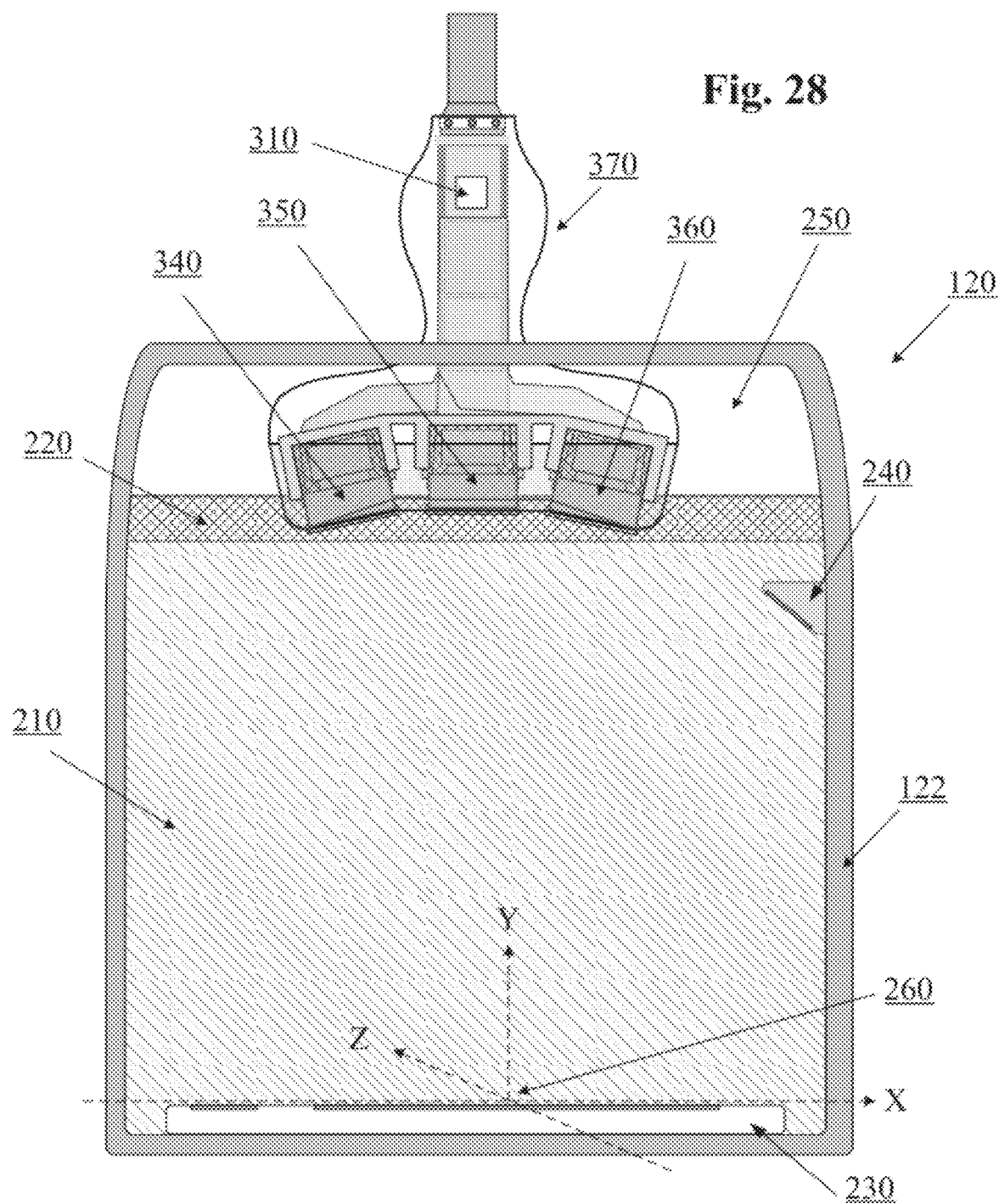
FIG. 28 represents a side section view of a calibration system.

As shown in FIG. 28, in some embodiments the calibration system 120 may resemble a rectangular tank that may be relatively small in size without the bulky alignment features that can be required during manufacturing. In some embodiments, an opening at the top of the tank 122 may be sized to receive a probe 370. The tank 122 may have an overall height approximately the length of a pencil box (e.g. between about 10 and 24 inches in some embodiments), although larger or smaller tanks may also be used. In some embodiments, a width and/or depth (e.g. in/nut of the plane of FIG. 28) of the tank 122 may be sized to minimize un-desired reflections from side walls of the tank. Additionally, a material and internal surface texture of the tank 122 may also be engineered to minimize noise from undesired reflected ultrasound waves.

In some embodiments, a matrix of ultrasonic sensors or hydrophones 230 may be attached to the bottom of the tank 122. The matrix of hydrophones 230 can function similar to the multi-axis hydrophone 2085 described above. It is desirable for the calibration tank 122 to be configured such that an entire ultrasound path between the probe and all receivers is occupied by a material with a consistent and known speed of sound. Thus, similar to the tank 2012 described above, the tank 122 may be filled by a filler 210 made of a liquid, gel or solid material with a consistent and known speed of sound. The fitter 210 may be any material that is desirable for manufacture and safety considerations. The speed of sound through the filler 210 should be known precisely in order to accurately calculate the distance traveled by any given ultrasound pulse during a calibration process. In one embodiment, the filler 210 is made of a relatively rigid ballistics gel. The filler 210 can occupy substantially all of the tank 122. In some embodiments, the filler occupies most of the tank 122 except for a top layer which may be reserved for a docking area 220 configured for receiving an ultrasound probe to be calibrated.

In some embodiments, the docking area 220 may be an empty void which may be filled with a liquid or gel which may conform to a shape of a probe to be calibrated such as the illustrated multiple aperture probe 370. In other embodiments, the docking area 220 may include a molded piece of ballistics gel (or other suitable material) configured to conform to the shape of a probe to be calibrated. Preferably, the material used in the docking area 220 has substantially the same speed of sound as the filler material 210. In other embodiments, the docking area and/or the entire filler may comprise a flexible bladder filled with a suitable liquid or get material. In some embodiments, the probe and/or the docking area may be coated with an ultrasound coupling gel as will be clear to the skilled artisan.

Figure 31:
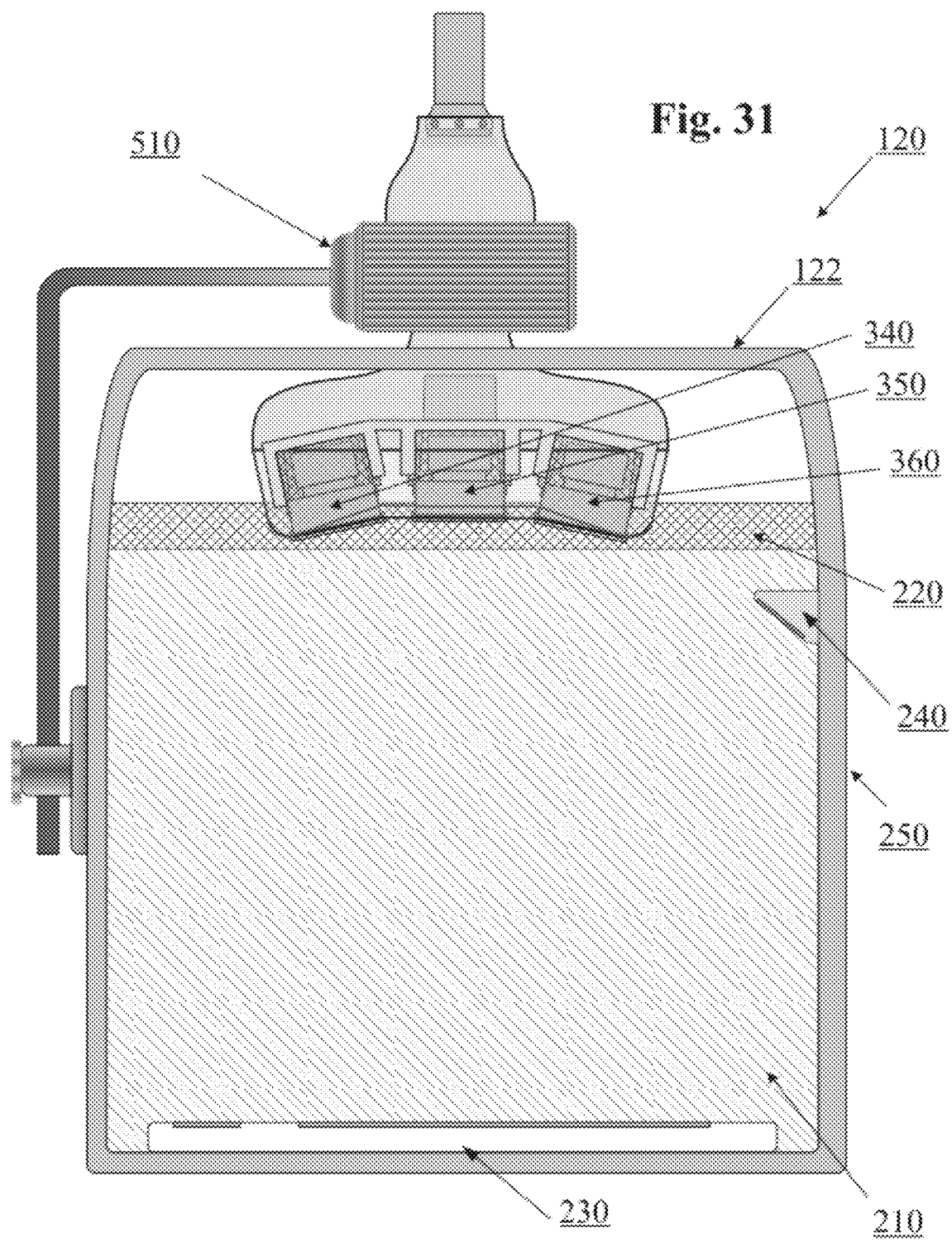
FIG. 31 illustrates an embodiment of a calibration system with an adjustable clasp retaining one embodiment of a MAUI probe in a docking site which may contain a coupling gel.

For the best results, probes should be substantially immobile during all calibration and quality testing. To reduce error the calibration system 120 may be equipped with a mechanical docking device configured to hold the probe(s) in a substantially rigid and consistent position. Referring to FIG. 31, in some embodiments, an adjustable clasp 510 may be provided to capture and hold a probe 370 by a handle section or any other suitable portion of the probe. In other embodiments, a clasp or grasping element may be integrally formed with the docking area 220. In some embodiments, the docking area 220 and/or a clasp 510 may include electronic contacts or other elements which may interact with corresponding features on a probe to ensure consistently proper positioning of the probe for calibration.

In other embodiments, accelerometers, gyroscopes or other position sensors within the probe may be used to inform an operator of proper or improper positioning of a probe within a docking area of a calibration system. In some embodiments, corresponding position sensors (e.g. gyroscopes, accelerometers or other sensors) may be provided in or on the calibration tank. A calibration system may then compare information from the position sensor of the probe with information from the position sensor of the calibration tank 120 to determine whether the probe is properly aligned for calibration.

FIGS. 32A-33B illustrate embodiments of docking devices 610 that may be used in a docking area of a calibration system. FIG. 32A shows an embodiment of a docking device 610 with a plurality of probe-specific molded receivers (602-628). In such an embodiment, each probe that might be used with a particular system may have a specific receiver within the calibration system. For example, the top center docking site 604 may be configured to receive a curvilinear MAUI probe 375 having a continuous concave curved array 378 of ultrasound transducer elements such as that shown in FIG. 29B.

FIG. 32B is a cross-sectional view of the calibration tank taken through line A1-A in the plan view of FIG. 32A. In some embodiments, each docking device molded receiver may be manufactured to best fit the specific needs of each probe; this can be especially useful for probes with a more tight curvature or uniquely designed probes.

Figure 33A:
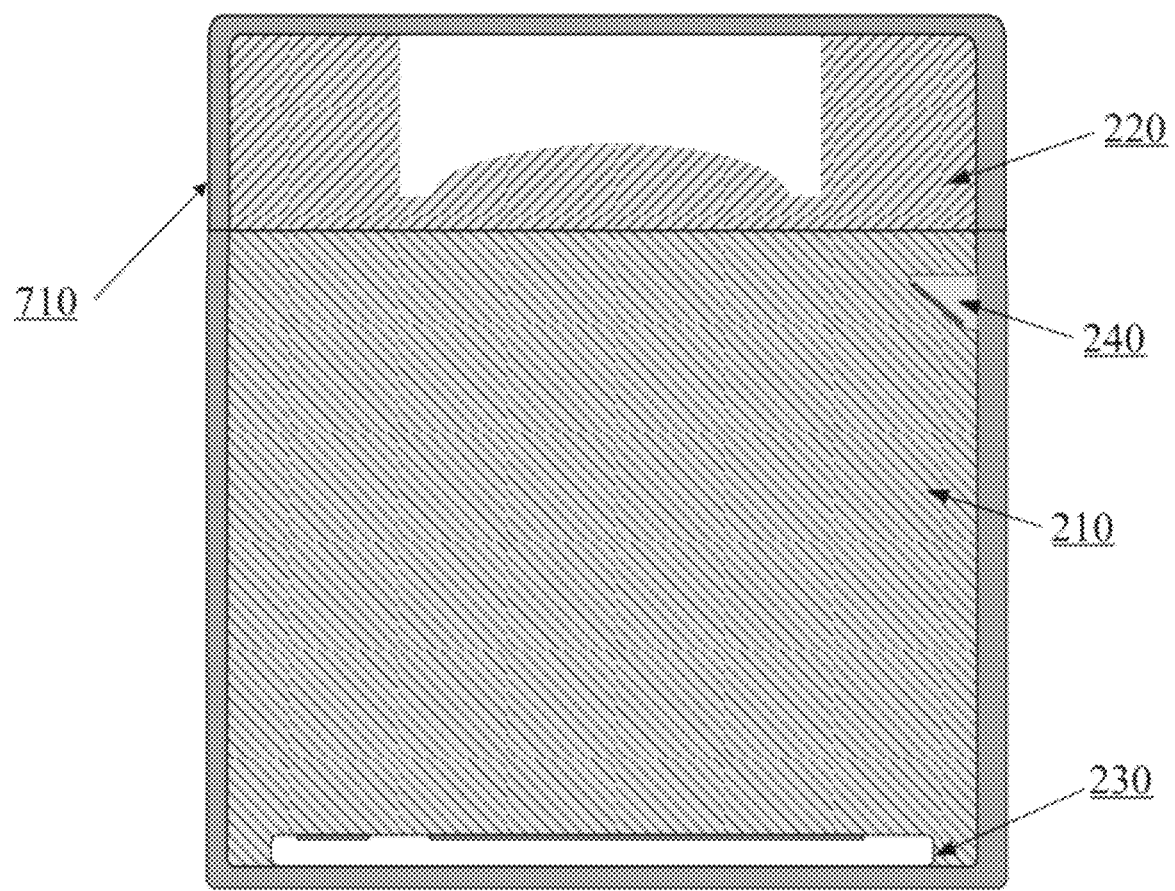
FIG. 33A shows a side section view of an embodiment of a calibration system with a removable docking site with a single docking form for receiving an ultrasound probe.
Figure 33B:
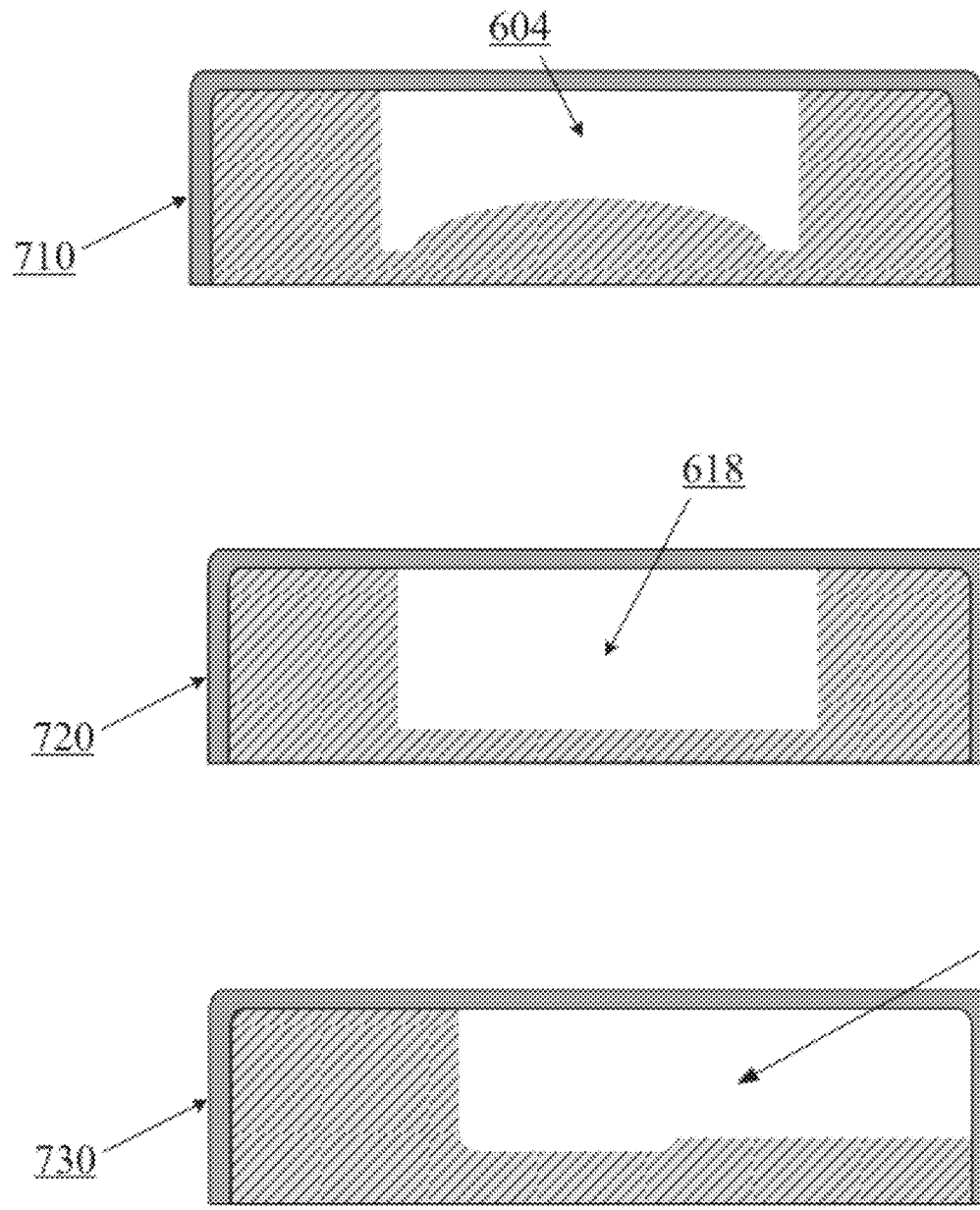
FIG. 33B is a section view illustrating three embodiments of docking forms the curvilinear, linear and trans-esophageal ultrasound probes.

Other embodiments, as shown for example in FIGS. 33A and 33B may feature interchangeable docking receivers custom made for each transducer. The docking receivers 710, 720, and 730 may be removably attached to a docking area 220 of the calibration system. Each receiver 710, 720, and 730 may be formed for a specific type of probe. In further embodiments, one or more receiver may be configured to receive any of the probes shown and described in U.S. patent application Ser. No. 13/029,907 now published as US Patent Application Publication 2011/0201933 and incorporated herein by reference.

In some embodiments, the dock may be configured such that the ultrasound probe may be stored in the dock when not in use. The user or operator can then optionally calibrate the probe prior to removing the probe from the dock.

In some embodiments, one or more temperature sensors may be provided and configured to measure a temperature of the filler 210. As discussed above, the temperature of the filler material 210 is used to calculate the acoustic position of transducer elements in a probe during calibration. Thus, in some embodiments, a plurality of temperature sensors (e.g., thermocouples, thermistors, optical thermal imaging systems, etc.) may be positioned throughout the tank to obtain enough measurements to determine an average temperature of the filler 210 at any given time. In other embodiments, a single temperature sensor may be sufficient.

In some embodiments, a hydrophone matrix 230 such as that shown in FIG. 34A and FIG. 28B may be used to detect the X, Y and Z positions of each element of a single array or multiple arrays in a probe under calibration. In some embodiments, the multi-axis hydrophone 230 can include a transverse hydrophone array 810, a right hydrophone array 845 and a left hydrophone array 875. In other embodiments, the hydrophone matrix may include only a single array of hydrophone elements. In other embodiments, a hydrophone matrix may comprise a two-dimensional array of many detector elements to enable further measurements. For example, the hydrophone matrix may comprise a 3×3 array, a 4×4 array, a 4×6 array or any other 'n'ב'm' array of hydrophone elements.

In some embodiments, the hydrophone matrix 230 may act as a target when the probe is firing. In some embodiments, hydrophone elements selected to be detectors to may depend on the size, shape and orientation of the probe to be calibrated. In some embodiments, such calibration process details may be stored in the calibration chip or another data store in communication with the calibration system electronics.

Figure 30A:
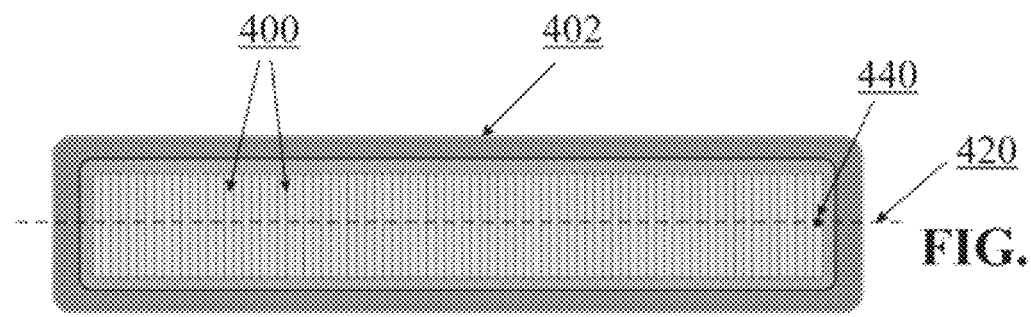
FIG. 30A is a bottom view of a 1D or 1.5D ultrasound transducer array.
Figure 30B:
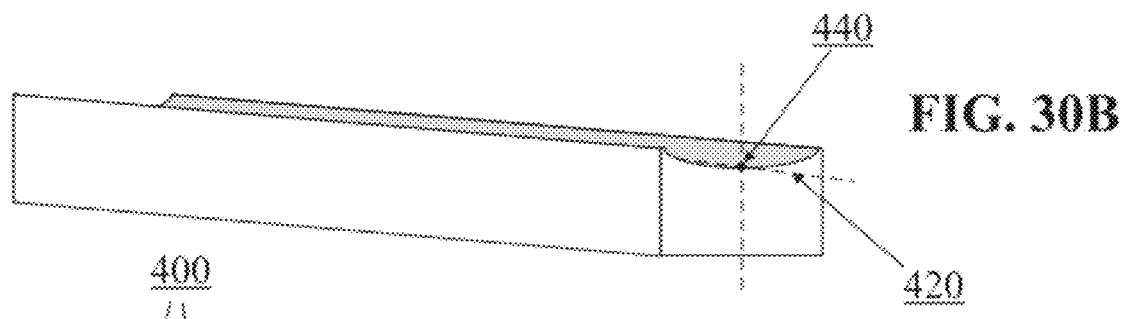
FIG. 30B is a perspective view of a single 1D or 1.5D ultrasound transducer element with a longitudinal geometric centerline shown.
Figure 30C:
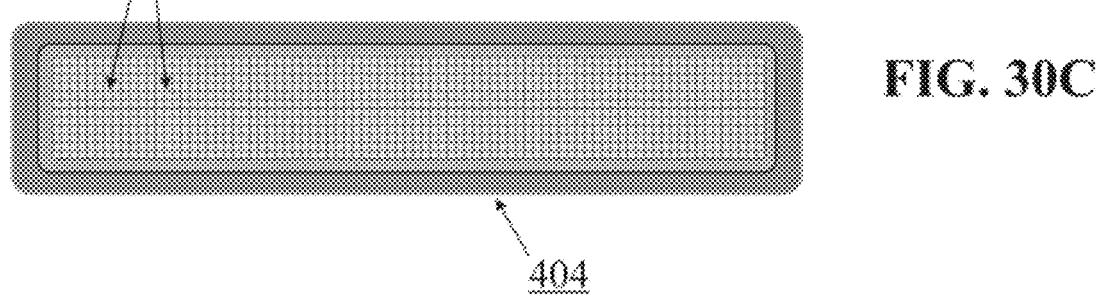
FIG. 30C is a bottom view of a 2D matrix ultrasound transducer array.
Figure 30D:
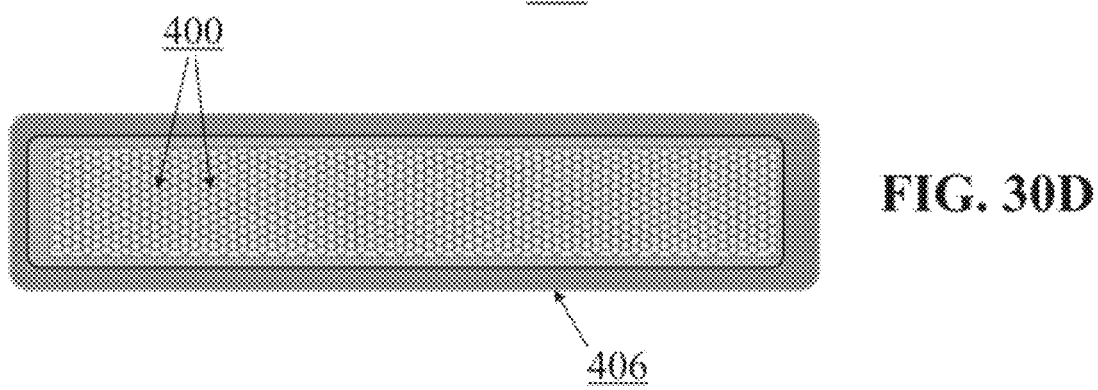
FIG. 30D is a bottom view of a CMUT ultrasound transducer array.

Ultrasound transducer elements or arrays of elements are typically cut from a common crystal wafer (e.g., of a piezoelectric crystal) to form 1D, 1.5D and 2D arrays. Alternatively, some ultrasound elements may be printed or machined into a micromachined lattice structure to form an array called a Capacitive Micromachined Ultrasonic Transducer (CMUT) array. FIG. 24A illustrates a ID piezoelectric transducer array in which each rectangular segment represents a single transducer element 400. Such an array is referred to as one-dimensional because the array has only rows of longitudinal transducer elements without columns. FIG. 24B illustrates a 2D piezoelectric transducer array in which each square segment represents a separate transducer element 400. Such an array is referred to as 2-dimensional because the array of elements extends in two directions, having both rows and columns. FIG. 30C illustrates u CMUT array in which each transducer element 400 has a more complex geometric shape. Furthermore, a CMUT array has a much more complex arrangement, where elements are not necessarily arranged in rows and columns.

In the case of conventional 1D and 1.5D phased array probes, the position of the elements is often roughly determined by the size of the cuts inside the crystal wafer upon initial manufacture. Reaming to FIG. 30B, in this process, the acoustic center of each element is assumed to be at the center of the shaped crystalline structure 440, usually a parabolic channel running down the mid portion 420 of the elements. This may or may not be the true acoustic center of the element due to slight variations in the structure of the PZT crystal or variability in the machining process. Nonetheless, transmit and receive beamformers typically assume that the acoustic center position of a transducer element is coincident with its geometric center. When the true acoustic center of an element is not exactly at the geometric center (e.g., along the longitudinal axis 420), then both transmit waveform energy and echoes being received are not being optimized. They are subject to the errors of being out of alignment, which detrimentally affects image quality and depth. The same problem may also exist fix 1.5D, 2D and CMUT arrays. Therefore, even traditional single-aperture phased array probes may benefit from regular calibration using the systems and methods described herein.

Once an ultrasound probe is firmly mounted in the docking area of the calibration system, a calibration process may be initiated. In some embodiments, a calibration process may be initiated by a user pressing a button (e.g., 140 in FIG. 27B) on a calibrator or imaging system control panel.

In some embodiments, the calibration system may be configured to determine the acoustic position of transducer elements relative to a single array of which an individual test element is a part. For example, in the case of a multiple aperture probe such as that shown in FIG. 29A, the acoustic position of each element on the center array 350 maybe determined relative to a coordinate system 380 centered on that array. Similarly, the acoustic positions of elements in the left 340 and right 360 arrays may also be determined relative to separate coordinate systems centered on those respective arrays.

A further calibration process may then be employed to detect the position of one full array relative to another, thereby providing information describing the relative positions of the three coordinate systems. In such an embodiment, test signals may be transmitted from elements at opposite ends or corners of each array to be located relative to other arrays. This may allow for the measurement of the length, acoustic center and 3-dimensional orientation of each array relative to other arrays in a probe containing multiple arrays. For example, the position and orientation of a planar transducer array may be determined by identifying the three-dimensional location of a sufficient number of array elements to define the orientation of the array's planar surface. In some embodiments, three elements may be sufficient to define the plane of an array. In other embodiments, several or all elements may be located to define the orientation of the array's plane. In some embodiments, information describing the orientation of a planar array may be stored along with other calibration data. Such embodiments may be especially useful when calibrating adjustable probes which may contain two or more physically separate arrays which are free to move relative to one another.

In some embodiments, the calibration system can be configured to transmit a new test signal to the hydrophone matrix from every element of the probe such that the acoustic location of every element of the probe can be determined. In other embodiments, a test signal can be sent from only a few of the probe elements, such as two probe elements in an array, and the remaining locations can be determined through interpolation.

Many transmit pulse patterns may be used in the step of transmitting an ultrasound test signal from a test element. In some embodiments, an ultrasonic test signal may be transmitted which exhibits good autocorrelation properties. In some embodiments, such a test signal may comprise a long frequency sweep, a 'chirp' waveform, a spread spectrum waveform, a 'ping', a pseudorandom sequence, or another suitable pattern. In some embodiments, a test signal may be selected to require minimal computational complexity.

As will be clear to the skilled artisan in view of the discussion herein, the only directly measurable ultrasound parameter in the calibration system is the time delay between transmission of a test signal from a probe test element and receipt of the test signal at each hydrophone element. Based on these time delays, known speed of sound through the filler material, and known physical geometry of the calibration system, the position of a test element may be calculated.

It is important to note that in many cases, a test element may distort the timing of a transmitted signal. Thus, in some embodiments, it may be desirable to perform time delay measurements without relying on a presumed "transmit time" as determined by a time of sending an electrical signal to a transducer element. In such embodiments, the total distance traveled by an ultrasound test signal may be determined by using only the speed of sound and the difference between the time at which the test signal is received at a first hydrophone element and a time of the test signal at a second hydrophone element.

Multiple techniques, such as those described above with reference to FIGS. 21A, 21B & 21C, may be used to obtain the needed accuracy in finding the relative time delays and hence the relative distances, including using cross correlation between the signal received at one hydrophone element (e.g., 820) and the signal received at another element of the same hydrophone array (e.g., 840), interpolating between samples of the received waveforms to obtain better time resolution than simply the sampling interval, and converting a differential distance measured by two hydrophone elements to a total distance traveled by an ultrasound test signal.

Referring to FIG. 28, a coordinate system 260 can be established relative to the hydrophone matrix. In FIG. 28, the X-axis is aligned with left and right directions in the tank, the Y-axis is aligned with the "up and down" directions in the tank, and the Z-axis is perpendicular to the scan-plane and the plane of FIG. 28. The position of a plurality of probe elements, such as every probe element, can then be determined relative to the coordinate system 260.

In some embodiments, position measurements may be translated from the coordinate system 260 with an origin relative to the hydrophones matrix to a coordinate system 380 with an origin located on the probe itself, as shown in FIG. 29. In the coordinate system 380 shown in FIG. 29, the X-axis lies along a center line of three arrays, the Y-axis is perpendicular to the plane of the center array, and the Z-axis is perpendicular to the X & Y axes, extending in and out of the page of FIG. 29A. In some embodiments, a process of rotating and translating coordinates may be used to translate the coordinate systems. In some embodiments, an appropriate probe-relative coordinate system may be dependent on the ultrasound imaging system for which the probe assembly is to be used.

With a conventional array, a transmit pulse from a transmitting element to a reflector is easily calculated back to a given receive element. Assuming a constant speed of sound, the positions in a conventional matrix or linear array are mechanically assumed so that transmit and receive paths can be easily computed in multiple aperture imaging it is important to determine the position of each element relative to the position of any other element(s) in a known space such as a Cartesian X, Y, and Z coordinate system illustrated in FIG. 31 for example. In some embodiments, such a coordinate system may have one element designated as an origin and acoustic center positions of all other element(s) may be assigned coordinates relative to this initial position. From this the position of any element may then be known relative to any other.

As will be clear to the skilled artisan, the origin of a coordinate system may be centered at any element, or at any other point on or off of the probe. Additionally, the calibration system need not necessarily use a Cartesian coordinate system; any suitable coordinate system may be used, provided that such a coordinate system gives accurate information about the position of transducer elements.

The information obtained through calibration as well as the new coordinate system may then be compared to original element position information for the probe, as well as any previous calibration data. In some embodiments, this information may be tracked over time to better understand the properties of the probe elements and the probes as they are used. In some embodiments, this time-series calibration information may be stored and/or analyzed in an ultrasound imaging system, a remote server system, or any other suitable computing system.

During manufacturing, each MAUI transducer may be properly aligned and calibrated according to the type of crystal matrix used. The initial coordinate system and calibration may then be programmed into a memory chip 310, which can be set in the handle of the probe as shown in FIG. 29A. When the probe is recalibrated at some later time, the calibration system electronics may compare the new calibration results to the initial or last-known position of the elements. Difference data or new position data may then be updated in the calibration chip 310. Besides maintaining the calibration data, calibration chip 310 may also contain data for setting up a general layout of each probe, this information may be used to inform the calibration system of the number of elements to fire and in roughly what order or design during calibration.

In some embodiments, calibration data for a probe may be stored in a location other than the probe itself. It is generally desirable for calibration data to be associated specifically with the probe it describes, but such information may be stored in any practical physical location. For example, in some embodiments, a probe may have an ID chip which carries substantially only an identification number which may be used to retrieve a unique calibration record stored in a remote (e.g., internet-accessible) database, in an ultrasound imaging system, or any other location. In some embodiments, communications systems may also be provided to allow for logging of calibration data into an ultrasound imaging system data log, and/or sending to a service provider and/or providing an operator with an appropriate on screen notification.

Each probe may have a unique element coordinate table which may be permanently associated with the probe, and which may be updated in subsequent calibration processes. In some embodiments, the calibration data overwrites calibration data previously stored in the memory. Overwriting advantageously ensures that updated data is constantly available, even in systems with small amounts of available memory.

In some embodiments, probes may be re-calibrated and data stored as many times as desired by an operator, technician, or manufacturer.

The stored coordinate table may be used by ultrasound imaging system electronics in order improve the quality of ultrasound images generated using the calibrated probe. In one embodiment, the updated position data can be used during imaging, e.g., the stored data can be used as an input in an algorithm used to generate an image from a multiple aperture ultrasound imaging system. In another embodiment, the stored coordinate table can be used in post-image processing, i.e., the stored data can be used to decode stored image data or raw echo data.

Instruments of any kind used in the field on a daily basis will typically suffer from general wear and tear. To better understand the degradation of ultrasound transducers over time, as well as to obtain regular feedback pertaining to the general functionality of the probe, the calibration system may also be configured to perform general quality assurance functions. In some embodiments, the calibration system may test both the transmitting and receiving functions of the probe, report operational capabilities to the sonographer and send probe functionality data and repair requests to the service provider.

In some embodiments, the quality assurance test may be performed before each calibration so that the information obtained can be used to more accurately calibrate the probe. In some embodiments, after securing a probe in a docking area of the calibration system, a quality assurance test sequence may be manually or automatically initiated. For example, in some embodiments, the quality assurance test may be initiated via a button on the control panel. In some embodiments, a quality assurance test sequence may comprise three stages: The first stage will be referred to as hydrophone verification, the second stage will be referred to as an element transmit test and the third will be referred to as an element receive test.

In some embodiments, an additional self-test hydrophone 240 may be mounted to a side wall near the top of the tank 122 for use in quality assurance testing. The self-test hydrophone 240 and corresponding control electronics may be configured to check the position and function of the hydrophones of the main hydrophone matrix 230 in order to ensure proper calibration of the calibration system. In one embodiment the self-test hydrophone 240 may be located in the top of the tank 122 along the centerline of the hydrophone matrix 230. In other embodiments, a self-test hydrophone 240 may be positioned at any other location within the tank suitable for performing the described functions. In a process similar to the process for calibrating ultrasound probe elements, the self-test hydrophone 240 may send and receive ultrasound pulses to the main calibration hydrophones 230 and then use this information to ensure the hydrophones 230 are functioning properly and accurately.

Each hydrophone of the main hydrophone matrix 230 may also transmit a self-test signal to be received by the self-calibrator hydrophone 240. The process may be similar to those described elsewhere herein for the calibration and quality assurance testing of ultrasound probe elements. The proper functioning and exact location of the hydrophone elements is very important for the best possible calibration of the probes.

In some embodiments, the hydrophone verification stage may ensure that information obtained from the hydrophones is accurate. As shown in FIG. 28, some embodiments of the calibration system may be equipped with one or more self-calibrator hydrophones 240 located in a top corner of the tank. A self-calibrator hydrophone 240 may be used to verify the transmitting and receiving capabilities of the hydrophones elements of the hydrophone arrays 810, 845, 875 in the hydrophone matrix 230. In some embodiments, the self-calibrator may also be used to verify the acoustic positions of the elements of the main hydrophone matrix 230. The self-calibrator may transmit ultrasonic self-test signal pulse or pulses in a set pattern from a known location. The strength of received signals and the order in which they are received may be used to determine the acoustic position and receiving functionality of the hydrophone elements using methods similar to those described above.

In some embodiments, a quality assurance transmit test may be designed to test the transmit strength, efficiency and/or effectiveness of each transducer element of an ultrasound probe. A QA transmit test may begin by exciting a test transducer element with a precise electrical signal to cause the transducer to transmit ultrasonic pulses. The transmit test signal may have any shape and frequency as desired, preferably with good autocorrelation properties as discussed above with reference to calibration test embodiments.

The test signals may then be received by one or more hydrophone elements. The received frequency may then be transformed by the hydrophone transducer into specific amplitudes of electrical charge. From the resulting charges obtained by the hydrophones, the calibration system may determine whether a received signal has expected properties based on the electrical signal input to the test element. After testing all test elements, the calibration system may determine which test elements fall below an average transmitting capability and which fail to fire at all. This information may be obtained by comparing the amplitudes created by each test signal and then identifying which elements fall below the mean and by how much. In some embodiments, QA transmit test result data may be stored in a calibration chip within a probe or in any other suitable location. In some embodiments, an absolute value of a mean transmit strength may also be stored and analyzed over time to evaluate the long term health of a probe.

In some embodiments, a quality assurance receive test may evaluate the receiving capabilities of each probe element in a similar (but opposite) process. In some embodiments, a calibration hydrophone (230 or 240) may transmit a precise ultrasonic test signal pulse or pulses of a known frequency. Each probe element may then receive the test signal and transform it into an electrical charge with a specific amplitude. The electric charges or amplitudes of the receiving probe elements may then be compared relative to each other and to any previous receive test data. Much like the transmitting test elements that are receiving poorly or not converting the ultrasonic pulses at all may fall out of tolerance. The average of the element receiving pulse amplitudes compared over time may indicate the degradation of elements. As above, test data may be logged, stored, and analyzed over time.

In some embodiments an ultrasound system operator technician may be provided with information about quality assurance calibration and test data resulting from the above processes. In some embodiments, a service provider and/or probe manufacturer may also be informed of calibration and/or test data, e.g. when elements are underperforming or no longer transmitting or receiving. This information can be used to decide when to schedule probe repairs or when a probe should be replaced. Compensation for elements which are no longer firing, or for the adjustment of transmit amplitude and receive gain of any particular element may then be done internally to the electronics of an ultrasound imaging system (e.g., MAUI electronics in the case of a multiple aperture ultrasound imaging system).

Although many of the embodiments of ultrasound probe calibration and quality assurance testing systems and methods are shown and described with reference to multiple aperture ultrasound imaging probes, these systems and methods can also be applied to single aperture ultrasound imaging systems.

Terms such as "optimized," "optimum," "precise," "exact" and similar terms used in relation to quantitative parameters are merely intended to indicate design parameters which may be controlled or varied in accordance with general engineering principles, and may involve a compromise based on the balancing of competing design factors. Use of these terms is not intended to imply or require that the parameters or components thereof are designed for the best possible or theoretical performance.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

We claim:

1. A method of calibrating an ultrasound probe, the method comprising:
   mounting an ultrasound probe having at least one array of ultrasound elements onto a calibration system adjacent to a tank;
   transmitting an ultrasound test signal from a first transmitting element of the probe into the tank and through a test medium of the calibration system;
   receiving the test signal at a first hydrophone disposed in the tank at a first time;
   receiving the test signal at a second hydrophone disposed in the tank at a second time;
   receiving the test signal at a third hydrophone disposed in the tank at a third time; and
   determining an acoustic position of the first transmitting element within a coordinate system defined relative to the probe based upon differences in the first time, the second time, and the third time.

2. The method of claim 1, the method further comprising repeating the transmitting, receiving, and determining steps for at least one additional transmitting element in the array.

3. The method of claim 2, wherein the transmitting, receiving, and determining steps are performed for every transmitting element in the array.

4. The method of claim 2, wherein the transmitting, receiving, and determining steps are performed for less than all of the transmitting elements in the array, the method further comprising interpolating acoustic positions of all remaining transmitting elements.

5. The method of claim 2, wherein the probe comprises a plurality of distinct arrays, and wherein the transmitting, receiving, and determining steps are performed for at least two elements in each array.

6. The method of claim 5, wherein the plurality of arrays are separated by physical space.

7. The method of claim 5, wherein at least one array is non-planar with respect to another array.

8. The method of claim 1, wherein the first, second, and third hydrophones are part of a first line hydrophones and fourth, fifth, and sixth hydrophones are part of a second line, wherein the first and second lines are parallel, the method further comprising receiving the test signal on all six hydrophones and determining an x, y, and z position of the element based on differences of arrival times at each hydrophone.

9. The method of claim 8, wherein a third line of two or more hydrophones is transverse to the first and second lines, the method further comprising computing the angle of transmission of the element based upon based upon the position of maximum levels of energy received on any of the hydrophones.

10. The method of claim 1, further comprising storing the determined position of the element in a memory chip on the probe.

11. The method of claim 1, further comprising overwriting position data stored in a memory chip with the determined position.

12. The method of claim 1, further comprising establishing a tank coordinate system relative to the first, second, or third hydrophone.

13. The method of claim 12, further comprising determining a position of every element of the probe relative to the tank coordinate system.

14. The method of claim 13, further comprising establishing a probe coordinate system relative to an element of the probe.

15. The method of claim 14, further comprising rotating or translating all of the determined transmitting element positions to the probe coordinate system.

16. The method of claim 1, wherein the position is determined relative to a Cartesian coordinate system.

17. The method of claim 1, further comprising storing the determined position in memory and retrieving the stored position during imaging or image processing.

18. The method of claim 1, further comprising transmitting an ultrasound test signal from a fourth hydrophone to the first, second, or third hydrophone to verify the operation of the first, second, or third hydrophone.

19. The method of claim 1, further comprising:
   transmitting a second ultrasound test signal between a fourth hydrophone disposed in the tank of the calibration system and a second element of the ultrasound probe, the transmitting occurring through a test medium in the tank of the calibration system; and
   determining an acoustic performance of the second element.

20. The method of claim 19, wherein the second test signal is transmitted from the fourth hydrophone and received by the second element.

21. The method of claim 19, wherein the second test signal is transmitted from the second element and received by the fourth hydrophone.

22. The method of claim 19, the method further comprising repeating the steps of transmitting a second ultrasound test signal, and determining an acoustic performance for at least one additional element in the array.

23. The method of claim 22, wherein the probe comprises a plurality of distinct arrays, and wherein the steps of transmitting a second ultrasound test signal and determining an acoustic performance are performed for at least one element of each array.

24. The method of claim 19, further comprising transmitting a third test signal from the first, second or third hydrophone, receiving the third test signal with a fourth hydrophone, and verifying performance of at least one hydrophone.

25. The method of claim 19, wherein the determined acoustic performance is stored and transmitted electronically to report probe performance to service providers and end users.

26. A system for calibrating an ultrasound probe, the system comprising:
   a tank substantially filled with a test medium;
   a dock attached to the tank, the dock configured to hold an ultrasound probe; and
   a plurality of hydrophones arranged in a matrix along a wall of the tank opposite the dock, the plurality of hydrophones being configured to receive one or more test signals from a transducer element of the ultrasound probe to determine an acoustic position of the transducer element; and
   a controller having instructions configured to transmit an ultrasound test signal from a first transmitting element of an ultrasound probe held in the dock into the tank and through the test medium;
   receiving the test signal at a first hydrophone of the matrix at a first time;
   receiving the test signal at a second hydrophone of the matrix at a second time;
   receiving the test signal at a third hydrophone of the matrix at a third time; and determining an acoustic position of the first transmitting element within a coordinate system defined relative to the probe based upon differences between the first time, the second time, and the third time.

27. The system of claim 26, further comprising the probe, wherein the probe comprises at least two arrays separated by a physical space, and wherein the dock is configured so as to hold at least one of the arrays at a non-orthogonal angle with respect to the hydrophone matrix.

28. The system of claim 26, wherein the probe comprises a calibration memory chip, the calibration memory chip configured to store data obtained by the calibration system.

29. The system of claim 26, wherein the dock is configured to conform to the ultrasound probe shape.

30. The system of claim 26, wherein the dock is configured such that, when the probe is positioned in the dock, the probe is directly adjacent to the test medium.

31. The system of claim 26, wherein material of the dock has substantially the same speed of sound as the test medium.

32. The system of claim 26, wherein the matrix includes a first row of hydrophones, a second row of hydrophones parallel to the first row of hydrophones, and a third row of hydrophones transverse to the first and second rows.

33. The system of claim 26, further comprising a calibrator hydrophone, the calibrator hydrophone located on a wall of the tank separate from the wall along which the plurality of hydrophone receivers are arranged.

* * * * *